(12) United States Patent
Lukhtanov

(10) Patent No.: US 11,920,040 B2
(45) Date of Patent: *Mar. 5, 2024

(54) CARBORHODAMINE COMPOUNDS AND METHODS OF PREPARATION THEREOF

(71) Applicant: ELITECHGROUP MDX LLC, Bothell, WA (US)

(72) Inventor: Eugeny A. Lukhtanov, Bothell, WA (US)

(73) Assignee: ELITECHGROUP MDX LLC, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/073,929

(22) Filed: Dec. 2, 2022

(65) Prior Publication Data

US 2023/0105320 A1 Apr. 6, 2023

Related U.S. Application Data

(62) Division of application No. 17/482,611, filed on Sep. 23, 2021, now Pat. No. 11,618,826, which is a division of application No. 16/403,980, filed on May 6, 2019, now Pat. No. 11,155,713.

(60) Provisional application No. 62/677,331, filed on May 29, 2018.

(51) Int. Cl.
| | | |
|---|---|---|
| *C09B 11/24* | (2006.01) | |
| *C12N 9/12* | (2006.01) | |
| *C12Q 1/68* | (2018.01) | |
| *C12Q 1/6876* | (2018.01) | |
| *G01N 21/64* | (2006.01) | |

(52) U.S. Cl.
CPC ............ *C09B 11/24* (2013.01); *C12N 9/1241* (2013.01); *C12Q 1/6876* (2013.01); *G01N 21/6486* (2013.01); *C12N 2310/3517* (2013.01); *C12Q 2561/101* (2013.01); *C12Q 2563/107* (2013.01)

(58) Field of Classification Search
CPC .................. C09B 11/24; C12N 9/1241; C12N 2310/3517; C12Q 1/6876; C12Q 2561/101; C12Q 2563/107; G01N 21/6486
See application file for complete search history.

(56) References Cited

U.S. PATENT DOCUMENTS 11,155,713 B2 * 10/2021 Lukhtanov ......... G01N 21/6486

\* cited by examiner

*Primary Examiner* — Jezia Riley
(74) *Attorney, Agent, or Firm* — Jackson Walker LLP

(57) ABSTRACT

The carborhodamine dyes disclosed herein are novel reagents suitable for automated incorporation of carborhodamine dyes into oligonucleotides that can be used in detection methods for nucleic acid targets. This disclosure provides an efficient and simple process for the preparation of carborhodamine compounds and introduces previously unknown reagents for the automated synthesis of oligonucleotide-carborhodamine conjugates.

10 Claims, 21 Drawing Sheets

Specification includes a Sequence Listing.

CARBORHODAMINE COMPOUNDS AND METHODS OF PREPARATION THEREOF

This application is a divisional of and claims priority to U.S. patent application Ser. No. 17/482,611, entitled "Carborhodamine Compounds and Methods of Preparation Thereof," filed Sep. 23, 2021, which is a divisional of and claims priority to U.S. patent application Ser. No. 16/403,980, entitled "Carborhodamine Compounds and Methods of Preparation Thereof," filed May 6, 2019, which claims priority to U.S. Provisional Patent Application Ser. No. 62/677,331, entitled "Carborhodamine Compounds and Methods of Preparation Thereof," filed May 29, 2018, the entire contents of which are hereby incorporated by reference.

BACKGROUND

This disclosure pertains to synthetic methods for the preparation of carborhodamine dyes. The disclosure also pertains to novel reagents suitable for automated incorporation of carborhodamine dyes into oligonucleotides as well as to the use of oligonucleotide-carborhodamine conjugates in detection methods for nucleic acid targets.

Carborhodamine dyes previously disclosed in U.S. Pat. Nos. 6,828,159, 7,935,822, 9,745,336 demonstrate a number of useful photo-chemical properties such as red-shifted absorption and fluorescence spectra (Kolmakov et al. (2010), Grimm et al. (2013)), high fluorescence quantum yield and photostability (Kolmakov et al. (2010)). These properties are essential for fluorescence-based histological staining techniques and signal detection in research and diagnostic applications. DNA probes labeled with fluorescent dyes are critical for nucleic acid molecular diagnostic assays. Probes labeled with spectrally separated dyes allow for simultaneous detection of multiple targets. The dyes of choice for the red region (600-700 nm excitation wavelengths) of the spectral range have been carbocyanine dyes like Cy5 and Cy5.5 In spite of their low chemical stability and photo/temperature sensitivity, they remain to be popular due to the ease of preparation and availability of phosphoramidite reagents. If made more accessible, carborhodamine dyes offer significant improvement in performance and stability of fluorogenic nucleic acid probes.

Oligonucleotide-carborhodamine conjugates have been prepared by a post-synthetic modification of oligonucleotides bearing an aliphatic amino group with a carborhodamine NHS ester. Although suitable for most research needs, this procedure requires additional purification steps, has low throughput and, as a consequence, high manufacturing cost. To enable a high throughput on-line conjugate preparation dye-modified synthesis solid supports and phosphoramidites are required. This approach, which requires relatively large amounts of dye-phosphoramite intermediates, is hampered by the notoriously complex synthetic chemistry of the carborhodamine dyes. Other potential complications on the way to implementing the on-line approach are related to compatibility with the oligonucleotide synthesis. A prospective dye-solid support or phosphoramidite must demonstrate high coupling efficiency and be stable towards the synthesis cycle and deprotection conditions.

SUMMARY

This disclosure pertains to carborhodamine dyes, novel reagents suitable for automated incorporation of carborhodamine dyes into oligonucleotides, and the use of oligonucleotide-carborhodamine conjugates in detection methods for nucleic acid targets. This disclosure provides an efficient and simple process for the preparation of carborhodamine compounds and introduces previously unknown reagents for the automated synthesis of oligonucleotide-carborhodamine conjugates.

DETAILED DESCRIPTION

Figure 1:
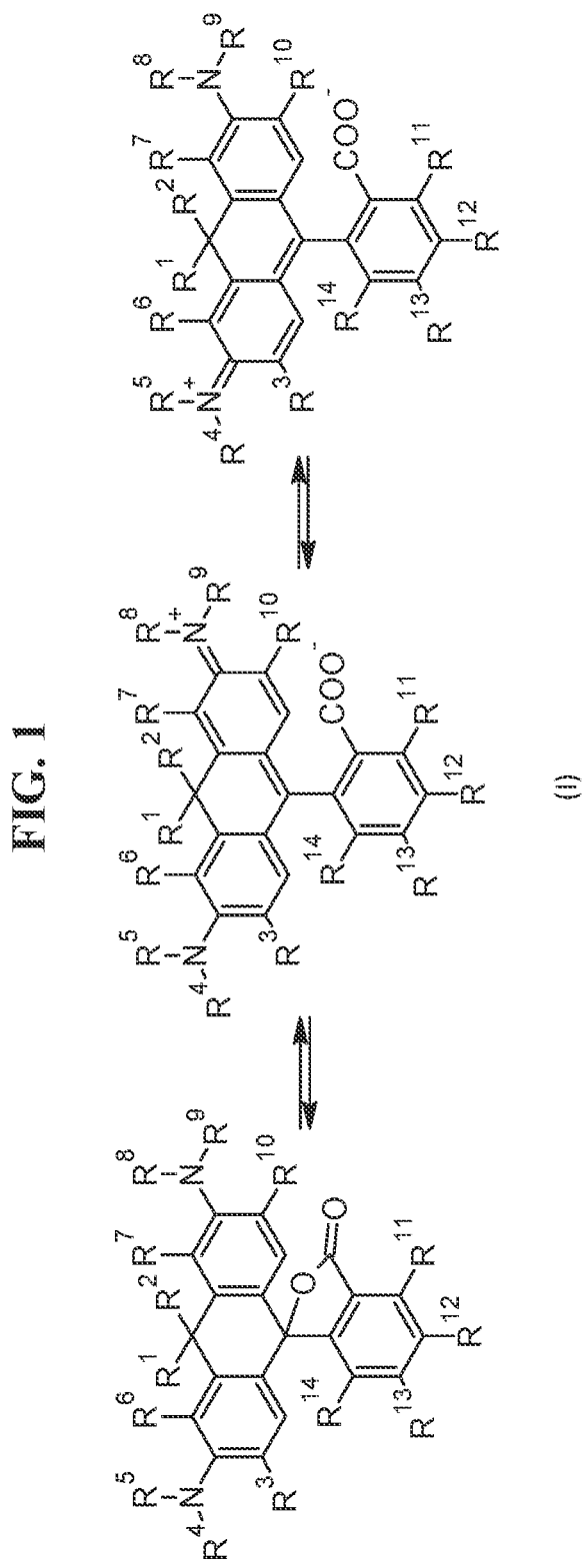
FIG. 1 shows a general structure of carborhodamine compounds that exist in an equilibrium between the Spirolactone (left structure) and the tautomeric zwitter ionic (central and right structures) forms.

This disclosure pertains to carborhodamine dyes, novel reagents suitable for automated incorporation of carborhodamine dyes into oligonucleotides, and the use of oligonucleotide-carborhodamine conjugates in detection methods for nucleic acid targets. This disclosure provides an efficient and simple process for the preparation of carborhodamine compounds and introduces previously unknown reagents for the automated synthesis of oligonucleotide-carborhodamine conjugates.

The term "linker" and "linking group" refers to a moiety that is used to assemble various portions of a molecule, to covalently connect two or more molecules or to covalently attach a molecule (or portions thereof) to a substrate (e.g. solid support). Typically, a linker or linking group has functional, protected or precursors (groups that can be converted to functional groups) of functional groups that are used to interact with and form covalent bonds with functional groups in other molecules, portions of molecules or substrates. Additionally, a linker can include linear or acyclic portions, cyclic portions, aromatic rings or combinations thereof (U.S. Pat. Nos. 5,419,966; 5,696,251; 5,585,481; 5,942,610 and 5,736,626).

The terms "functional" and "reactive" groups in this invention are used interchangeably and refer to chemical groups and moieties that are suitable for the formation of a chemical bond. They are exemplified but not limited to alcohols, amines, oxyamines, hydrazines, hydrazides, semicarbazides, semi-thiocarbazides, hydroxyl-substituted compounds, sulfur compounds (such as thiols, dithiols, thiocarbonyl compounds, phosphorothiates), carboxylates, phosphates, phosphonates, aromatic nitrogens (such as in pyridine), amide nitrogens, azides, electron-rich aromatics, etc.), acids (in the presence of activating agents), esters, imidoesters, anhydrides, acid chlorides, acyl azides, lactones, azlactones, isocyanates, isothiocyanates, o-acylisoureas, acid amides (such as acyl imidazolides or phosphoramidites), carbonyl compounds, halogenated hydrocarbons, halogenated aromatics (such as triazine chloride, electron-deficient fluoroaromatics), unsaturated hydrocarbons, aromatic diazonium salts, epoxides, aziridines. Other types of functional or reactive groups include photoreactive (azides, benzophenones, diazirines, etc.), metal chelating groups (aminodiacetic acid), substrates for metal-catalyzed coupling, ligands for molecular recognition (such as biotin), antigens and haptens. Functional and reactive groups of this invention may also be used in conjunction with bi-functional or poly-functional cross-linking reagents (such as bis-amines, bis-aldehydes, maleimido-NHS esters, etc). Other examples of reactive groups and cross-linking reaction can be found in literature (Hermanson (1996)).

The terms "protecting group" or "protected form thereof" or "protected functional group" or "blocking group" refer to a grouping of atoms that, when attached to a reactive group in a molecule, masks, reduces or prevents that reactivity. Examples of protecting groups can be found in Greene at al. (2007) and Harrison and Harrison et al (1971 to 1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilylethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

The term "leaving group" refers to a molecular fragment that departs with a pair of electrons in heterolytic bond cleavage. Common leaving groups are halides such as Cl-, Br-, and I-, sulfonate esters such as tosylate (TsO-), phenolates such as 4-nitrophenylate and water (Smith, (2007)).

The term "solid support" or "synthesis solid support" refers to any support that is compatible with oligonucleotide synthesis including, for example, glass, controlled pore glass, polymeric materials, polystyrene, beads, coated glass and the like.

The term "alkyl" refers to a linear, branched, or cyclic saturated monovalent hydrocarbon substituent or a combination of cyclic and linear or branched saturated monovalent substituents having the number of carbon atoms indexed in the prefix. For example, $(C_1-C_8)$alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, aralkyloxy), when a prefix is not included to indicate the number of chain carbon atoms in an alkyl portions, the substituent thereof will have eight or fewer main chain carbon atoms.

The term "acyl" group refers to the R—C(=O)— group (R=H, alkyl group, aryl group) in a carboxylic acid or a carboxylic acid derivative.

The prefix "hetero" refers to a group, such as alkyl, aryl, alkylene or arylene, wherein one or more heteroatoms, such as nitrogen, oxygen, sulfur, phosphorus, chlorine, bromine, or iodine, have replaced one or more main chain or ring carbons.

The term "alkenyl group" refers to a monovalent group —$C_nH_{2n-1}$ formed from an alkene by removal of one hydrogen atoms from any carbon atom.

The term "alkynyl group" refers to a monovalent group —$C_nH_{2n-3}$ formed from an alkyne by removal of one hydrogen atoms from any carbon atom.

The term "alkylene" refers to a linear saturated divalent hydrocarbon substituent or a branched saturated divalent hydrocarbon substituent having the number of carbon atoms indicated in the prefix. For example, $(C_1-C_6)$alkylene is meant to include methylene, ethylene, propylene, 2-methylpropylene, pentylene, and the like.

The term "alkenylene" refers to a linear divalent hydrocarbon substituent formed from an alkene by removal of two hydrogen atoms from any two carbon atom having the number of carbon atoms indicated in the prefix. For example, $(C_2-C_6)$alkenylene is meant to include ethenylene, propenylene, 2-methylpropenylene, pentenylene, and the like.

The term "alkynylene" refers to a linear divalent substituent formed from an alkyne by removal of two hydrogen atoms from any two carbon atom having the number of carbon atoms indicated in the prefix. For example, $(C_2-C_6)$ alkynylene is meant to include ethynylene, propynylene, 2-methylpropynylene, pentynylene, and the like.

The term "arylene" refers to a bivalent group derived from an arene by removal of a hydrogen atom from each of two ring carbon atoms.

The term "aromatic" or "aryl" means a monovalent or bivalent (e.g., arylene) monocyclic, bicyclic aromatic or tricyclic hydrocarbon substituent of 5 to 14 ring atoms which is unsubstituted or substituted. If substituted the substituents are selected from those groups provided below.

The term "heteromatic" or "heteroaryl" refers to aryl wherein one or more heteroatoms or heteroatom functional groups have replaced a ring carbon, while retaining aromatic properties, e.g., pyridyl, quinolinyl, quinazolinyl, thienyl, and the like. More specifically the terms aryl and heteroaryl include, but are not limited to, phenyl, 1-naphthyl, 2-naphthyl, thienyl, thiazolyl and benzothiazolyl, and the substituted forms thereof. Substituents for the aryl and heteroaryl groups are varied and are selected from: halo, —OR', —OC(O)R', —NR'R", —SR', —R', —CN, —NO$_2$, —CO$_2$R', —CONR'R", —C(O)R', —OC(O) NR'R", —NR"C(O)R', —NR"C(O)OR', —NR'C(O)NR"R''', —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro (C$_1$-C$_4$)alkoxy, and perfluoro(C$_1$-C$_4$)alkyl, in a number ranging from zero to the total number of open valences on the aromatic ring system; and where R', R" and R''' are independently selected from H, (C$_1$-C$_8$)alkyl and (C$_1$-C$_8$) heteroalkyl (alkyl wherein one or more alkyl carbons replaced by heteroatoms), unsubstituted aryl and heteroaryl, (unsubstituted aryl)-(C$_1$-C$_4$)alkyl, and (unsubstituted aryl) oxy-(C$_1$-C$_4$)alkyl. Preferred substituents are —OH, halogen, OR', —OC(O)R', —NR'R", —SR', —R', —CN and —NO$_2$— where R' and R" are independently —H— or —(C$_1$-C$_4$).

The term "substituted" refers to a chemical structure wherein one or more hydrogens of the "unsubstituted" parent compound are independently replaced with another atom or a group of atoms.

The prefix "halo" and the term "halogen," when used to describe a substituent, refer to —F, —Cl, —Br and —I.

Certain compounds of the present disclosure may exist in a salt form. Such salts include base addition salts such as sodium, potassium, calcium, ammonium, organic amino, or magnesium salt, or a similar salt. When the compounds or modified oligonucleotides of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (Berge, S. M., et al. 1977). Certain specific compounds described herein contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers and individual isomers are all intended to be encompassed within the scope of the present disclosure. The methods for the determination of stereochemistry and the separation of isomers are well-known in the art (March (1992).

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not (e.g, $^2$H), are intended to be encompassed within the scope of the present disclosure.

The term "oligonucleotide" or ODN refers to a fragment of natural or artificial nucleic acid or combination of thereof. Examples of artificial nucleic acids include analogues with modified sugar-phosphate backbone such as 2-OMe nucleic acid, peptide nucleic acid (PNA), locked nucleic acid (LNA), threose nucleic acid (TNA), glycol nucleic acid (GNA) (U.S. Pat. Nos. 5,539,082, 8,293,684 and 9,464, 316). Artificial nucleic acid (U.S. Pat. No. 9,169,256) may also comprise modified nucleobases.

The term "minor groove binder" refers to a moiety that is capable of forming a complex (typically non-covalent) with the minor groove of DNA. The minor groove binders of the invention are oligonucleotide conjugates (or "probes") as described in U.S. Pat. Nos. 5,801,155 and 6,312,894, both hereby incorporated by reference. These conjugates form hyper-stabilized duplexes with complementary DNA. In particular, sequence specificity of short minor groove binder probes is excellent for high temperature applications such as PCR. The probes/conjugates of the present disclosure can also have a covalently attached minor groove binder. A variety of suitable minor groove binders have been described in the literature (U.S. Pat. No. 5,801,155; Wemmer (1997), Walker (1997), Zimmer (1986) and Reddy (1999)). Suitable methods for attaching minor groove binders (as well as reporter groups such as fluorophores and quenchers) through linkers to oligonucleotides have also been described (U.S. Pat. Nos. RE 38,416; 5,512,667; 5,419, 966; 5,696,251; 5,585,481; 5,942,610 and 5,736,626).

The term "quencher" refers to an organic moiety that is capable of reducing the efficiency of light re-imission by a fluorophore. Quenchers have been disclosed in U.S. Pat. Nos. 3,996,345, 6,727,356 and 6,790,945, Matayoshi (1990), and Doose (2009).

The term "modified nucleobases or modified bases" refers to those bases that differ from the naturally-occurring bases (adenine, cytosine, guanine, thymine, and uracil) by addition or deletion of one or more functional groups, differences in the heterocyclic ring structure (i.e., substitution of carbon for a heteroatom, or vice versa), and/or attachment of one or more linker arm structures to the base. Modified bases include naturally-occurring and synthetic modifications and analogues of the major bases such as, for example, hypoxanthine, 2-aminoadenine, 2-thiouracil, 2-thiothymine, inosine, 5-N$^4$-ethenocytosine, 4-aminopyrrazolo[3,4-d]pyrimidine and 6-amino-4-hydroxy-[3,4-d]pyrimidine. Any modified nucleotide or nucleotide analogue compatible with hybridization of probe with a nucleic acid conjugate to a target sequence is useful, even if the modified nucleotide or nucleotide analogue itself does not participate in base-pairing, or has altered base-pairing properties compared to naturally-occurring nucleotides. Examples of modified bases are disclosed in U.S. Pat. Nos. 7,045,610; 5,824,796; 6,127,121; 5,912,340; and PCT Publications WO 01/38584 and WO 01/64958, each of which is hereby incorporated herein by reference in its entirety. Preferred modified bases include 5-hydroxybutynyl uridine for uridine; 4-(4,6-Di-amino-$^1$H-pyrazolo[3,4-d]pyrimidin-3-yl)-but-3-yn-1-ol, 4-amino-$^1$H-pyrazolo[3,4-d]pyrimidine, and 4-amino-$^1$H-pyrazolo[3,4-d]pyrimidine for adenine; 5-(4-Hydroxy-but-1-ynyl)-1H-pyrimidine-2,4-dione for thymine; and 6-amino-$^1$H-pyrazolo[3,4-d]pyrimidin-4(5H)-one for guanine. Particularly preferred modified bases are "Super A°: 4-(4, 6-Diamino-1H-pyrazolo[3,4-d]pyrimidin-3-yl)-but-3-yn-1-ol," "Super G®: 4-hydroxy-6-amino pyrazolopyrimidine" (elitechgroup.com) and "Super T®: 5-(4-hydroxy-but-1-ynyl)-1H-pyrimidine-2,4-dione". "Super-D™: 3-Alkynyl pyrazolopyrimidine" analogues as universal bases are disclosed in U.S. Patent Application Publication No. 2012/0244535, incorporated by reference.

"Optional" or "optionally" in the above definitions and the disclosure means that the subsequently described event or circumstance may but need not occur, and that the description includes instances where the event or circumstance occurs and instances in which it does not. For example, "aryl optionally mono- or di-substituted with an alkyl group" means that the alkyl group may, but need not, be present, and the description includes situations where the aryl group is mono- or bis-substituted with an alkyl group and situations where the aryl group is not substituted with the alkyl group.

New methods for the preparation of carborhodamine compounds of general Structure I are disclosed. As shown in FIG. 1, such compounds exist in an equilibrium between the Spiro-lactone (left structure) and the tautomeric zwitter ionic (central and right structures) forms, and the Spiro-lactone form, which is chiefly used in this disclosure, represents the tautomeric forms as well.

Figure 2:
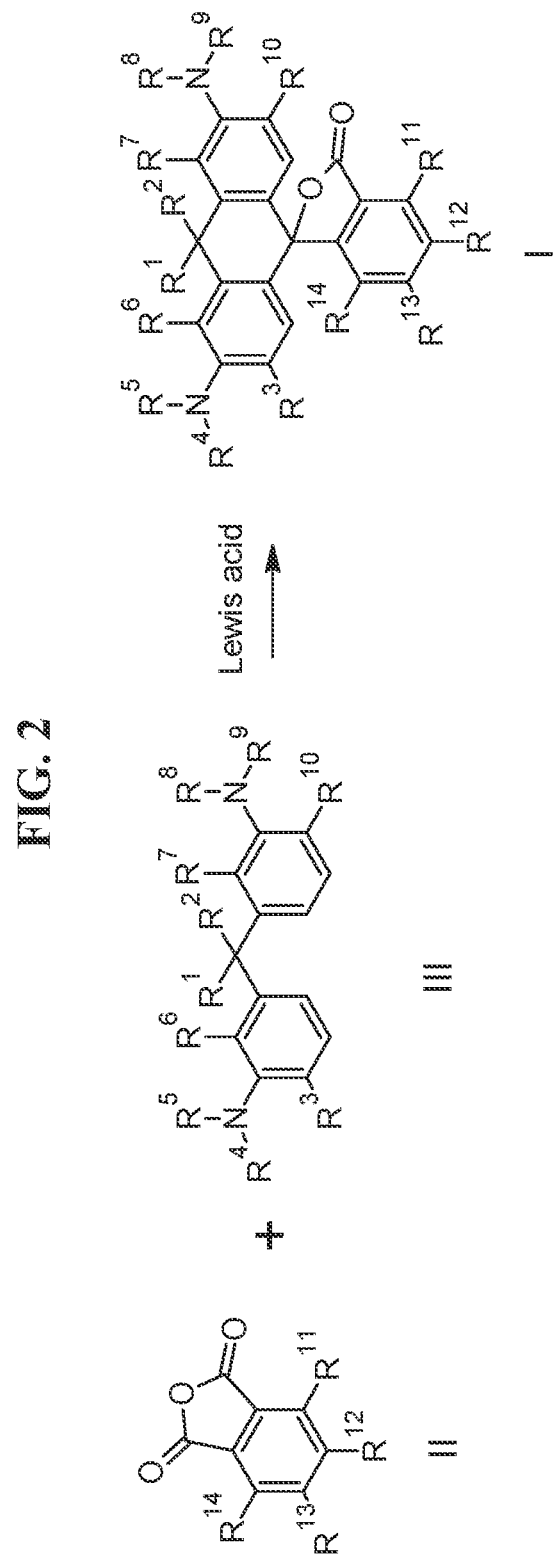
FIG. 2 shows a general synthetic scheme for the preparation of compounds of Structure I.

According to this disclosure, carborhodamine compounds of Structure I are efficiently prepared according to Scheme 1, shown in FIG. 2, using a one-step procedure wherein substituted phthalic anhydrides of Structure II are condensed with certain 3,3'-diaminophenylmethane analogues of Structure III in the presence of a Lewis acid.

The condensation reaction is preferably carried out in 1,2-dichloroethane. Other solvents that are compatible with Friedel-Crafts acylation (e.g. nitrobenzene, chlorobenzene, carbon disulfide) can be used as well. The reaction depicted in Scheme 1 is carried out in the presence of a Lewis acid, preferably aluminum chloride. Various other Lewis acids are known (Carlson (1986), Kobayashi (2000)) and commercially available.

Figure 3:
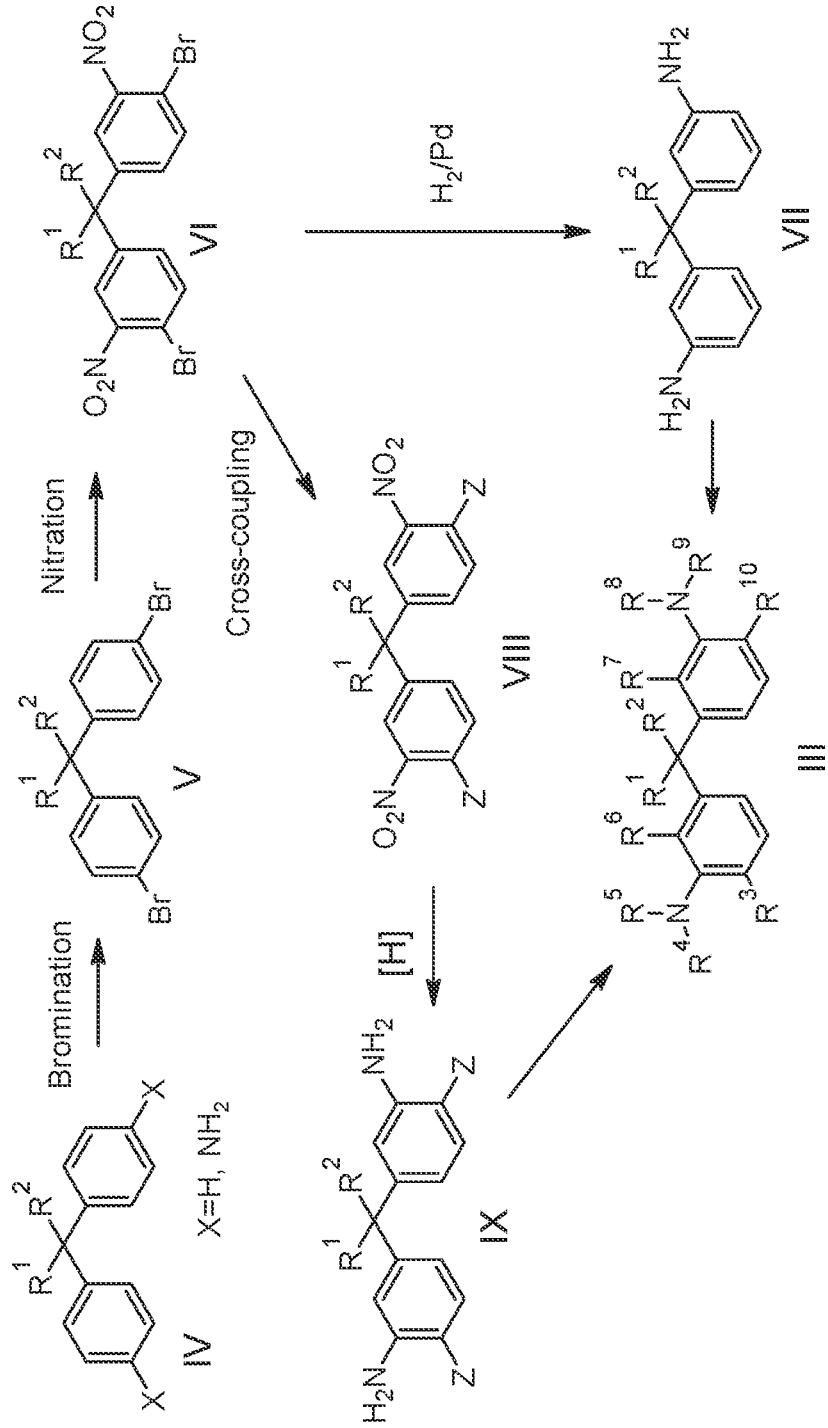
FIG. 3 shows a general synthetic scheme for the preparation of compounds of Structure III.

3,3'-Diaminophenylmethane analogues of Structure III are prepared according to Scheme 2, shown in FIG. 3, starting from compounds of Structure IV, which are commercially available or synthesized according to known methods (U.S. Pat. No. 5,037,994, Riccardo (2013)). Generally, the substituents $R^1$ and $R^2$ in Structure IV are independently selected from $(C_1-C_{20})$alkyl, $(C_1-C_{20})$heteroalkyl or taken together form a ring structure of one or more rings. When more than one ring is present, the rings are fused, bridged or Spiro-linked. Optionally, one or more hydrogens of the alkyl, heteroalkyl or the ring structure is replaced with a linking group. If present, linking group is selected from $(C_1-C_{20})$alkyl, aryl, $(C_1-C_{20})$heteroalkyl, heteroaryl or combination thereof where at least one hydrocarbon hydrogen is replaced with $R^{17}C(O)$— or $R^{18}O$— wherein $R^{17}$ is selected from HO—, alkoxy and $R^{18}$ is selected from H—, $(C_1-C_{20})$ alkyl or acyl.

According to the methods of this disclosure, compounds of structure IV are converted to halogenated, preferably brominated, compounds of Structure V using either direct (X=H) or Sandmeyer (X=NH$_2$) bromination, and then nitrated to yield compounds of general Structure VI. In the next step, compounds of Structure VI are either hydrogenated to yield 3,3'-diaminophenylmethanes of Structure VII or subjected to a carbon-carbon or carbon-heteroatom cross-coupling reaction to give compounds of general Structure VIII wherein Z represents a coupled group. Wide variety of cross-coupling reactions are known (for example Molander (2013)) and suitable for introduction of various Z substituents including unsubstituted or substituted aryl, heteroaryl, alkenyl, alkynyl groups. Dinitro-substituted compounds of structure VII are reduced by hydrogenation or using a reducing agent to diamino-substituted compounds of Structure IX. Compounds VII and IX are further subjected to various well known reactions to furnish ring structures, introduce alkyl, hereroalkyl, linking or functional groups and thus complete the preparation of compounds of Structure III. Without limiting the scopes of this disclosure, some examples of compounds of Structure III are shown in Table 1 below.

TABLE 1

Examples of compounds of general Structure III

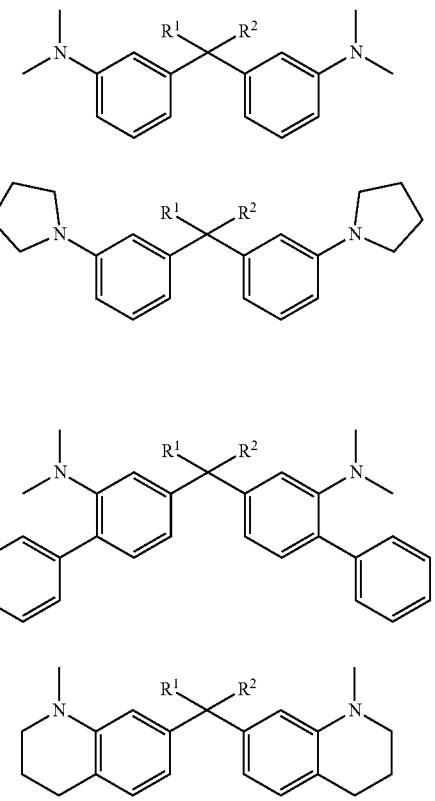

TABLE 1-continued

Examples of compounds of general Structure III

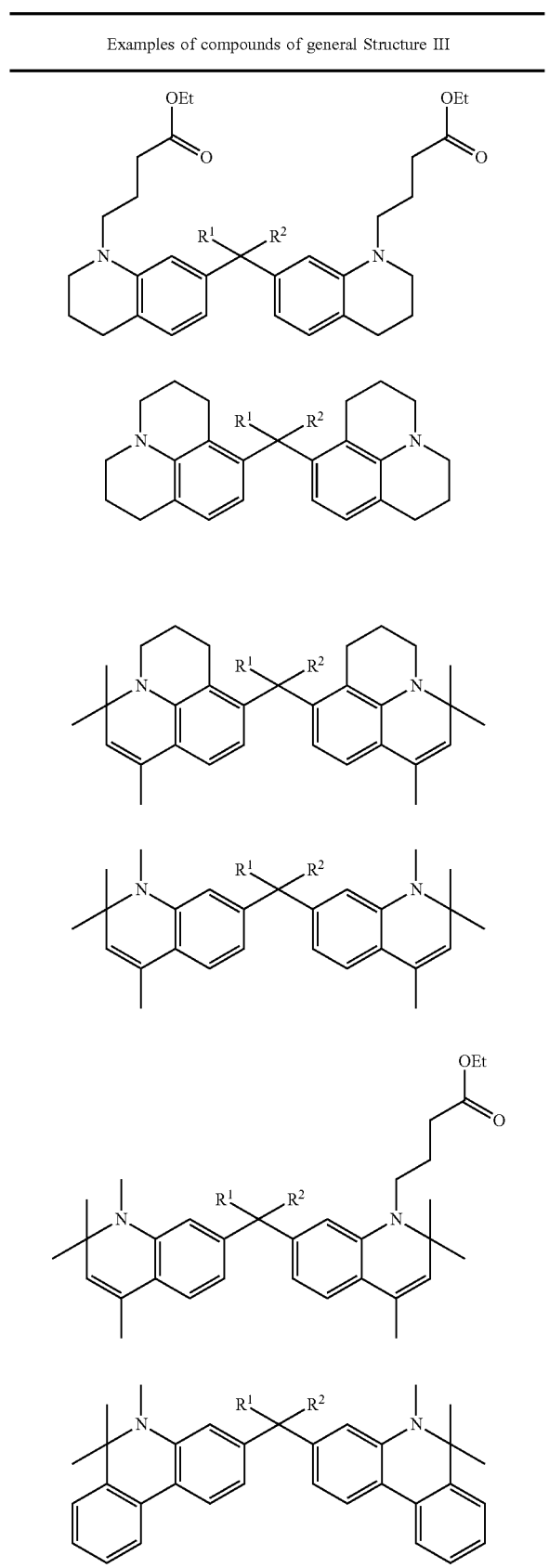
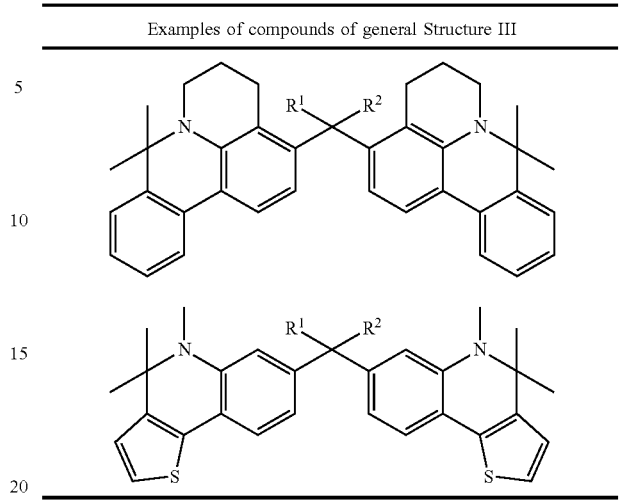

More generally, in Structure III shown in FIG. 3, $R^3$, $R^6$, $R^7$, and $R^{10}$ are independently selected from H, unsubstituted or substituted $(C_1\text{-}C_{20})$alkyl, $(C_1\text{-}C_{20})$alkoxy, $(C_1\text{-}C_{20})$alkenyl, $(C_1\text{-}C_{20})$alkynyl, unsubstituted or substituted aryl or heteroaryl, a linking group, halo, —OR', —OC(O)R', —NR'R'', —SR', —OC(O) NR'R'', —NR''C(O)R', —NR''C(O)OR', — NR'C(O)NR''R''', —SO$_2$H, where R', R'' and R''' are independently selected from H, $(C_1\text{-}C_8)$alkyl and heteroalkyl, unsubstituted or substituted aryl or heteroaryl or a linking group;

$R^4$, $R^5$, $R^8$ and $R^9$ are independently selected from H, unsubstituted or substituted $(C_1\text{-}C_{20})$alkyl, $(C_1\text{-}C_{20})$alkoxy, $(C_1\text{-}C_{20})$alkenyl, $(C_1\text{-}C_{20})$alkynyl, unsubstituted or substituted aryl or heteroaryl, a linking group; or $R^3$, $R^4$, $R^5$, $R^6$, $R^7$, $R^8$, $R^9$, $R^{10}$ may form one or more 4- to 7-member ring systems by bridging $R^3$ with $R^4$ or/and $R^4$ with $R^5$ or/and $R^5$ with $R^6$ or/and $R^7$ with $R^8$ or/and $R^8$ with $R^9$ or/and $R^9$ with $R^{10}$, which are, optionally, fused, bridged or Spiro-linked to other 4- to 7-member ring systems, each with 0 to 3 double bonds and optionally containing heteroatoms.

Substituted phthalic anhydrides of Structure II are either commercially available or prepared according to known methods of organic chemistry. Generally, the R11, R12, R13 and R14 substituents in Structures I and II independently selected from H, $(C_1\text{-}C_{20})$alkyl, $(C_1\text{-}C_{20})$alkoxy, $(C_1\text{-}C_{20})$alkenyl, $(C_1\text{-}C_{20})$alkynyl, unsubstituted or substituted aryl, unsubstituted or substituted heteroaryl, linking group, halo, —OR', —OSO$_2$R', —OC(O)R', —NR'R'', —SR', —R', —CN, —NO$_2$, —CO$_2$R', —CONR'R'', —C(O)R', —SO$_2$R', —SO$_2$NR'R'', —N$_3$, —CH(Ph)$_2$, perfluoro$(C_1\text{-}C_4)$alkoxy, and perfluoro$(C_1\text{-}C_4)$alkyl where R' and R'' are independently selected from H, $(C_1\text{-}C_{20})$alkyl perfluoro$(C_1\text{-}C_4)$alkyl and heteroalkyl, unsubstituted or substituted aryl or heteroaryl.

Optionally, in Strucutres I and II, one or more 4- to 7-member ring systems are formed by bridging $R^{11}$ with $R^{12}$ or/and $R^{12}$ with $R^{13}$ or/and $R^{13}$ with $R^{14}$, which are, optionally, fused, bridged or Spiro-linked to other 4- to 7-member ring systems, each with 0 to 3 double bonds and optionally containing heteroatoms. Linking group is selected from $(C_1\text{-}C_{20})$alkyl, aryl, $(C_1\text{-}C_{20})$heteroalkyl, heteroaryl or combination thereof wherein at least one of the hydrocarbon hydrogens is replaced with a protected or unprotected carboxyl or a hydroxyl group wherein protecting groups is selected from an amide, an ester or an ether group.

As disclosed above some compounds of Structure I may be prepared to contain one or more linking groups with one or more carboxyl or hydroxyl groups that are suitable or readily converted into groups suitable for oligonucleotide conjugation and, particularly, automated oligonucleotide synthesis. The required functional groups typically include carboxyl-, activated carboxyl, hydroxyl-, protected hydroxyl, which are further modified to furnish phosphoramidites, solid supports and, eventually, oligonucleotide conjugates.

On the other hand, other compounds of Structure I may require further modifications to introduce additional linking and functional groups. This can be accomplished by employing the existing functional group (such as halogen, —SO$_2$CF$_3$, —COOH, —OH, —SH, —NH$_2$, —CN, etc.) of compounds of Structure I for adding a linking group followed by the introduction of the necessary functional groups.

One particularly important example of that approach utilizes the compounds of Structure I wherein one or more of $R^{11}$, $R^{12}$, $R^{13}$ or $R^{14}$ are halogens, preferably, bromine, iodine or —OSO$_2$R' (wherein R' as previously defined). Such compounds are efficient substrates for various carbon-carbon and carbon-heteroatom cross-coupling reactions (Molander (2013)) and thus useful for the introduction of linking and functional groups.

Figure 4:
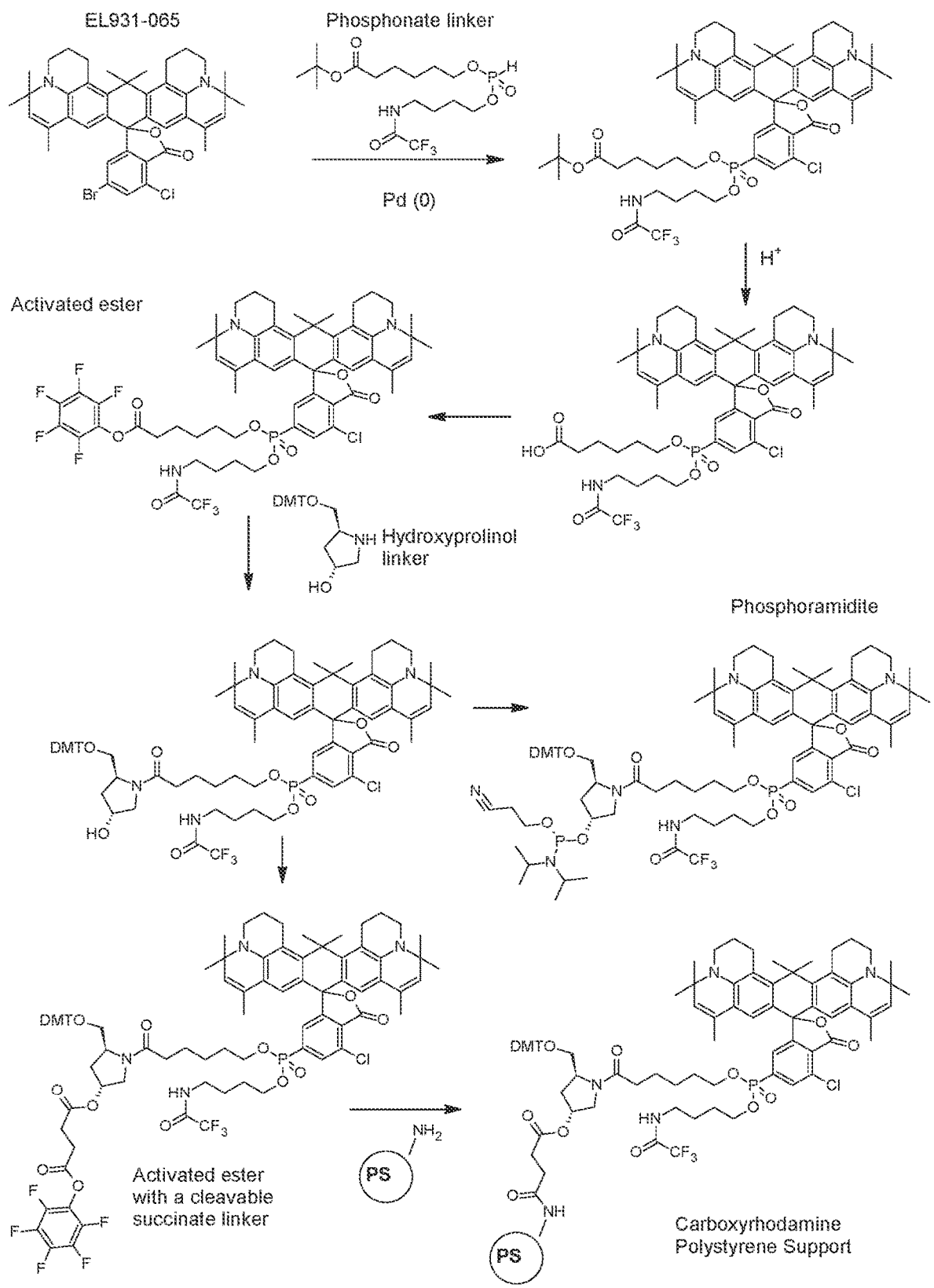
FIG. 4 shows a synthetic scheme for the preparation of exemplary phosphonate-modified carborhodamine activated esters, a phosphoramidite and a carborhodamine-modified polystyrene support.

One example of useful linkers for cross-coupling reactions are certain di-substituted phosphonates (disclosed in U.S. Pat. Nos. 7,767,834 and 8,163,910) wherein each substituent is either a linking or a protecting group. The protecting group is used to block the latent negative charge of the phosphonate group whereas the linking group is used to introduce the required functional groups (e.g. activated esters, phosphoramidites) or to add another linker or to couple to a solid support as illustrated in FIG. 4. The activated esters, phosphoramidites and modified solid supports are crucial for implementing a high throughput manufacturing process of oligonucleotide-carborhodamine conjugates.

Accordingly, carborhodamine compounds and conjugates of Structure I wherein at least one of $R^{11}$, $R^{12}$, $R^{13}$ or $R^{14}$ is replaced with a phosphonate group of general structure X are also disclosed:

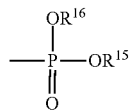
(X)

wherein the free phosphorus valence on the left side of the structure connects to one of the $R^{11}$-$R^{14}$ aromatic carbons of Structure I;

$R^{15}$ is selected from H—, NH$_2$(CH)$_4$—, NH$_2$(CH$_2$)$_5$—, CF$_3$C(O)NR'(CH$_2$)$_4$—, CF$_3$C(O)NR'(CH$_2$)$_5$—, (CH$_3$)$_3$COC(O)NR'(CH$_2$)$_4$—, (CH$_3$)$_3$COC(O)NR'(CH$_2$)$_5$—, tert-butyl, methyl, aryl, wherein R' is selected from H— and (C$_1$-C$_8$)alkyl;

$R^{16}$ is either the same as $R^{15}$ or selected from (C$_1$-C$_{100}$)alkyl, aryl, (C$_1$-C$_{100}$)heteroalkyl, heteroaryl or combination thereof and, when $R^{16}$ is not the same as $R^{15}$, at least one of hydrocarbon hydrogens in $R^{16}$ is independently replaced with —C(O)R$^{17}$ or —OR$^{18}$ wherein $R^{17}$ is selected from HO—, alkoxy, a leaving group or a nitrogen atom of an alkylamino group in an alkylamine-modified oligonucleotide and $R^{18}$ is selected from H—, dimethoxytrityl, NCCH$_2$CH$_2$OP(N(i-Pr)$_2$)—, a phosphorus atom of a phosphate group in an oligonucleotide, or —C(O)—R$^{19}$—C(O)R$^{20}$— wherein $R^{19}$ is a divalent group selected from (C$_1$-C$_{20}$)alkylene, arylene, (C$_1$-C$_{20}$)heteroalkylene, heteroarylene or combination thereof and $R^{20}$ is selected from HO—, a leaving group or a nitrogen atom of an amino group in an amine-modified solid support.

Those structures encompass useful amine-, carboxy- and hydroxy-modified derivatives of carborhodamine compounds as well as activated esters, phosphoramidites, solid supports and oligonucleotide conjugates.

Figure 5:
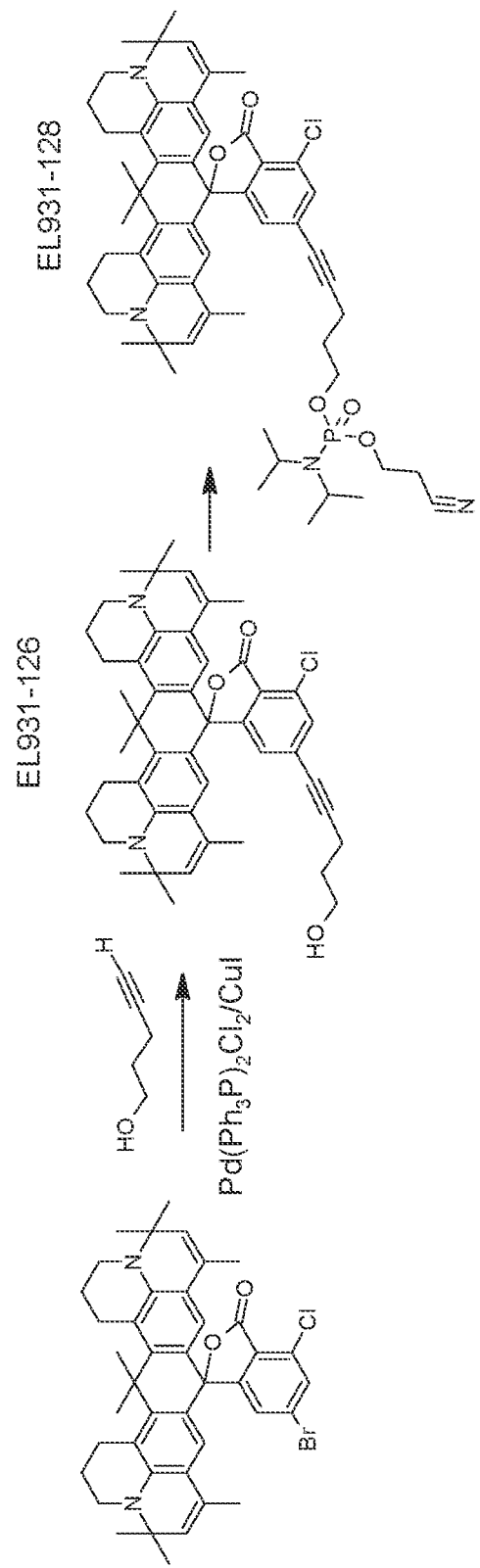
FIG. 5 shows a synthetic scheme for the preparation of an exemplary phosphoramidite with an alkynyl-modified carborhodamine.

Other examples of useful linkers for cross-coupling reaction with compounds of Structure I (wherein one or more $R^{11}$, $R^{12}$, $R^{13}$ or $R^{14}$ are halogens or —OSO$_2$R') include functionalized 1-alkynes, alkenes, arenes or heteroarenes as exemplified in FIG. 5. Incorporation of such linkers provides compounds of structure I where at least one of $R^{11}$, $R^{12}$, $R^{13}$ or $R^{14}$ is replaced with a linker of general structure XI:

(XI)

wherein $R^{21}$ is a divalent group selected from alkylene, alkenylene, alkynylene, arylene, heteroalkylene, heteroalkenylene, heteroalkynylene, and heteroarylene where one free valence connects to one of the $R^{11}$-$R^{14}$ aromatic carbons of Structure I and the other free valence connects to $R^{22}$. $R^{22}$ is selected from (C$_1$-C$_{100}$)alkyl, aryl, (C$_1$-C$_{100}$)heteroalkyl, heteroaryl or combination thereof and at least one of the hydrocarbon hydrogens in $R^{22}$ or $R^{21}$ is independently replaced with —C(O)R$^{17}$ or —OR$^{18}$ wherein $R^{17}$ and $R^{18}$ are as previously defined.

Similarly, the compounds of structure I wherein one or more of $R^{11}$, $R^{12}$, $R^{13}$ or $R^{14}$ are HOOC—, HO—, HS—, NC— can be easily modified (Hermanson (1996)) to introduce the required linkers.

In another example a linker is introduced by coupling the Spiro-lactone carboxyl group of compounds of Structure I to an alcohol, a secondary amine or an amine-containing linker.

Carborhodamine compounds of this disclosure, which include but are not limited to activated esters, phosphoramidites, solid supports and oligonucleotide conjugates, are prepared according to any of the methods disclosed above and summarized in one general structure XII.

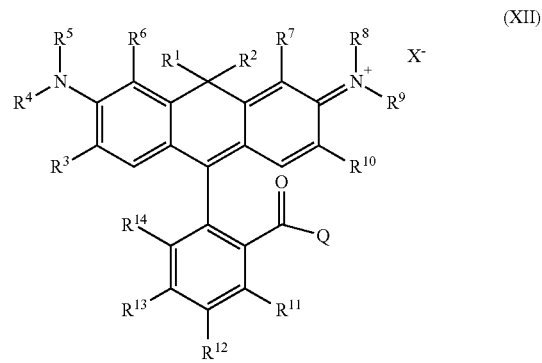
(XII)

Wherein:
$R^1$ and $R^2$ are independently (C$_1$-C$_{100}$)alkyl or (C$_1$-C$_{100}$)heteroalkyl, or taken together form a ring structure of one or more rings. When more than one ring is present, the rings may be fused, bridged or spiro-linked.
$R^3$, $R^6$, $R^7$, and $R^8$) are independently selected from H, (C$_1$-C$_{100}$)alkyl, (C$_1$-C$_{100}$)heteroalkyl, (C$_1$-C$_{100}$)alkoxy, ($C_1$-$C_{100}$)alkenyl, ($C_1$-$C_{100}$)alkynyl, aryl, heteroaryl, halo, —OR', —OC(O)R', —NR'R", —SR', —OC(O)NR'R", —NR"C(O)R', —NR"C(O)OR', —NR'C(O)NR"R'", and —SO$_2$H, where R', R" and R'" are independently selected from H, ($C_1$-$C_8$)alkyl, ($C_1$-$C_8$)heteroalkyl, aryl, and heteroaryl, and where the aryl and heteroaryl groups may be unsubstituted or substituted.

$R^4$, $R^5$, $R^8$, and $R^9$ are independently selected from H, ($C_1$-$C_{100}$)alkyl, ($C_1$-$C_{100}$)heteroalkyl, ($C_1$-$C_{100}$)alkoxy, ($C_1$-$C_{100}$)alkenyl, ($C_1$-$C_{100}$)alkynyl, aryl and heteroaryl.

$R^{11}$, $R^{12}$, $R^{13}$ and $R^{14}$ independently selected from H, ($C_1$-$C_{100}$)alkyl, ($C_1$-$C_{100}$)heteroalkyl, ($C_1$-$C_{100}$)alkoxy, ($C_1$-$C_{100}$)alkenyl, ($C_1$-$C_{100}$)alkynyl, aryl, heteroaryl, halo, —OR', —OSO$_2$R', —OC(O)R', —NR'R", —SR', —R', —CN, —NO$_2$, —CO$_2$R', —CONR'R", —C(O)R', —SO$_2$R', —SO$_2$NR'R", —N$_3$, —CH(Ph)$_2$, perfluoro($C_1$-$C_4$)alkoxy, perfluoro($C_1$-$C_4$)alkyl, —P(O)(OR$^{15}$)(OR$^{16}$) and —R$^{21}$-R$^{22}$, where R' and R" are independently selected from H, ($C_1$-$C_{20}$)alkyl, perfluoro($C_1$-$C_4$)alkyl, perfluoro($C_1$-$C_4$)heteroalkyl, aryl and heteroaryl, and where the aryl and heteroaryl groups may be unsubstituted or substituted.

$R^3$, $R^4$, $R^5$, $R^6$, $R^7$, $R^8$, $R^9$, $R^{10}$, $R^{11}$, $R^{12}$, $R^{13}$ and $R^{14}$ may form one or more 4- to 7-member ring systems by bridging between one or more of $R^3$, $R^4$, $R^5$, $R^6$, $R^7$, $R^8$, $R^9$, $R^{10}$, $R^{11}$, $R^{12}$, $R^{13}$ and $R^{14}$. The bridging may be between one or more of: $R^3$ with $R^4$, $R^4$ with $R^5$, $R^5$ with $R^6$, $R^7$ with $R^8$, $R^8$ with $R^9$, $R^9$ with $R^{10}$, $R^{11}$ with $R^{12}$, $R^{12}$ with $R^{13}$, and $R^{13}$ with $R^{14}$. The rings may be fused, bridged or Spiro-linked to other 4- to 7-member ring systems, each with 0 to 3 double bonds and optionally containing heteroatoms.

$R^{15}$ is selected from H—, NH$_2$(CH)$_4$—, NH$_2$(CH$_2$)$_5$—, CF$_3$C(O)NR'(CH$_2$)$_4$—, CF$_3$C(O)NR'(CH$_2$)$_5$, (CH$_3$)$_3$COC(O)NR'(CH$_2$)$_4$—, (CH$_3$)$_3$COC(O)NR'(CH$_2$)$_5$—, tert-butyl, methyl, and aryl, wherein R' is selected from H— and ($C_1$-$C_5$)alkyl.

$R^{16}$ is either the same as $R^{15}$ or the same as $R^{22}$.

$R^{21}$ is a divalent group selected from alkylene, alkenylene, alkynylene, arylene, heteroalkylene, heteroalkenylene, heteroalkynylene, and heteroarylene, where one free valence connects to one of the $R^{11}$-$R^{14}$ aromatic carbons of Structure XII and the other free valence connects to $R^{22}$.

Q is —N(R$^{23}$)(R$^{24}$) or OR$^{25}$.

$R^{22}$, $R^{23}$, and $R^{24}$ are independently selected from ($C_1$-$C_{100}$)alkyl, aryl, ($C_1$-$C_{100}$)heteroalkyl, HOSO$_2$($C_1$-$C_{100}$)alkyl, heteroaryl or a combination thereof. $R^{23}$ and $R^{24}$ may be bridged to form a saturated ring with 0 to 3 heteroatoms.

$R^{25}$ is H or is the same as $R^{23}$.

X$^-$ is an optional anionic counter ion, such as Cl$^-$, ClO$_4^-$, CH$_3$COO$^-$ and the like.

In carborhodamine compounds of this disclosure summarized in structure XII, there is the proviso that at least one of the hydrocarbon hydrogens in any of $R^1$-$R^{16}$, $R^{21}$-$R^{25}$ is independently replaced with —C(O)R$^{17}$ or —OR$^{18}$, where $R^{17}$ is selected from HO—, alkoxy, a leaving group or a nitrogen atom of an alkylamino group in an alkylamine-modified oligonucleotide and $R^{18}$ is selected from H—, dimethoxytrityl, NCCH$_2$CH$_2$OP(N(i-Pr)$_2$)—, wherein i-Pr is isopropyl, a phosphorus atom of a phosphate group in an oligonucleotide, or —C(O)—R$^{19}$—C(O)R$^{20}$—, where $R^{19}$ is a divalent group selected from ($C_1$-$C_{20}$)alkylene, arylene, (C1-$C_{20}$)heteroalkylene, heteroarylene or a combination thereof and $R^{20}$ is selected from HO—, a leaving group or a nitrogen atom of an amino group in an amine-modified solid support.

Preferred embodiments include the carborhodamine compounds of structure XII described above, where one of $R^{11}$, $R^{12}$, $R^{13}$ and $R^{14}$ is —P(O)(OR$^{15}$)(OR$^{16}$) and one or more hydrocarbon hydrogens in $R^{16}$ is replaced with —C(O)R$^{17}$ or —OR$^{18}$. Additional preferred embodiments include the carborhodamine compounds of structure XII above, wherein one of $R^{11}$, $R^{12}$, $R^{13}$ and $R^{14}$ is —R$^{21}$-R$^{22}$ and one or more hydrocarbon hydrogens in $R^{22}$ is replaced with —C(O)R$^{17}$ or —OR$^{18}$. Further preferred embodiments include the carborhodamine compounds of structure XII above, wherein Q is —N(R$^{23}$)(R$^{24}$) and one or more hydrocarbon hydrogens in $R^{23}$ or $R^{24}$ is replaced with —C(O)R$^{17}$ or —OR$^{18}$.

Preferred embodiments of the present disclosure also relate to a process for the preparation of carborhodamine compounds of structure I below:

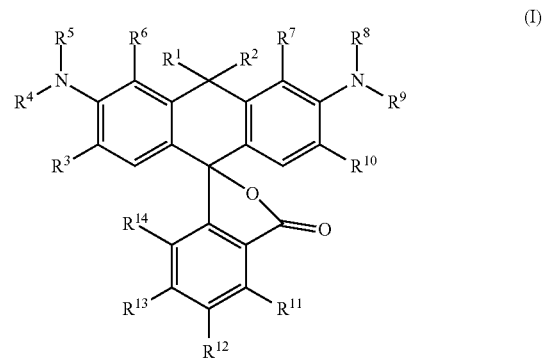

(I)

comprising of reacting one compound of general structure II

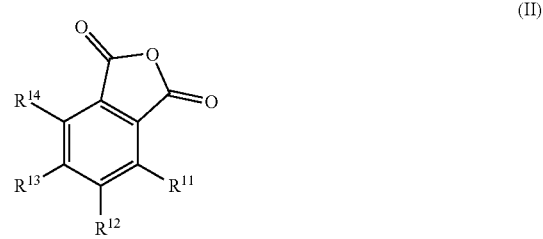

(II)

with a compound of general structure III

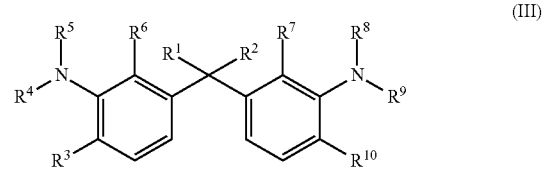

(III)

in a reaction mixture that includes a suitable solvent such as 1,2-dichloroethane and a suitable Lewis acid such as aluminum chloride, wherein:
  $R^1$ and $R^2$ are independently selected from ($C_1$-$C_{20}$)alkyl, ($C_1$-$C_{20}$)heteroalkyl or taken together form a ring structure of one or more rings. When more than one ring is present, the rings are fused, bridged or spiro-linked. Optionally, one or more hydrocarbon hydrogens of the alkyl, heteroalkyl or the ring structure is replaced with a linking group.

$R^3$, $R^6$, $R^7$, and $R^{10}$ are independently selected from H, unsubstituted or substituted $(C_1-C_{20})$alkyl, $(C_1-C_{20})$ alkoxy, $(C_1-C_{20})$alkenyl, $(C_1-C_{20})$alkynyl, aryl, heteroaryl, a linking group, halo, —OR', —OC(O)R', —NR'R", —SR', —OC(O) NR'R", —NR"C(O)R', —NR"C(O)OR', —NR'C(O)NR"R''', and —SO$_2$H, where R', R" and R''' are independently selected from H, $(C_1-C_8)$alkyl, $(C_1-C_8)$heteroalkyl, aryl, heteroaryl and a linking group, and where the aryl and heteroaryl may be unsubstituted or substituted.

$R^4$, $R^5$, $R^8$ and $R^9$ are independently selected from H, $(C_1-C_{20})$alkyl, $(C_1-C_{20})$alkoxy, $(C_1-C_{20})$alkenyl, $(C_1-C_{20})$alkynyl, aryl, heteroaryl, and a linking group, where the $(C_1-C_{20})$alkyl, aryl, and heteroaryl groups may be unsubstituted or substituted.

$R^3$, $R^4$, $R^5$, $R^6$, $R^7$, $R^8$, $R^9$, and $R^{10}$ may form one or more 4- to 7-member ring systems by bridging between one or more of $R^3$, $R^4$, $R^5$, $R^6$, $R^7$, $R^8$, $R^9$, and $R^{10}$. The bridging may be between one or more of: $R^3$ with $R^4$, $R^4$ with $R^5$, $R^5$ with $R^6$, $R^7$ with $R^8$, $R^8$ with $R^9$, and $R^9$ with $R^{10}$, which are, optionally, fused, bridged or spiro-linked to other 4- to 7-member ring systems, each with 0 to 3 double bonds and optionally containing heteroatoms.

$R^{11}$, $R^{12}$, $R^{13}$ and $R^{14}$ are independently selected from H, $(C_1-C_{20})$alkyl, $(C1-C20)$alkoxy, $(C_1-C_{20})$alkenyl, $(C_1-C_{20})$alkynyl, aryl, heteroaryl, a linking group, halo, —OR', —OSO$_2$R', —OC(O)R', —NR'R", —SR', —R', —CN, —NO$_2$, —CO$_2$R', —CONR'R", —C(O)R', —SO$_2$R', —SO$_2$NR'R", —N$_3$, —CH(Ph)$_2$, perfluoro $(C_1-C_4)$alkoxy, and perfluoro$(C1-C_4)$alkyl, where Ph is phenyl, where R' and R" are independently selected from H, $(C_1-C_{20})$alkyl perfluoro$(C_1-C_4)$alkyl, perfluoro $(C_1-C_4)$heteroalkyl, aryl and heteroaryl, where the aryl and heteroaryl groups may be unsubstituted or substituted. Optionally, one or more 4- to 7-member ring systems are formed by bridging between one or more of $R^{11}$ with $R^{12}$, $R^{12}$ with $R^{13}$, and $R^{13}$ with $R^{14}$, which are, optionally, fused, bridged or spiro-linked to other 4- to 7-member ring systems, each with 0 to 3 double bonds and optionally containing heteroatoms.

A linking group is selected from $(C_1-C_{20})$alkyl, aryl, $(C_1-C_{20})$heteroalkyl, heteroaryl and combinations thereof wherein at least one of the hydrocarbon hydrogens is replaced with a protected or unprotected carboxyl or a hydroxyl group, and wherein protecting groups on any protected carboxyl or hydroxyl group are selected from an amide, an ester or an ether group.

Oligonucleotide conjugates of this disclosure can be synthesized in a variety of ways. One way is to use the activated derivatives of carboxyl-substituted carborhodamines wherein the carboxyl group is a one of the $R^{11}$-$R^{14}$ substituent in Structure I or part of a linking group. Typically, the carboxyl group is converted into an activated ester with a good leaving group. One such leaving group is the pentafluorophenyloxy group exemplified in this disclosure. Other examples of suitable leaving groups are N-succinimidyloxy and p-nitrophenyloxy groups as practiced in Hermanson (1996), incorporated by reference.

These derivatives can be conveniently reacted with oligonucleotides bearing primary or secondary aliphatic amino groups to form covalent amide bonds between oligonucleotides and activated esters of the disclosure. Description and examples of suitable procedures for such conjugation reactions can be found, for instance, in Kutyavin (2003) and Lukhtanov (1995).

Figure 7A:
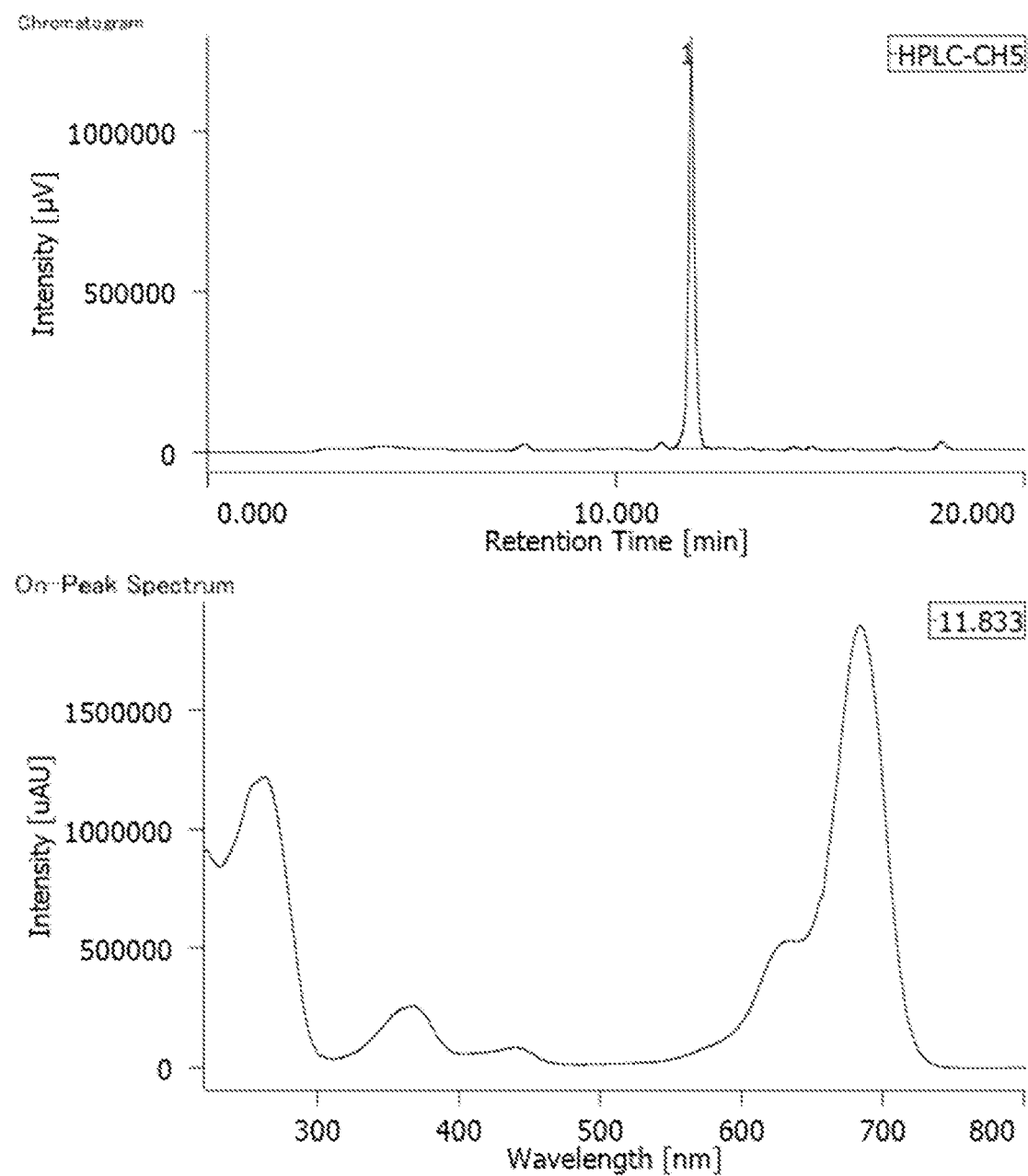
FIG. 7A shows an example of a reverse phase HPLC analysis, UV-VIS spectrum for a $T_8$-carborhodamine conjugate synthesized using an exemplary polystyrene support.
Figure 7B:
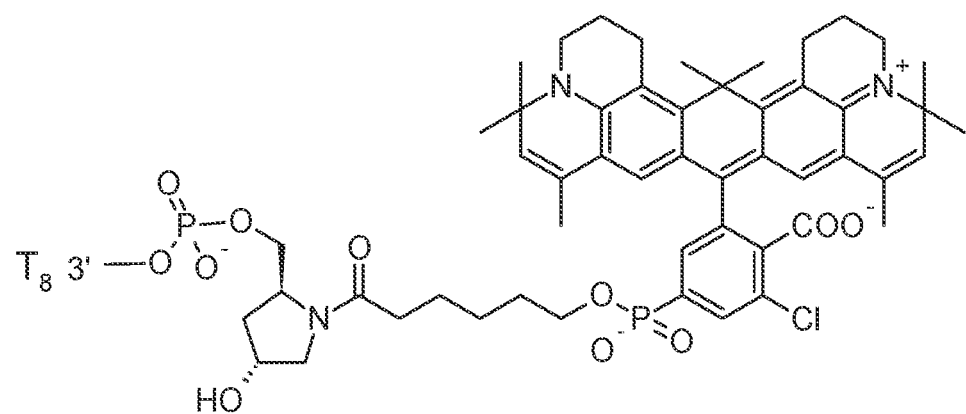
FIG. 7B shows the structure of a $T_8$-carborhodamine conjugate synthesized using an exemplary polystyrene support.

Activated esters can also be used to react with linker moieties. Those linker moieties may be mono- or poly functional and contain various functional groups such as amine, hydroxyl, DMT-protected hydroxyl, etc. One particular type of poly functional linker is hydroxyprolinol (see FIG. 4), a trifunctional reagent that has an amino, a primary and a secondary hydroxyl group. The hydroxyprolinol linker, as well as examples of other trifunctional reagents having an amino, primary and a secondary hydroxyl group, are described in U.S. Pat. No. 5,512,667. The primary hydroxyl group of the hydroxyprolinol linker, in this example, is protected with a dimethoxytrityl group whereas the secondary hydroxyl and amino groups are available for further modifications. One such modification is the introduction of a succinate linker followed by activation of free carboxyl group and coupling to a solid support (see FIG. 4). The solid support used in synthetic scheme shown in FIG. 4 is a highly cross-linked porous styrene-divinylbenzene copolymer further aminomethylated to enable the surface chemistry (Applied Biosystems, PN 360865C). Another example of solid support is Controlled Pore Glass (CPG) (Glen Research, Sterling, VA), which is commercially available in different pore sizes and with long chain alkylamine extension for more efficient phosphoramidite coupling. The DMT-protected hydroxyl group of the carborhodamine-modified Polystyrene Support in FIG. 4 is the starting point of oligonucleotide synthesis. An example of analytical reverse phase HPLC of a $T_8$ carborhodamine conjugate is shown in FIG. 7A. The structure of the $T_8$ carborhodamine conjugate is shown in FIG. 7B. This example demonstrates that such conjugates can be synthesized using the Polystyrene support in excellent yield and be readily purified by reverse phase chromatography.

Figure 6:
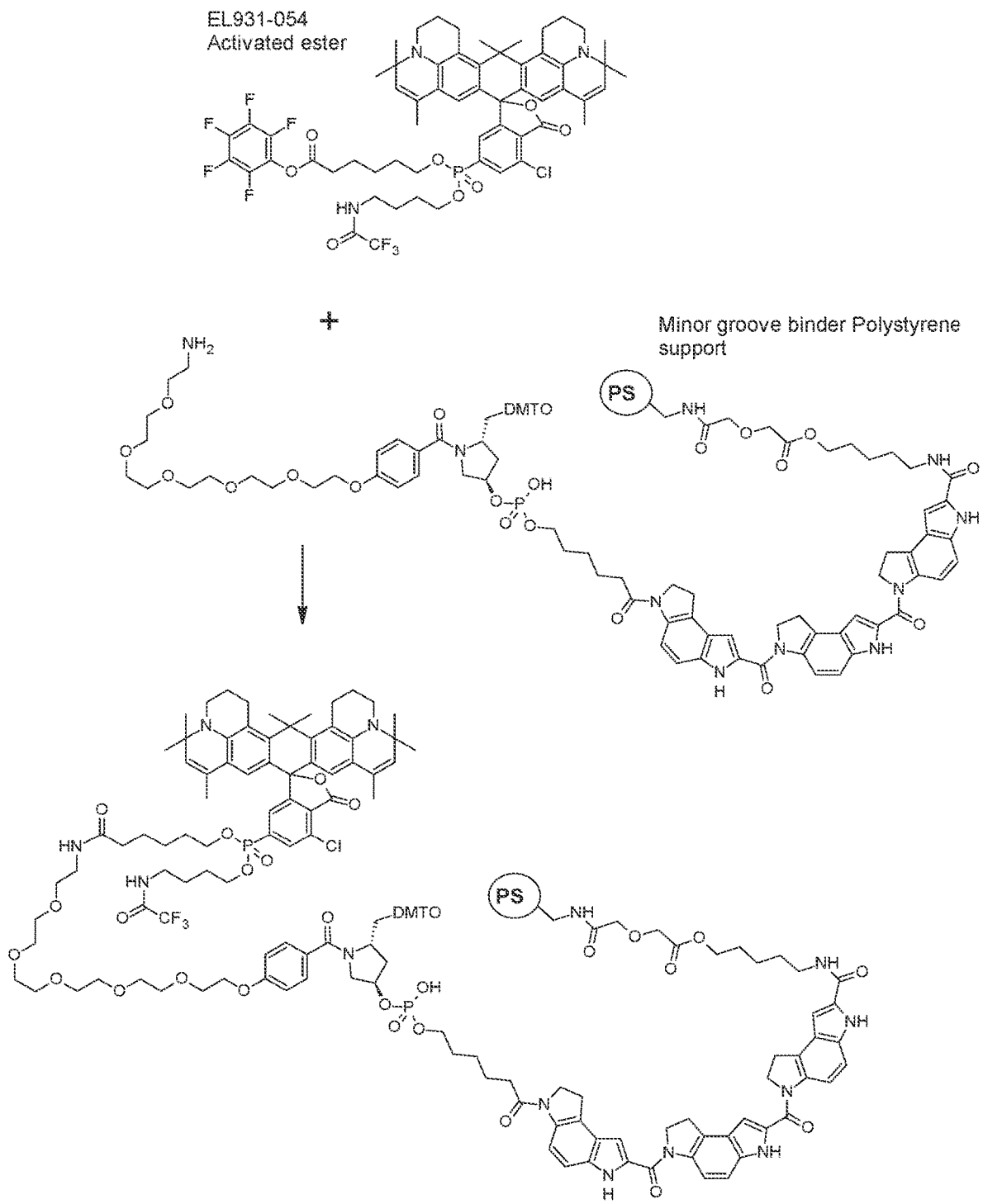
FIG. 6 shows a synthetic scheme for the preparation of an exemplary solid support.
Figure 8A:
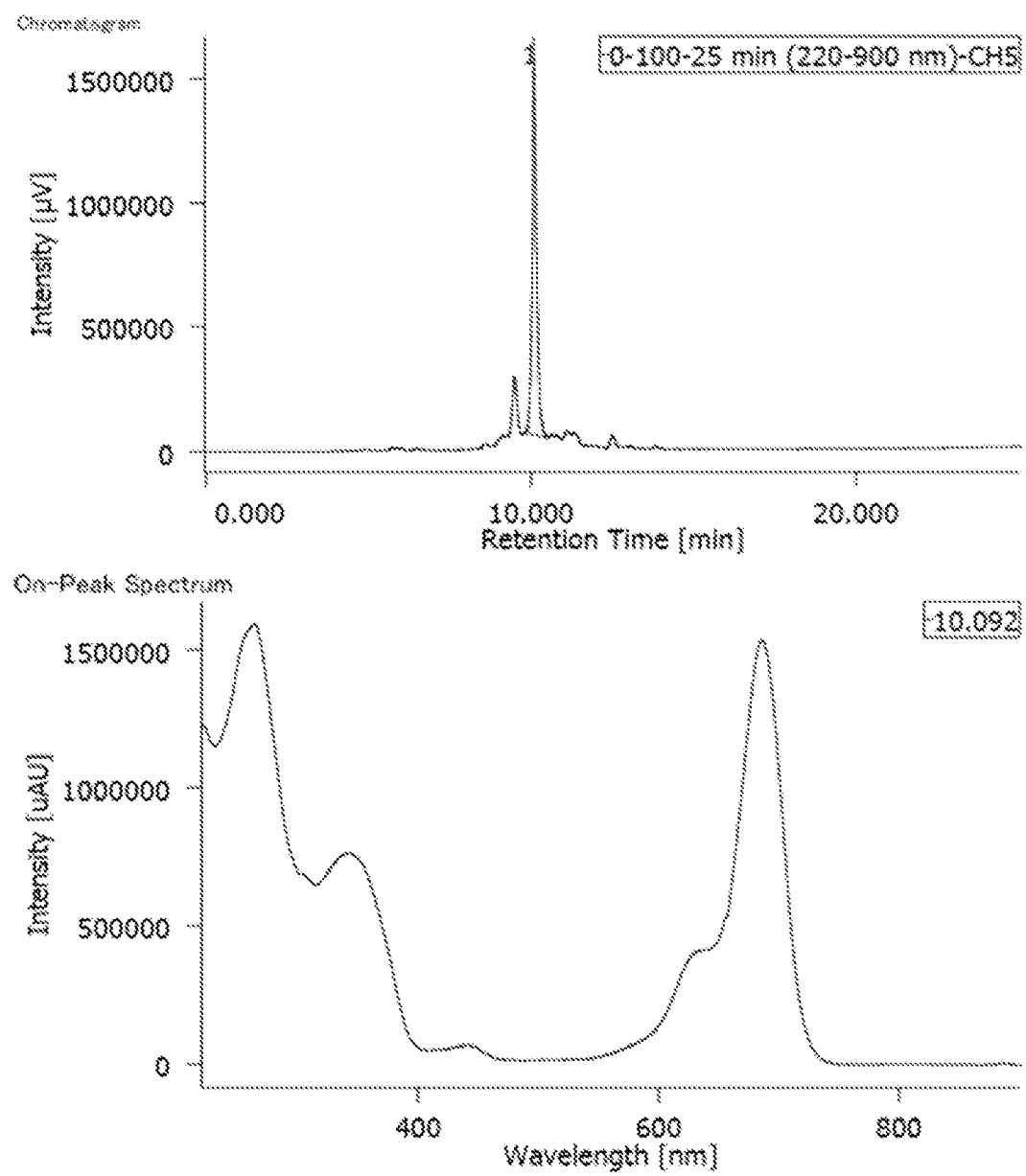
FIG. 8A shows an example of a reverse phase HPLC analysis, UV-VIS spectrum for a $T_8$-carborhodamine-MGB conjugate synthesized using an exemplary polystyrene support.
Figure 8B:
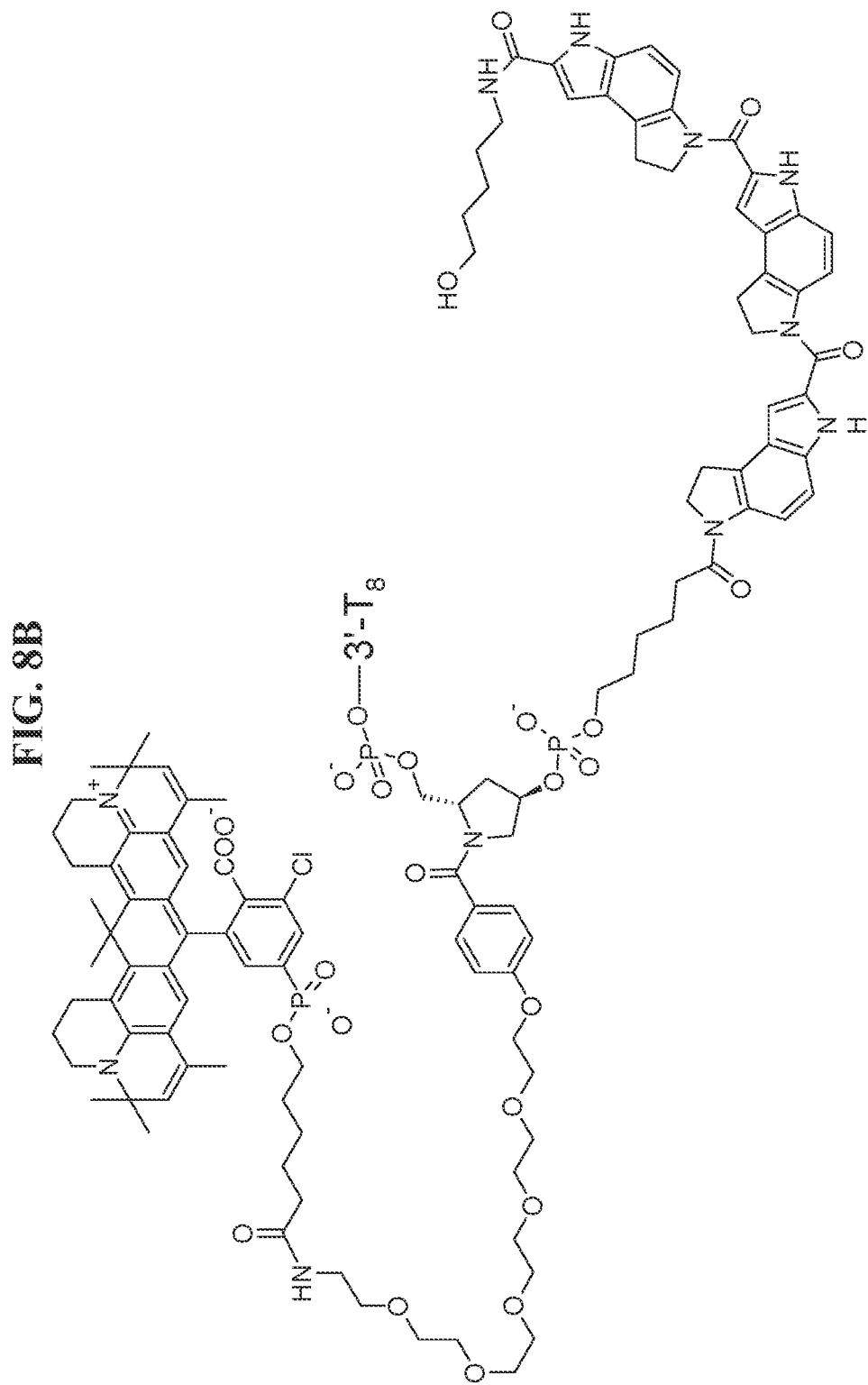
FIG. 8B shows the structure of a $T_8$-carborhodamine-MGB conjugate synthesized using an exemplary polystyrene support.

Another example of a more complicated multifunctional linker is shown in FIG. 6. In this example the intermediates disclosed in U.S. Pat. No. 7,759,126 are used to assemble the Minor Groove Binder (MGB) Polystyrene support, which has the MGB moiety covalently attached to aminomethyl polystyrene support via a cleavable diglycolate linker, a DMT-containing hydroxyprolinol linker coupled to the MGB group via a phosphate group and an amino group coupled to the hydroxyprolinol group via a hexaethylene glycol spacer. The free amino group is used to attach a carborhodamine dye using an activated carboxyl group of the dye giving a Minor Groove Binder-carborhodamine solid support. An analytical C18 HPLC trace of a $T_8$ oligonucleotide synthesis using this solid support is shown in FIG. 8A demonstrating that the MGB-carborhodamine-oligonucleotide conjugates prepared using the solid support can be synthesized in high yield and be purified by reverse phase chromatography. FIG. 8B shows the structure of the $T_8$-carborhodamine-MGB conjugate synthesized using an exemplary polystyrene support. The solid support is particularly useful for the preparation of MGB Pleiades oligonucleotide probes (Lukhtanov (2007)), which comprise a 5'-MGB-fluorophore and a 3'-quencher moieties.

Figure 9A:
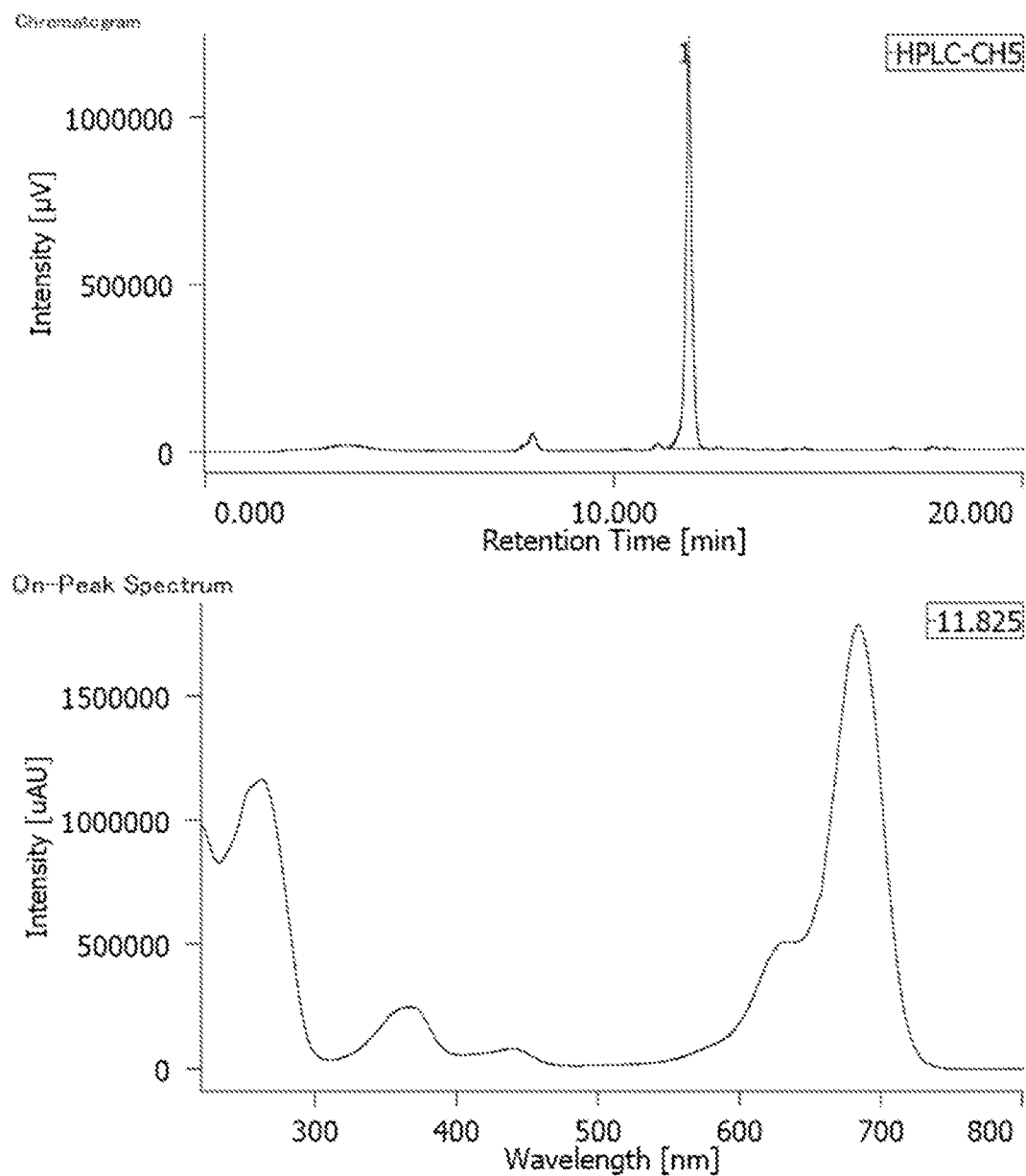
FIG. 9A shows an example of a reverse phase HPLC analysis, UV-VIS spectrum for a T8-carborhodamine conjugate synthesized using an exemplary phosphoramidite.
Figure 9B:
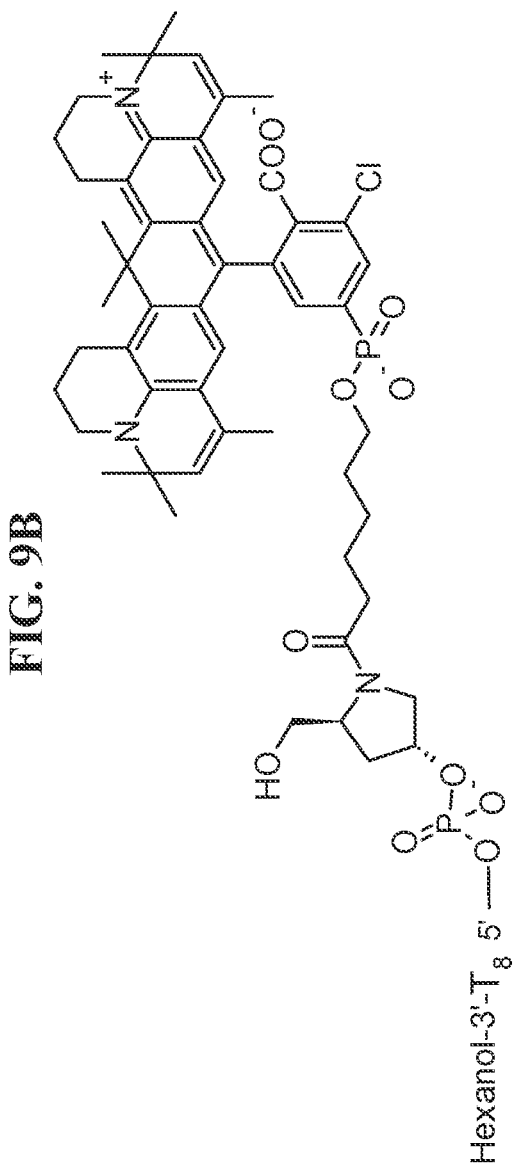
FIG. 9B shows the structure of a T8-carborhodamine conjugate synthesized using an exemplary phosphoramidite.

2-Cyanoethyl N,N-diisopropylphosphoramidite chemistry is another way to prepare oligonucleotides bearing the compounds of the disclosure. One example of a suitable phosphoramidite reagent is shown in FIG. 4. In this example the free hydroxyl group of the hydroxyprolinol-modified carborhodamine is reacted with 2-cyanoethyl N,N,N',N'-tetraisopropylphosphordiamidite to give the desired phosphoramidite. An analytical C18 HPLC trace of a $T_8$ oligonucleotide conjugate (FIG. 9A) synthesized using this phosphoramidite demonstrated high coupling efficiency and clean deprotection. The structure of the T8 oligonucleotide conjugate synthesized using this phosphoramidite is shown in FIG. 9B. The phosphoramidite shown in FIG. 4 is suitable for both terminal and internal dye incorporation. Such phosphoramidites can be used for the preparation of TaqMan or MGB Pleiades oligonucleotide probes, which require a 5'- or an internal fluorophore labeling, respectively.

Figure 10A:
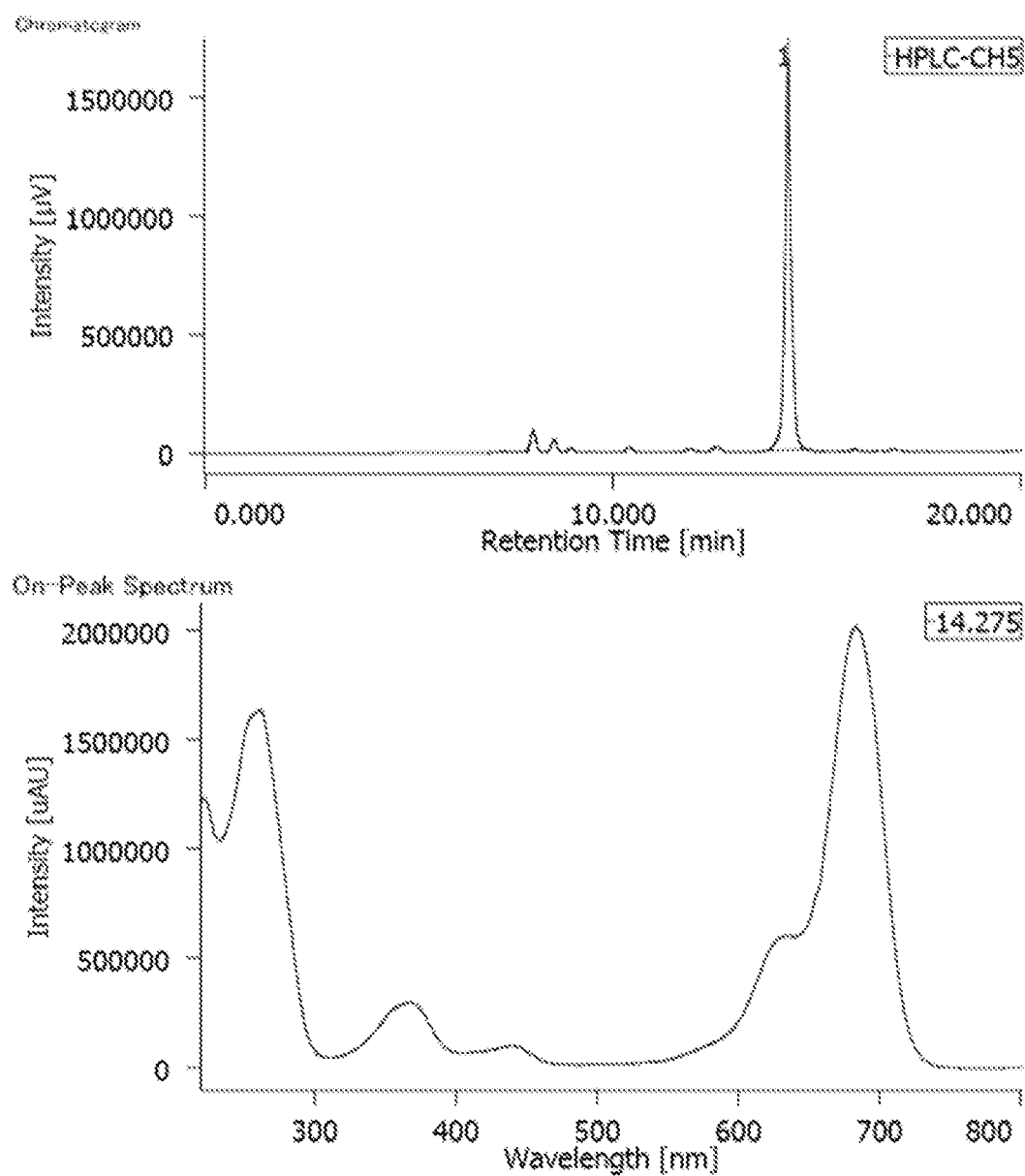
FIG. 10A shows an example of a reverse phase HPLC analysis, UV-VIS spectrum for a T8-carborhodamine conjugate synthesized using an exemplary phosphoramidite.
Figure 10B:
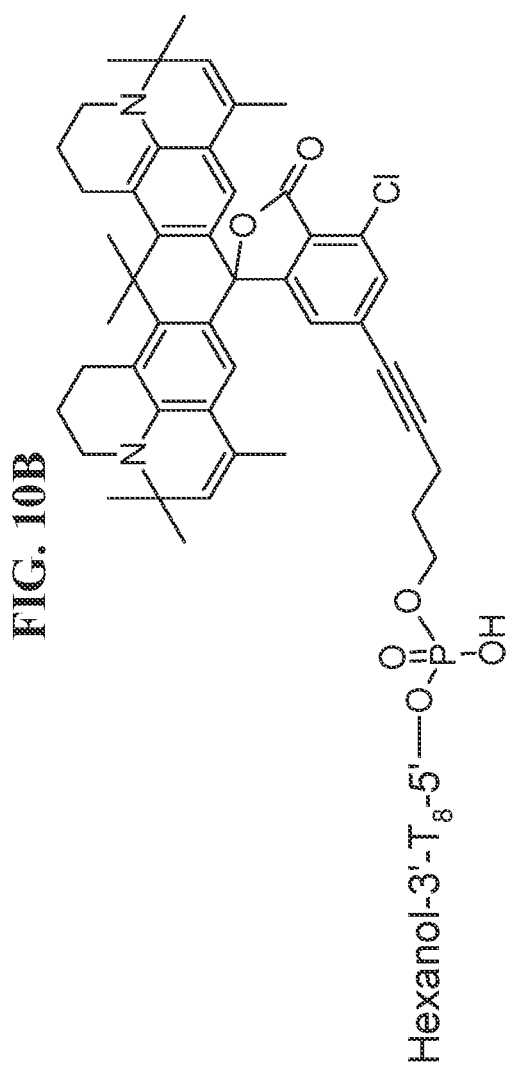
FIG. 10B shows the structure of a T8-carborhodamine conjugate synthesized using an exemplary phosphoramidite.

Another example of phosphoramidite chemistry is shown in FIG. 5. In this example, it is a terminal phosphoramidite, which is suitable for 5'- or 3'-oligonucleotide coupling only. An analytical C18 HPLC trace shown in FIG. 10A confirms high coupling efficiency of the phosphoramidite, clean deprotection and lack of side products. The structure the structure of the $T_8$-carborhodamine conjugate synthesized using this exemplary phosphoramidite is shown in FIG. 10B. This phosphoramidite is also useful for the preparation of TaqMan probes or MGB TaqMan probes.

Preferred embodiments described herein include an oligonucleotide conjugate comprising the carborhodamine compounds described herein, an oligonucleotide, and a quencher. The oligonucleotide conjugate may further comprise a minor groove binder.

Carborhodamine-oligonucleotide conjugates prepared according to the disclosed methods are useful for various fluorescence-based application. One preferred group of embodiments includes target detection in nucleic acid amplification techniques such as polymerase chain reaction (PCR) or isothermal amplification.

One particular embodiment of this group is a method for detecting a target nucleic acid sequence in a sample, comprising a step of contacting the sample with embodiments of the oligonucleotide conjugates described herein that include the carborhodamine compounds, wherein the oligonucleotide has a nucleic acid sequence at least partially complementary to the target nucleic acid sequence, and wherein the oligonucleotide conjugate includes a quencher. The oligonucleotide conjugate may further comprise a minor groove binder. In a further step, a fluorescent signal is detected from the oligonucleotide conjugate upon hybridization to the target nucleic acid sequence. Further preferred embodiments also include the step of amplifying the target nucleic acid sequence. In some preferred embodiments the oligonucleotide conjugate is a primer or a probe. Further preferred embodiments include contacting the sample and the oligonucleotide conjugate with a polymerase enzyme comprising 5'-nuclease activity, wherein the fluorescence signal is generated by the polymerase enzyme. Additional embodiments comprise amplifying the target nucleic acid sequence.

Figure 12:
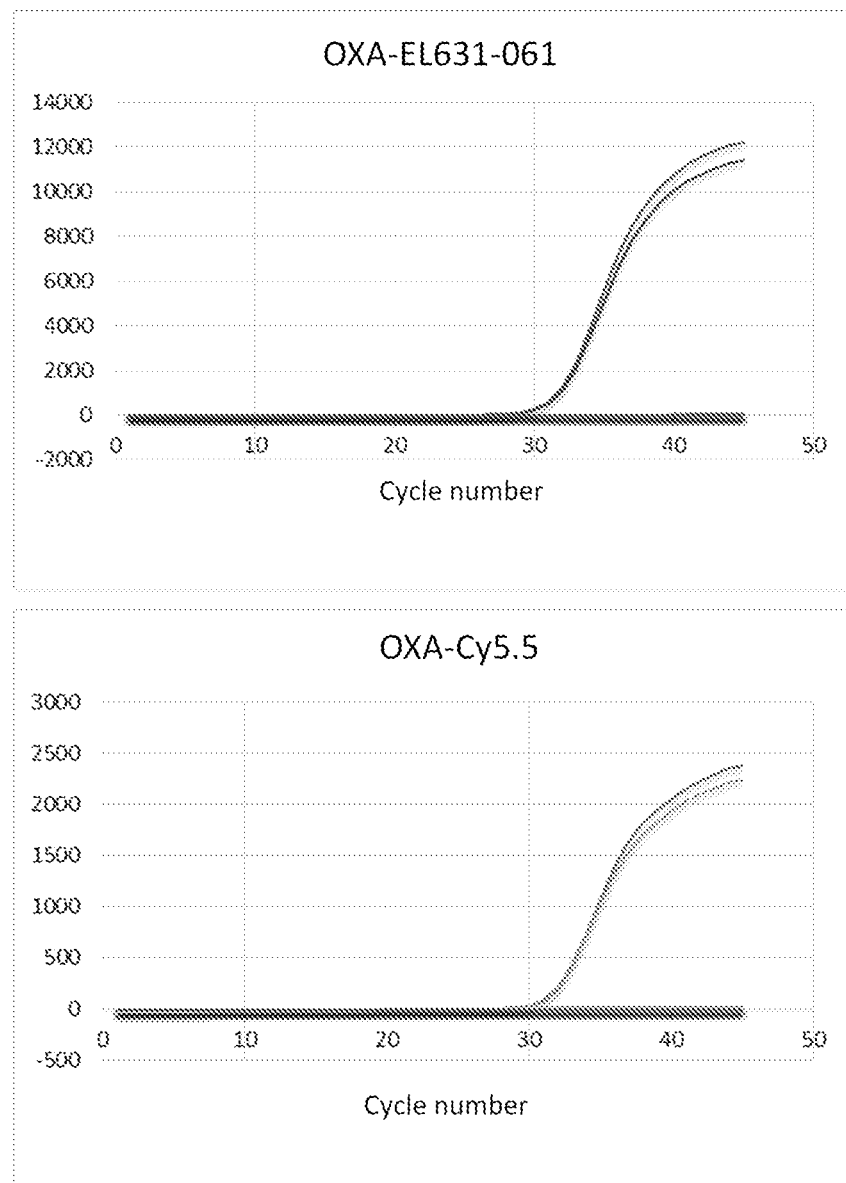
FIG. 12 shows an example of a real-time PCR amplification of a DNA target using 5'-carborhodamine-labeled MGB TaqMan probes.

In one embodiment described herein, an oligonucleotide conjugate comprises a 5'-carborhodamine of this disclosure, a 3'-quencher and, optionally, a 3'-minor groove binder and to yield oligonucleotides of general Structure XIII:

5'-FI-ODN-3'-Q-MGB                Structure XIII wherein FI is a carborhodamine and ODN is an oligonucleotide and Q is a quencher and MGB is an optional minor groove binder. Conjugates of general Structure XIII are particularly useful as DNA probes for fluorescence-based real-time and end point PCR applications that rely on the 5'-exonuclease activity of DNA polymerase for fluorophore cleavage, also known as the TaqMan technology. Example of a TaqMan PCR application using a conjugate of Structure XIII is shown in FIG. 12. In this example, the same DNA probe (OXA) was prepared either with the Cy5.5 dye or the new EL931-061 dye of this disclosure. The real-time PCR amplification signal of the probe with the new dye is approximately 5 times greater compared to the same probe with the Cy5.5 dye. The signal increase offers an improvement in assay sensitivity.

In other preferred embodiment the oligonucleotide conjugates comprise a 5' minor groove binder, 5' quencher and a 3' fluorophore as represented by Structure XIV:

5'-MGB-Q-ODN-3'-FI                Structure XIV wherein Q, MGB and FI are as previously defined. Oligonucleotide conjugates of general structure XIV are useful as DNA probes for fluorogenic probes whose fluorescence signal is generated due to the hybridization with a target. The 5' MGB moiety prevents the 5' exonuclease probe degradation.

Figure 13:
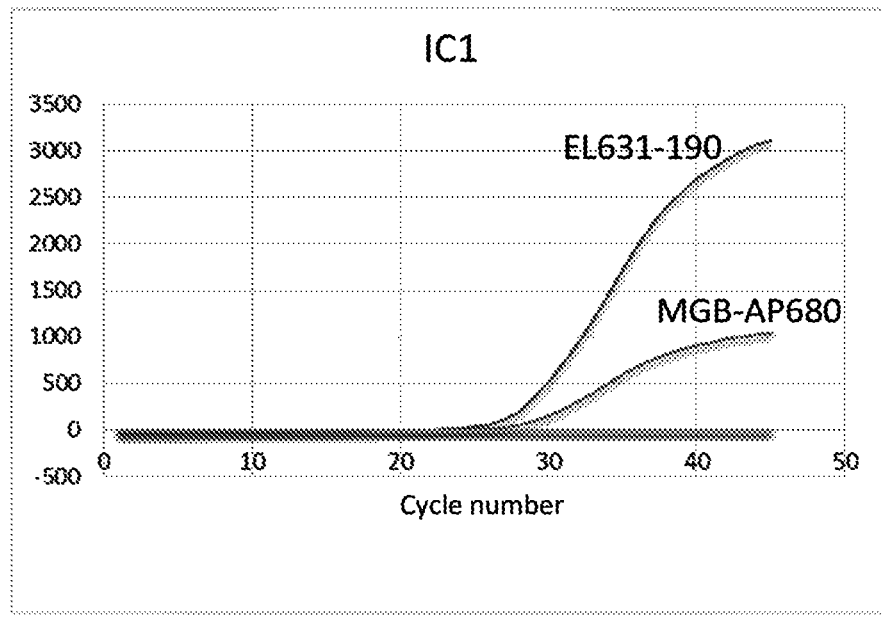
FIG. 13 shows an example of a real-time PCR amplification of a DNA target using 5'-carborhodamine-labeled MGB Pleiades probes.

In additional preferred embodiments the oligonucleoptide conjugates comprise a 5'-MGB and a 5'-fluorophore positioned adjacent to each other and 3' quencher as represented by general Structure XV:

5'-MGB—FI-ODN-3'-Q Structure XV wherein Q, MGB and FI are as previously defined. Such oligonucleotides are useful as hybridization-triggered fluorogenic probes and primers as illustrated in FIG. 13. In this example, both real-time PCR signal increase and assay sensitivity are observed due to the presence of a new dye of this disclosure.

In additional preferred embodiments, the oligonucleotide-carborhodamine conjugates could be used in digital PCR and arrays (U.S. Pat. Nos. 9,328,384 and 7,759,126 incorporated by reference).

Although not illustrated in Structures XIII-XXV, in some preferred embodiments the carborhodamine moiety of this disclosure is covalently attached to an internal position of an oligonucleotide, for example to an amine-tailed nucleobase.

In further preferred embodiments, the carborhodamine-oligonucleotide conjugates are used to differentiate single nucleotide polymorphisms as taught in U.S. Pat. No. 6,312, 894 and, 7,718,374 incorporated by reference. In a related embodiment, different targets are detected using a melting curve analysis (Hymas and Hillyard, 2009 incorporated by reference).

Other applications, not specifically described in this specification but known in the art (for example Didenko (2001), Kim (2008)), are also potential applications of the new oligonucleotide conjugates of the disclosure.

EXAMPLES

The following examples illustrate the preparation of compounds of general Structure III.

Example 1. Synthesis of 1,1'-propane-2,2-diylbis(4-bromobenzene)

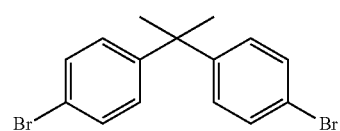 [SMILES: CC(C)(c1ccc(Br)cc1)c1ccc(Br)cc1]

A 3 neck 500 mL round bottom flask equipped with a thermometer, addition funnel topped with a drying tube was charged with 2,2-diphenylpropane (25.21 g, 128.4 mmol), dichloromethane (50 mL), iron powder (0.43 g), iodine (approx. 75 mg) and magnetic stir bar. The flask was cooled to 3-4° C. using an ice/water bath. Bromine (43.6 g, 272.5 mmol) was added dropwise with stirring over the course of 3 hrs maintaining the reaction temperature at 3-4° C. After being stirred for another 30 min the reaction was diluted with dichloromethane and washed with dilute sodium hydrogen sulfite, 1 M HCl, saturated $NaHCO_3$ and dried over $Na_2SO_4$. The crude product obtained after solvent evaporation was re-crystallized from hexane to yield 38.25 g (84%) of 1,1'-propane-2,2-diylbis(4-bromobenzene) as a light yellow crystalline solid. $^1$H NMR (300 MHz, $CDCl_3$): δ 7.38 (d, J=8.7 Hz, 4H), 7.07 (d, J=8.7 Hz, 4H), 1.63 (s, 6H).

Example 2. Synthesis of 1,1'-propane-2,2-diylbis(4-bromo-3-nitrobenzene)

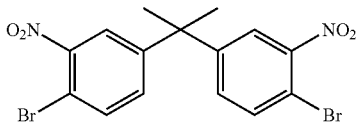 [SMILES: CC(C)(c1ccc(Br)c([N+](=O)[O-])c1)c1ccc(Br)c([N+](=O)[O-])c1]

A cold (approx. 5-10° C.) mixture of conc. $H_2SO_4$ (50 mL) and 70% $HNO_3$ (44 mL) was added via an addition funnel over the course of 10 min to a stirred solution of 1,1'-propane-2,2-diylbis(4-bromobenzene) (34.4, 97.15 mmol) in dichloromethane (180 mL) maintaining the temperature at 0-5° C. The biphasic mixture was allowed to warm to room temperature, stirred for another 2 hrs and then diluted with cold water. The dichloromethane layer was separated, washed with saturated $NaHCO_3$ and dried over $Na_2SO_4$. Crude product obtained after the solvent evaporation was washed with methanol and re-crystallized from ethyl acetate to afford 35.8 g (83%) of 1,1'-propane-2,2-diylbis(4-bromo-3-nitrobenzene) as an off white solid. $^1$H NMR (300 MHz, $CDCl_3$): δ 7.74 (d, J=2.4 Hz, 2H), 7.66 (d, J=8.4 Hz, 2H), 7.20 (dd, $J_1$=8.4 Hz, $J_2$=2.4 Hz, 2H), 1.73 (s, 6H).

Example 3. Synthesis of 4,4'-propane-2,2-diylbis(2-nitrobiphenyl)

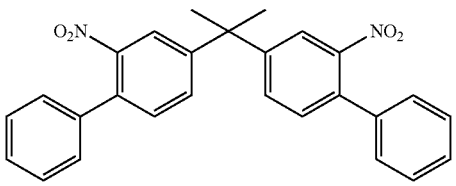 [SMILES: CC(C)(c1ccc(-c2ccccc2)c([N+](=O)[O-])c1)c1ccc(-c2ccccc2)c([N+](=O)[O-])c1]

A solution of 1,1'-propane-2,2-diylbis(4-bromo-3-nitrobenzene) (3.3 g, 7.4 mmol) and phenylboronic acid (2.35 g, 19.3 mmol) in 1,2-dimethoxyethane (90 mL) was added a solution of $K_2CO_3$ (5.6 g) in water (34 mL). After being degassed under reduced pressure for approx. 5 min the reaction flask was backfilled with argon and treated with tetrakis(triphenylphosphine)palladium (0) (1.3 g, 1.11 mmol). The reaction was stirred at 80° C. for 15 hrs, then cooled, concentrated and partitioned between ethyl acetate and water. The organic phase was washed with brine, dried over $Na_2SO_4$ and concentrated followed by column chromatography on silica gel eluting with dichloromethane to afford 2.83 g (87%) of 4,4'-propane-2,2-diylbis(2-nitrobiphenyl) as an off white solid. $^1$H NMR (300 MHz, $CDCl_3$): δ 7.79 (d, J=1.8 Hz, 2H), 7.48-7.28 (aromatic H, 14H), 1.82 (s, 6H).

Example 4. Synthesis of 4,4'-propane-2,2-diylbis(2-aminobiphenyl)

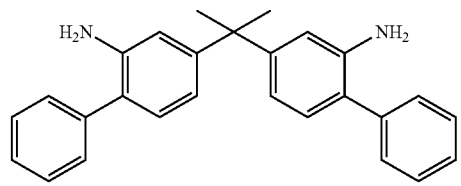 [SMILES: CC(C)(c1ccc(-c2ccccc2)c(N)c1)c1ccc(-c2ccccc2)c(N)c1]

A solution of 4,4'-propane-2,2-diylbis(2-nitrobiphenyl) (2.8 g, 6.39 mmol) in THF (40 mL) was hydrogenated at 50 psi in the presence of 10% Pd/C (0.4 g) for 40 hrs. The catalyst was removed by filtration through a pad of Celite and the filtrate concentrated to afford 2.4 g (99%) of 4,4'-propane-2,2-diylbis(2-aminobiphenyl) as an off-white solid. $^1$H NMR (300 MHz, $CDCl_3$): δ 7.48-7.28 (aromatic H, 10H), 7.06 (d, J=8.1 Hz, 2H), 6.79 (dd, $J_1$=7.9 Hz, $J_2$=2 Hz, 2H), 6.68 (d, J=1.8 Hz, 2H), 3.70 (br s, 4H), 1.69 (s, 6H).

Example 5. Synthesis of 4,4'-propane-2,2-diylbis(2-(N,N-dimethyl)aminobiphenyl)

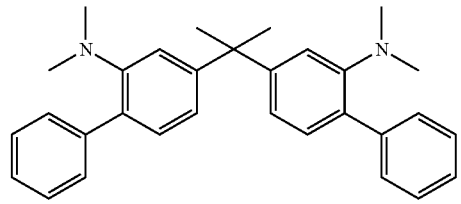 [SMILES: CN(C)c1cc(C(C)(C)c2ccc(-c3ccccc3)c(N(C)C)c2)ccc1-c1ccccc1]

To a solution of 4,4'-propane-2,2-diylbis(2-aminobiphenyl) (2.5 g, 6.6 mmol) in DMF (15 mL) was added solid $KHCO_3$ (3.6 g) followed by methyl iodide (2.2 mL, 34.5 mmol). The reaction was stirred for 20 hrs then concentrated and partitioned between water and dichloromethane. The extract was dried over $Na_2SO_4$ and concentrated. The crude product was chromatographed on silica eluting with 50% (v/v) dichloromethane in hexane followed by trituration in hexane to yield 4,4'-propane-2,2-diylbis(2-(N,N-dimethyl)aminobiphenyl) (2.2 g, 77%) as a white solid. $^1$H NMR (300 MHz, $CDCl_3$): δ 7.60 (dd, $J_1$=8.4 Hz, $J_2$=1.2 Hz, 4H), 7.37 (t, J=7.3 Hz, 4H), 7.3-7.2 (m, 2H), 7.14 (d, J=7.8 Hz, 2H), 6.97 (d, J=1.8 Hz, 2H), 6.93 (dd, $J_1$=7.8 Hz, $J_2$=2.1 Hz, 2H), 2.51 (s, 12H), 1.76 (s, 6H).

Example 6. Synthesis of 3,3'-propane-2,2-diyldianiline

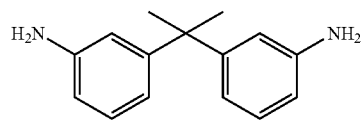 [SMILES: CC(C)(c1cccc(N)c1)c1cccc(N)c1]

A solution of 1,1'-propane-2,2-diylbis(4-bromo-3-nitrobenzene) (5.3 g, 11.9 mmol) and triethylamine (4 mL) in THF (150 mL) was hydrogenated at 50 psi in the presence of 10% Pd/C (0.5 g) for 2 hrs until no more hydrogen was being consumed. The catalyst was removed by filtration through a pad of Celite, the filtrate concentrated and the resultant residue partitioned between water and ethyl acetate. The organic phase was washed with brine, dried over $Na_2SO_4$ and concentrated to afford 2.7 g (100%) of 3,3'-propane-2,2-diyldianiline as a white solid. $^1$H NMR (300 MHz, $CDCl_3$): δ 7.06 (t, J=7.8 Hz, 2H), 6.68 (ddd, $J_1$=7.8 Hz, $J_2$=1.7 Hz, $J_3$=0.9 Hz, 2H), 6.54 (t, J=2.1 Hz, 2H), 6.51 (ddd, $J_1$=7.7 Hz, $J_2$=2.3 Hz, $J_3$=0.8 Hz, 2H), 3.58 (br s, 4H), 1.60 (s, 6H). $^{13}$C NMR (75 MHz, $CDCl_3$): δ 152.33, 146.19, 129.06, 117.48, 114.42, 112.83, 43.01, 30.88.

Example 7. Synthesis of 8,8'-propane-2,2-diylbis(2,3,6,7-tetrahydro-1H,5H-pyrido[3,2,1-ij]quinolone)

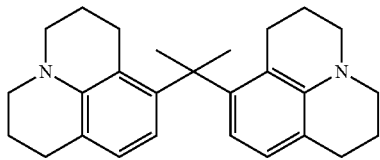 [SMILES: CC(C)(c1ccc2c3c1CCCN3CCC2)c1ccc2c3c1CCCN3CCC2]

A mixture of 3,3'-propane-2,2-diyldianiline (3.17 g, 14.0 mmol), $Na_2CO_3$ (11.7 g) and 1-bromo-3-chloropropane (24 mL) was stirred at 140° C. for 48 hrs, then cooled and partitioned between water and dichloromethane. The dichloromethane phase was dried over $Na_2SO_4$ and concentrated on a rotary evaporator (<2 mmHg) at 70° C. The resultant red oil was dissolved in DMF (12 mL) and heated at 160° C. with stirring for 8 hrs, then partitioned between saturated $NaHCO_3$ and dichloromethane. The dichloromethane phase was dried over $Na_2SO_4$ and concentrated to a red oil which was then chromatographed on silica eluting with dichloromethane followed by trituration in hexane to afford 3.4 g (63%) of 8,8'-propane-2,2-diylbis(2,3,6,7-tetrahydro-1H,5H-pyrido[3,2,1-ij]quinolone) as a white solid. $^1$H NMR (300 MHz, $CDCl_3$): δ 6.78 (skewed d, J=8.1 Hz, 2H), 6.73 (skewed d, J=8.1 Hz, 2H), 3.10 (t, J=5.7 Hz, 4H), 2.97 (t, J=6.3 Hz, 4H), 2.73 (t, J=6.4 Hz, 4H), 2.30 (br s, 2H), 1.92 (m, 6H), 1.60 (s, 6H), 1.57 (m, 4H). $^{13}$C NMR (75 MHz, $CDCl_3$): δ 145.85, 143.29, 126.57, 121.53, 119.47, 112.91, 50.82, 50.05, 43.41, 31.27, 28.01, 25.11, 22.21.

Example 8. Synthesis of 7,7'-propane-2,2-diylbis(2,2,4-trimethyl-1,2-dihydroquinoline)

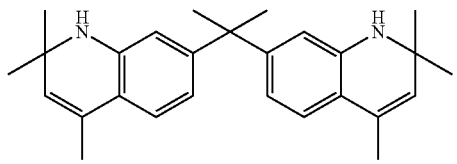

Iodine (0.67 g, 2.64 mmol) and conc. HCl were added to a solution of 3,3'-propane-2,2-diyldianiline (11.3 g, 50 mmol) in acetone (280 mL). The reaction was refluxed for 42 hrs, then cooled, neutralized with triethylamine (2 mL) and concentrated. The obtained dark oil was partitioned between dilute NaCl solution and ethyl acetate. The organic phase was washed with brine, dried over $Na_2SO_4$ and concentrated to a red oil which was then chromatographed on silica eluting with 10% (v/v) ethyl acetate in hexane followed by crystallization from hexane to afford 13.2 g (68%) of 7,7'-propane-2,2-diylbis(2,2,4-trimethyl-1,2-dihydroquinoline) as an off-white solid. $^1$H NMR (300 MHz, $CDCl_3$): δ 6.95 (d, J=7.8 Hz, 2H), 6.55 (dd, $J_1$=8.0 Hz, $J_2$=1.9 Hz, 2H), 6.28 (d, J=1.8 Hz, 2H), 5.25 (d, J=1.5 Hz, 2H), 3.58 (br s, 2H), 1.96 (d, J=1.2 Hz, 6H), 1.56 (s, 6H), 1.25 (s, 12H). $^{13}$C NMR (75 MHz, $CDCl_3$): δ 151.54, 142.95, 128.57, 127.81, 123.304, 119.25, 115.93, 112.09, 52.14, 42.75, 31.50, 30.78, 18.80.

Example 9. Synthesis of 7,7'-propane-2,2-diylbis(1,2,2,4-tetramethyl-1,2-dihydroquinoline)

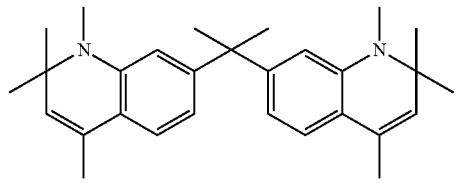

To a solution of 7,7'-propane-2,2-diylbis(2,2,4-trimethyl-1,2-dihydroquinoline) (1.4 g, 3.6 mmol) in DMF (10 mL) was added solid $KHCO_3$ (2.0 g) followed by methyl iodide (0.8 mL, 12.8 mmol). The reaction was stirred for 24 hrs then concentrated and partitioned between water and ethyl acetate. The extract was washed with brine, dried over $Na_2SO_4$ and concentrated. The resultant material was chromatographed on silica eluting with 10% (v/v) ethyl acetate in hexane to afford 1.0 g (67%) of 7,7'-propane-2,2-diylbis(1,2,2,4-tetramethyl-1,2-dihydroquinoline) as an amorphous solid. $^1$H NMR (300 MHz, $CDCl_3$): δ 6.95 (d, J=8.1 Hz, 2H), 6.57 (dd, $J_1$=8.1 Hz, $J_2$=1.8 Hz, 2H), 6.43 (d, J=1.8 Hz, 2H), 5.24 (d, J=1.2 Hz, 2H), 2.71 (s, 6H), 1.96 (d, J=1.2 Hz, 6H), 1.65 (s, 6H), 1.27 (s, 12H).

Example 10. Synthesis of 10,10'-propane-2,2-diylbis(5,5,7-trimethyl-2,3-dihydro-1H,5H-pyrido[3,2,1-ij]quinoline)

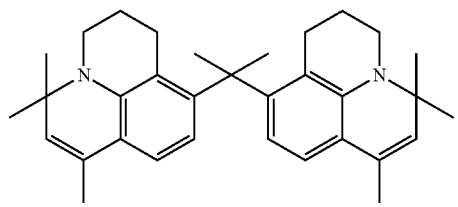

A 500 mL round bottom flask topped with a reflux condenser was charged with 7,7'-propane-2,2-diylbis(2,2,4-trimethyl-1,2-dihydroquinoline) (13.3 g, 34.4 mmol), acetonitrile (180 mL), $NaHCO_3$ (17.5 g, 205 mmol) and 1,3-diiodopropane (33.2 g, 111.6 mmol). The reaction was refluxed for 48 hrs, then cooled, concentrated and partitioned between water and dichloromethane. The dichloromethane phase was dried over $Na_2SO_4$ and concentrated to an oil. MeOH (approx. 200 mL) was added to initiate product crystallization. The suspension was heated to 80° C. for 30 min then cooled on ice and the precipitated solid collected by filtration to afford 14.1 g (88%) of 10,10'-propane-2,2-diylbis(5,5,7-trimethyl-2,3-dihydro-1H,5H-pyrido[3,2,1-ij]quinoline) after drying as a light pink solid. $^1$H NMR (300 MHz, CDCl$_3$): δ 6.96 (d, J=8.1 Hz, 2H), 6.82 (d, J=8.1 Hz, 2H), 5.28 (s, 2H), 3.18 (m, 2H), 3.03 (m, 2H), 2.25 (m, 2H), 1.99 (s, 6H), 1.87 (m, 2H), 1.62 (s, 6H), 1.58 (m, 4H), 1.26 (s, 6H), 1.18 (s, 6H).

Example 11. Synthesis of 1,1'-cyclohexane-1,1-diylbis(4-bromobenzene)

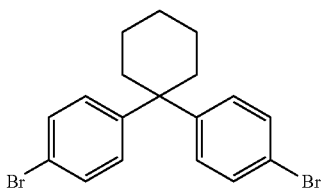

A mixture of 1,1-bis(4-aminophenyl)cyclohexane (25.5 g, 95.7 mmol), water (95 mL) and 48% HBr (142 mL) was stirred at room temperature overnight and then cooled to 0-3° C. using an ice/water bath. A solution of sodium nitrite (13.73 g, 199 mmol) in water (53 mL) was added dropwise over the course of 2 hrs. The resultant dark solution was added to a pre-heated (approx. 50° C.) solution of copper (1) bromide (27.3 g, 190 mmol) in 48% HBr (106 mL). The resultant dark mixture was heated to 90° C. and stirred for 1 h, then cooled and diluted with dichloromethane (500 mL) and water (500 mL). The dichloromethane phase was separated, washed with water and dried over Na$_2$SO$_4$. The extract was concentrated, re-dissolved in small (approx. 40 mL) amount of dichloromethane and passed through a silica gel pad eluting with dichloromethane to remove most of the colored by-products. The still impure material was chromatographed on silica eluting with hexane followed by crystallization from hexane to afford 21.1 g (56%) of 1,1'-cyclohexane-1,1-diylbis(4-bromobenzene) as a white solid. $^1$H NMR (300 MHz, CDCl$_3$): δ 7.38 (d, J=8.7 Hz, 4H), 7.11 (d, J=9 Hz, 4H), 2.19 (m, 4H), 1.51 (br s, 6H). $^{13}$C NMR (75 MHz, CDCl$_3$): δ 147.08, 131.38, 128.94, 119.55, 45.79, 36.88, 26.12, 22.69.

Example 12. Synthesis of 1,1'-cyclohexane-1,1-diylbis(4-bromo-3-nitrobenzene)

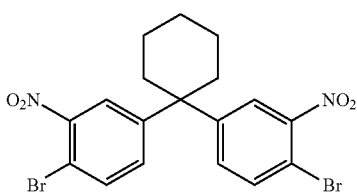 [SMILES: O=[N+]([O-])c1cc(C2(c3ccc(Br)c([N+](=O)[O-])c3)CCCCC2)ccc1Br]

1,1'-Cyclohexane-1,1-diylbis(4-bromo-3-nitrobenzene) was prepared in 51% using the reaction setup described in Example 2 starting from 1,1'-cyclohexane-1,1-diylbis(4-bromobenzene) followed by purification by silica gel chromatography (dichloromethane/hexane) and crystallization from hexane/ethyl acetate. $^1$H NMR (300 MHz, CDCl$_3$): δ 7.78 (d, J=2.4 Hz, 2H), 7.66 (d, J=8.7 Hz, 2H), 7.26 (dd, J$_1$=8.4 Hz, J$_2$=2.4 Hz, 2H), 2.27 (br d, J=6 Hz, 4H), 1.56 (br s, 6H).

Example 13. Synthesis of 3,3'-cyclohexane-1,1-diyldianiline

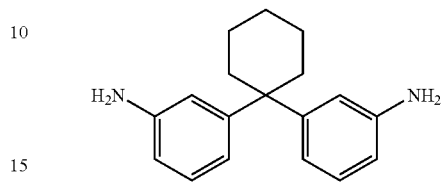

3,3'-Cyclohexane-1,1-diyldianiline was prepared in 98% yield using the reaction setup and workup described in Example 6 starting from 1,1'-cyclohexane-1,1-diylbis(4-bromo-3-nitrobenzene). $^1$H NMR (300 MHz, CDCl$_3$): δ 7.05 (t, J=7.8 Hz, 2H), 6.73 (ddd, J$_1$=8.0 Hz, J$_2$=1.9 Hz, J$_3$=1.0 Hz, 2H), 6.59 (t, J=2.1 Hz, 2H), 6.47 (ddd, J$_1$=7.9 Hz, J$_2$=2.3 Hz, J$_3$=1.0 Hz, 2H), 3.52 (br s, 4H), 2.19 (m, 4H), 1.53 (m, 4H), 1.47 (m, 2H).

Example 14. Synthesis of 8,8'-cyclohexane-1,1-diylbis(2,3,6,7-tetrahydro-1H,5H-pyrido[3,2,1-ij]quinoline)

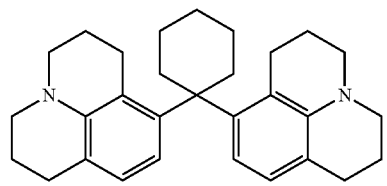 [SMILES: c1cc(C2(c3ccc4c5c3CCCN5CCC4)CCCCC2)c2c3c1CCCN3CCC2]

8,8'-Cyclohexane-1,1-diylbis(2,3,6,7-tetrahydro-1H,5H-pyrido[3,2,1-ij]quinoline) was prepared in 70% yield using the reaction setup and workup described in Example 7 starting from 3,3'-cyclohexane-1,1-diyldianiline (Example 13) and purified by trituration in methanol and filtration. $^1$H NMR (300 MHz, CDCl$_3$): δ 6.92 (d, J=8.1 Hz, 2H), 6.75 (d, J=8.1 Hz, 2H), 3.08 (t, J=5.7 Hz, 4H), 2.93 (t, J=6.5 Hz, 4H), 2.71 (t, J=6.5 Hz, 4H), 2.16 (Br s, 6H), 1.90 (m, 4H), 1.63 (br s, 4H), 1.50 (m, 6H). $^{13}$C NMR (75 MHz, CDCl$_3$): δ 144.92, 143.57, 125.44, 122.92, 119.41, 116.19, 50.92, 50.06, 47.32, 37.36, 28.02, 26.63, 25.02, 23.43, 22.27, 22.23.

Example 15. Synthesis of 7,7'-cyclohexane-1,1-diylbis(2,2,4-trimethyl-1,2-dihydroquinoline)

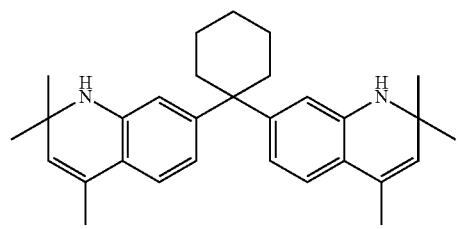

7,7'-Cyclohexane-1,1-diylbis(2,2,4-trimethyl-1,2-dihydroquinoline) was prepared in 75% yield using the reaction setup, workup and column purification described in Example 8 starting from 3,3'-cyclohexane-1,1-diyldianiline (Example 13). $^1$H NMR (300 MHz, CDCl$_3$): δ 6.95 (d, J=7.8 Hz, 2H), 6.59 (dd, J$_1$=8.1 Hz, J$_2$=2.1 Hz, 2H), 6.32 (d, J=2.1 Hz, 2H), 5.22 (d, J=1.5 Hz, 2H), 3.58 (br s, 2H), 2.13 (m, 4H), 1.94 (d, J=1.5 Hz, 6H), 1.53 (m, 4H), 1.45 (m, 2H), 1.24 (s, 12H). $^{13}$C NMR (75 MHz, CDCl$_3$): δ 149.41, 143.14, 128.61, 127.77, 123.45, 119.11, 116.45, 112.39, 52.16, 46.22, 37.31, 31.47, 26.69, 23.30, 18.76.

Example 16. Synthesis of 7,7'-cyclohexane-1,1-diylbis(1,2,2,4-tetramethyl-1,2-dihydroquinoline)

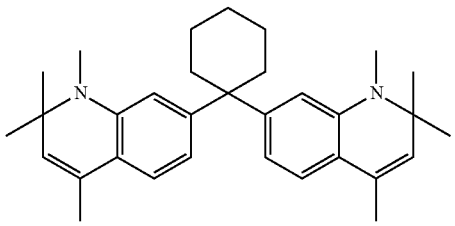

To a solution of 7,7'-cyclohexane-1,1-diylbis(2,2,4-trimethyl-1,2-dihydroquinoline) (1.54 g, 3.6 mmol) in DMF (10 mL) was added solid KHCO$_3$ (2.0 g) followed by methyl iodide (0.54 mL, 8.6 mmol). The reaction was stirred for 60 hrs then concentrated and partitioned between water and ethyl acetate. The extract was washed with brine, dried over Na$_2$SO$_4$ and concentrated. The resultant material was chromatographed on silica eluting with 40% (v/v) dichloromethane in hexane to afford 1.3 g (79%) of 7,7'-cyclohexane-1,1-diylbis(1,2,2,4-tetramethyl-1,2-dihydroquinoline)) as a white amorphous solid. $^1$H NMR (300 MHz, CDCl$_3$): δ 6.94 (d, J=8.1 Hz, 2H), 6.62 (dd, J$_1$=7.8 Hz, J$_2$=1.8 Hz, 2H), 6.49 (d, J=1.5 Hz, 2H), 5.21 (d, J=1.5 Hz, 2H), 2.73 (s, 6H), 2.24 (m, 4H), 1.94 (d, J=1.5 Hz, 6H), 1.58 (m, 4H), 1.48 (m, 2H), 1.26 (s, 12H). $^{13}$C NMR (75 MHz, CDCl$_3$): δ 149.53, 144.99, 129.46, 128.34, 123.05, 120.87, 115.54, 110.35, 56.43, 47.00, 37.48, 30.75, 27.32, 26.70, 23.38, 18.77.

Example 17. Synthesis of 1,1'-cyclopentane-1,1-diyldibenzene

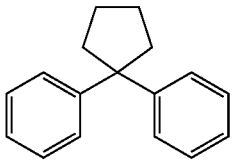 [SMILES: c1ccc(C2(c3ccccc3)CCCC2)cc1]

Sodium hydride (1.25 g, 50 mmol) was added in small portions under argon to a stirred solution (5° C.) of 2,2-diphenylcyclopentanol (Mathre et al., 2013) (10.0 g, 42 mmol) in anhydrous THF (250 ml) over the course of 15 min and then stirred at room temperature for 1 h. Carbon disulfide (3.0 ml, 50 mmol) was added dropwise, the reaction stirred for 1 h and then treated with methyl iodide (4.0 ml, 64 mmol). After being stirred at room temperature for 1 h and at 50° C. for 15 h the reaction was poured on a mixture of ice (300 g) and acetic acid (6 ml), extracted with ethyl acetate, washed with brine, dried (Na2SO4) and concentrated. Silica gel chromatography of the resultant material eluting with 9:1 hexane-ethyl acetate afforded 0-(2,2-diphenylcyclopentyl)S-methyl carbonodithioate (7.7 g), which was then dissolved in toluene (80 ml) and treated with tributyltin hydride (8.2 ml, 30.4 mmol) and AIBN (40 mg). After being refluxed under argon for 2 h the reaction was cooled, washed with water (2×100 ml), brine (100 ml), dried (Na2SO4) and concentrated. The obtained crude 1,1'-cyclopentane-1,1-diyldibenzene was purified by silica gel chromatography eluting with hexane followed by trituration in methanol to afford 3.0 g (27%) of the title compound as a white crystalline solid. 1H NMR (300 MHz, CDCl3): δ 7.3-7.4 (m, 8H), 7.15-7.08 (m, 2H), 2.30 (m, 4H), 1.71 (m, 4H). 13C NMR (75 MHz, CDCl3): δ 149.14, 128.29, 127.28, 125.75, 56.06, 38.83, 23.22.

Example 18. Synthesis of 1,1'-cyclopentane-1,1-diylbis(4-bromobenzene)

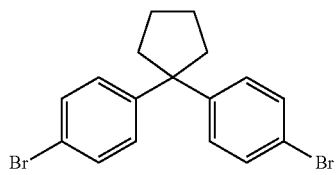 [SMILES: Brc1ccc(C2(c3ccc(Br)cc3)CCCC2)cc1]

1,1'-Cyclopentane-1,1-diylbis(4-bromobenzene) was prepared by analogy to the procedure described in Example 1 in 78% yield (off-white solid) starting from 1,1'-cyclopentane-1,1-diyldibenzene (Example 17). $^1$H NMR (300 MHz, CDCl$_3$): δ 7.36 (d, J=8.4 Hz, 4H), 7.10 (d, J=8.7 Hz, 4H), 2.22 (m, 4H), 1.70 (m, 4H). $^{13}$C NMR (75 MHz, CDCl$_3$): δ 147.30, 131.21, 128.76, 119.65, 55.21, 38.48, 22.82.

Example 19. Synthesis of 1,1'-cyclopentane-1,1-diylbis(4-bromo-3-nitrobenzene)

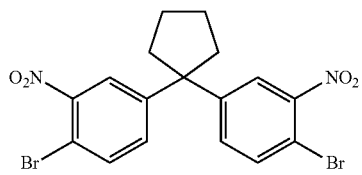 [SMILES: O=[N+]([O-])c1cc(C2(c3ccc(Br)c([N+](=O)[O-])c3)CCCC2)ccc1Br]

To a stirred solution of 1,1'-cyclopentane-1,1-diylbis(4-bromo-3-nitrobenzene) (Example 18) (3.99 g, 10.5 mmol) in dichloromethane (55 ml) was added conc. H$_2$SO$_4$ (4.1 ml) followed by dropwise addition of 90% HNO$_3$ (1.4 ml). After being stirred for 3 h another portion of conc. H$_2$SO$_4$ (3 ml) and 90% HNO$_3$ (0.2 ml) was added. After being stirred for 10 h the reaction was diluted with dichloromethane, washed with water, saturated NaHCO$_3$, dried (Na$_2$SO$_4$) and concentrated. The resultant oil was chromatographed on silica eluting with 30-40% dichloromethane in hexane to afford 1,1'-cyclopentane-1,1-diylbis(4-bromo-3-nitrobenzene) (2.8 g, 56% yield) as an off-white solid. $^1$H NMR (300 MHz, CDCl$_3$): δ 7.75 (d, J=2.1 Hz, 2H), 7.65 (d, J=8.4 Hz, 2H), 7.26 (dd, J$_1$=8.7 Hz, J$_2$=2.1 Hz, 2H), 2.31 (m, 4H), 1.78 (m, 4H). $^{13}$C NMR (75 MHz, CDCl$_3$): δ 150.01, 148.29, 135.50, 132.35, 124.05, 112.77, 55.63, 38.70, 22.89.

Example 20. Synthesis of 3,3'-cyclopentane-1,1-diyldianiline

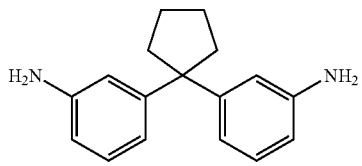 [SMILES: Nc1cccc(C2(c3cccc(N)c3)CCCC2)c1]

3,3'-Cyclopentane-1,1-diyldianiline was prepared in 97% yield using the reaction setup and workup described in Example 6 starting from 1,1'-cyclopentane-1,1-diylbis(4-bromo-3-nitrobenzene) (Example 19). $^1$H NMR (300 MHz, CDCl$_3$): δ 7.03 (t, J=7.8 Hz, 2H), 6.72 (ddd, J$_1$=7.7 Hz, J$_2$=1.6 Hz, J$_3$=1.0 Hz, 2H), 6.58 (t, J=1.9 Hz, 2H), 6.47 (ddd, J$_1$=7.8 Hz, J$_2$=2.4 Hz, J$_3$=0.9 Hz, 2H), 3.54 (br s, 4H), 2.21 (m, 4H), 1.68 (m, 4H). $^{13}$C NMR (75 MHz, CDCl$_3$): δ 150.21, 145.91, 128.76, 117.43, 114.33, 112.52, 55.60, 38.42, 22.96.

Example 21. Synthesis of 7,7'-cyclopentane-1,1-diylbis(2,2,4-trimethyl-1,2-dihydroquinoline)

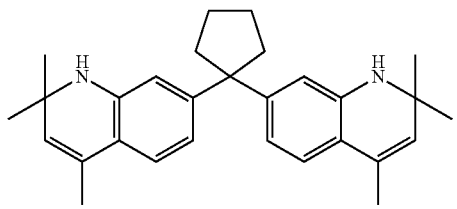

7,7'-Cyclopentane-1,1-diylbis(2,2,4-trimethyl-1,2-dihydroquinoline) was prepared in 67% yield using the reaction setup, workup and column purification described in Example 8 starting from 3,3'-cyclopentane-1,1-diyldianiline (Example 20). $^1$H NMR (300 MHz, CDCl$_3$): δ 6.92 (d, J=8.1 Hz, 2H), 6.58 (dd, J$_1$=8.1 Hz, J$_2$=1.8 Hz, 2H), 6.31 (d, J=1.8 Hz, 2H), 5.22 (d, J=1.5 Hz, 2H), 3.56 (br s, 2H), 2.16 (m, 4H), 1.94 (d, J=1.5 Hz, 6H), 1.67 (m, 4H), 1.24 (s, 12H). $^{13}$C NMR (75 MHz, CDCl$_3$): δ 149.52, 142.72, 128.34, 127.43, 123.03, 118.95, 115.93, 111.99, 55.41, 51.87, 38.46, 31.25, 23.08, 18.52.

Example 22. Synthesis of 7,7'-cyclopentane-1,1-diylbis(1,2,2,4-tetramethyl-1,2-dihydroquinoline)

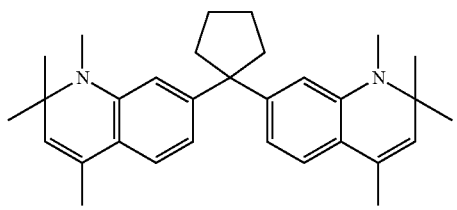

7,7'-Cyclopentane-1,1-diylbis(1,2,2,4-tetramethyl-1,2-dihydroquinoline) was prepared by analogy to the procedure described in Example 9 including column purification (silica, elution with 5% ethyl acetate in hexane) and crystallization from hexane starting from 7,7'-cyclopentane-1,1-diylbis(2,2,4-trimethyl-1,2-dihydroquinoline) (Example 21). Yield: 63% (white solid). $^1$H NMR (300 MHz, CDCl$_3$): δ 6.92 (d, J=7.8 Hz, 2H), 6.61 (dd, J$_1$=7.8 Hz, J$_2$=1.8 Hz, 2H), 6.48 (d, J=1.5 Hz, 2H), 5.21 (d, J=1.5 Hz, 2H), 2.74 (s, 6H), 2.27 (m, 4H), 1.94 (d, J=1.5 Hz, 6H), 1.70 (m, 4H), 1.26 (s, 12H). $^{13}$C NMR (75 MHz, CDCl$_3$): δ 149.65, 144.61, 129.12, 128.07, 122.638, 120.69, 115.08, 109.90, 56.24, 56.15, 38.66, 30.51, 27.11, 23.14, 18.54.

Example 23. Synthesis of 1,1'-cycloheptane-1,1-diylbis(4-bromobenzene)

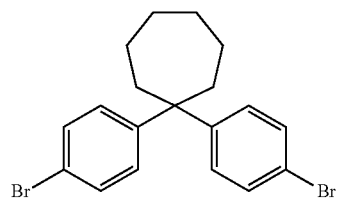 [SMILES: Brc1ccc(C2(c3ccc(Br)cc3)CCCCCC2)cc1]

A mixture of 4,4'-cycloheptane-1,1-diyldianiline JP566089 (4.58 g, 16.3 mmol), water (16 mL) and 48% HBr (24 mL) was stirred at room temperature overnight and then cooled to 0-3° C. using an ice/water bath. A solution of sodium nitrite (2.33 g, 33.9 mmol) in water (9 mL) was added dropwise over the course of 30 min. The resultant grey suspension was allowed to warm to room temperature and stirred for 2 more hrs. The resultant bis-diazonium salt was added to a stirred solution of copper (I) bromide (4.65 g, 32 mmol) in 48% HBr (18 mL). Two (10 mL) portions of 48% HBr were used to rinse the diazotization flask and added to the copper (I) bromide solution too. The combined purple mixture was heated to 90° C. and stirred for 1 h, then cooled and diluted with dichloromethane (200 mL) and water (400 mL). The dichloromethane phase was separated, washed with water and dried over Na$_2$SO$_4$. The extract was concentrated, re-dissolved in small (approx. 40 mL) amount of dichloromethane and passed through a pad of silica gel eluting with dichloromethane to remove most of the colored by-products. The crude product was chromatographed on silica eluting with hexane to afford 1.6 g (24%) of 1,1'-cycloheptane-1,1-diylbis(4-bromobenzene) as a white solid. $^1$H NMR (300 MHz, CDCl$_3$): δ 7.36 (d, J=8.7 Hz, 4H), 7.01 (d, J=8.4 4H), 2.22 (m, 4H), 1.68 (m, 4H), 1.57 (m, 4H). $^{13}$C NMR (75 MHz, CDCl$_3$): δ 149.49, 131.14, 129.03, 119.41, 49.62, 40.05, 29.97, 24.15.

Example 24. Synthesis of 1,1'-cycloheptane-1,1-diylbis(4-bromo-3-nitrobenzene)

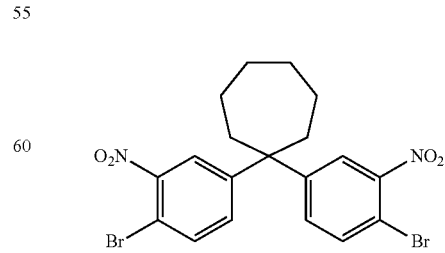

1,1'-Cycloheptane-1,1-diylbis(4-bromo-3-nitrobenzene) was prepared by analogy to the procedure described in Example 19 in 81% yiled (white solid) starting from 1,1'-cycloheptane-1,1-diylbis(4-bromobenzene) (Example 23). $^1$H NMR (300 MHz, CDCl$_3$): δ 7.69 (d, J=2.4 Hz, 2H), 7.63 (d, J=8.4 Hz, 2H), 7.13 (dd, J$_1$=8.7 Hz, J$_2$=2.4 Hz, 2H), 2.29 (m, 4H), 1.71 (m, 4H), 1.61 (m, 4H). $^{13}$C NMR (75 MHz, CDCl$_3$): δ 150.48, 150.04, 135.42, 132.65, 124.18, 112.53, 50.28, 40.02, 29.96, 24.09.

Example 25. Synthesis of 3,3'-cycloheptane-1,1-diyldianiline

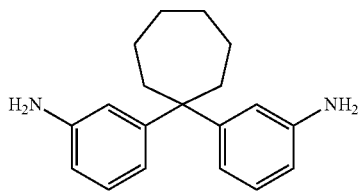 [SMILES: Nc1cccc(C2(c3cccc(N)c3)CCCCCC2)c1]

3,3'-Cycloheptane-1,1-diyldianiline was prepared in 94% yield (off-white solid) using the reaction setup and workup described in Example 6 starting from 1,1'-cycloheptane-1,1-diylbis(4-bromo-3-nitrobenzene) (Example 24). $^1$H NMR (300 MHz, CDCl$_3$): δ 7.03 (m, 2H), 6.62 (m, 2H), 6.46 (m, 4H), 3.35 (br s, 4H), 2.20 (m, 4H), 1.69 (m, 4H), 1.55 (m, 4H). $^{13}$C NMR (75 MHz, CDCl$_3$): δ 152.45, 145.88, 128.70, 117.68, 114.60, 112.28, 49.90, 40.08, 30.32, 24.40.

Example 26. Synthesis of 7,7'-cycloheptane-1,1-diylbis(2,2,4-trimethyl-1,2-dihydroquinoline)

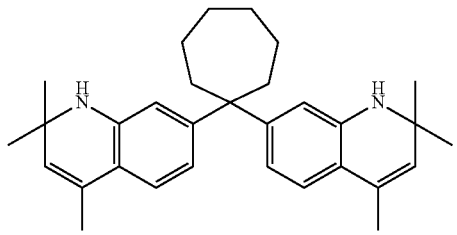

7,7'-Cycloheptane-1,1-diylbis(2,2,4-trimethyl-1,2-dihydroquinoline) was prepared in 78% yield (off-white solid) using the reaction setup, workup and column purification described in Example 8 starting from 3,3'-cycloheptane-1,1-diyldianiline (Example 25). $^1$H NMR (300 MHz, CDCl$_3$): δ 6.93 (d, J=8.1 Hz, 2H), 6.50 (dd, J$_1$=8.0 Hz, J$_2$=1.9 Hz, 2H), 6.22 (d, J=1.8 Hz, 2H), 5.22 (d, J=1.2 Hz, 2H), 3.56 (br s, 2H), 2.18 (m, 4H), 1.95 (d, J=1.5 Hz, 6H), 1.68 (m, 4H), 1.55 (m, 4H), 1.24 (s, 12H). $^{13}$C NMR (75 MHz, CDCl$_3$): δ 151.75, 142.69, 128.33, 127.44, 122.97, 118.72, 116.09, 112.26, 51.89, 49.72, 40.07, 31.23, 30.38, 24.45, 18.52.

Example 27. Synthesis of 7,7'-cycloheptane-1,1-diylbis(1,2,2,4-tetramethyl-1,2-dihydroquinoline)

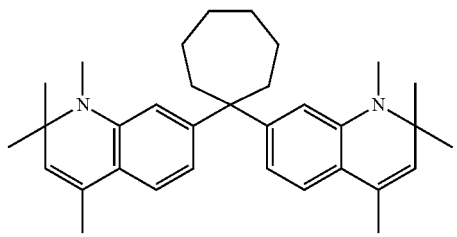

7,7'-Cycloheptane-1,1-diylbis(1,2,2,4-tetramethyl-1,2-dihydroquinoline) was prepared in 83% yield (off-white solid) by analogy to the procedure described in Example 9 including column purification (silica, elution with 5% ethyl acetate in hexane) starting from 7,7'-cycloheptane-1,1-diylbis(2,2,4-trimethyl-1,2-dihydroquinoline) (Example 26). $^1$H NMR (300 MHz, CDCl$_3$): δ 6.93 (d, J=7.8 Hz, 2H), 6.51 (dd, J$_1$=7.9 Hz, J$_2$=1.7 Hz, 2H), 6.39 (d, J=1.8 Hz, 2H), 5.22 (d, J=1.2 Hz, 2H), 2.70 (s, 6H), 2.28 (m, 4H), 1.94 (d, J=1.5 Hz, 6H), 1.72 (m, 4H), 1.55 (m, 4H), 1.26 (s, 12H). $^{13}$C NMR (75 MHz, CDCl$_3$): δ 151.80, 144.56, 129.15, 128.13, 122.55, 120.53, 115.41, 110.28, 56.11, 50.43, 40.33, 30.45, 30.27, 26.98, 24.61, 18.52.

Example 28. Synthesis of 2,2-bis(4-bromophenyl)tricyclo[3.3.1.1$^{3,7}$]decane

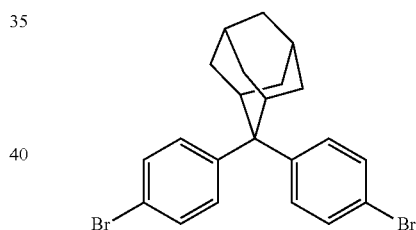

A mixture of 2,2-bis(4-aminophenyl)adamantane (Salvio (2013)) (5.2 g, 16.3 mmol), water (16 mL) and 48% HBr (24 mL) was stirred at room temperature overnight and then cooled to 0-3° C. using an ice/water bath. A solution of sodium nitrite (2.33 g, 33.9 mmol) in water (9 mL) was added dropwise over the course of 30 min. The resultant grey suspension was allowed to warm to room temperature and stirred for 2 more hrs. The resultant bis-diazonium salt was added to a stirred solution of copper (1) bromide (4.65 g, 32 mmol) in 48% HBr (18 mL). Two (10 mL) portions of 48% HBr were used to rinse the diazotization flask and added to the copper (1) bromide solution too. The combined purple mixture was heated to 90° C. and stirred for 1 h, then cooled and diluted with dichloromethane (200 mL) and water (400 mL). The dichloromethane phase was separated, washed with water and dried over Na$_2$SO$_4$. The extract was concentrated, re-dissolved in small (approx. 40 mL) amount of dichloromethane and passed through a pad of silica gel eluting with dichloromethane to remove most of the colored by-products. The crude product was chromatographed on silica eluting with hexane to afford 4.5 g (62%) of 2,2-bis(4-bromophenyl)tricyclo[3.3.1.13,7]decane as a white solid. $^1$H NMR (300 MHz, CDCl$_3$): δ 7.34 (skewed d, J=8.7 Hz, 4H), 7.24 (skewed d, J=8.7 Hz, 4H), 3.15 (br s, 2H), 1.99 (br s, 2H), 1.95 (br s, 2H), 1.82 (br s, 2H), 1.76 (br s, 2H), 1.71 (br s, 2H), 1.70 (br s, 2H). $^{13}$C NMR (75 MHz, CDCl$_3$): δ 147.29, 131.98, 127.91, 119.10, 50.52, 37.99, 33.40, 32.07, 27.57.

Example 29. Synthesis of 2,2-bis(4-bromo-3-nitrophenyl)tricyclo[3.3.1.1$^{3,7}$]decane

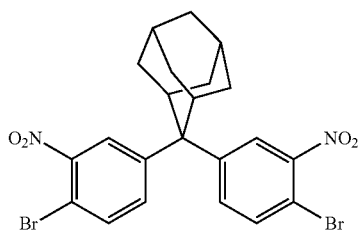 [SMILES: O=[N+]([O-])c1cc(C2(c3ccc(Br)c([N+](=O)[O-])c3)C3CC4CC(C3)CC2C4)ccc1Br]

2,2-Bis(4-bromo-3-nitrophenyl)tricyclo[3.3.1.13,7]decane was prepared in 16% yield using the reaction setup, workup and column purification described in Example 8 starting from 2,2-bis(4-bromophenyl)tricyclo[3.3.1.13,7]decane (Example 28). $^1$H NMR (300 MHz, CDCl$_3$): δ 7.85 (d, J=2.4 Hz, 2H), 7.65 (d, J=8.7 Hz, 2H), 7.44 (dd, J$_1$=8.4 Hz, J$_2$=2.4 Hz, 2H), 3.17 (br s, 2H), 1.89 (m, 10H), 1.74 (br s, 2H). $^{13}$C NMR (75 MHz, CDCl$_3$): δ 150.01, 148.41, 136.04, 131.11, 123.65, 112.07, 50.91, 37.53, 33.08, 32.15, 27.23.

Example 30. Synthesis of 3,3'-tricyclo[3.3.1.1$^{3,7}$]decane-2,2-diyldianiline

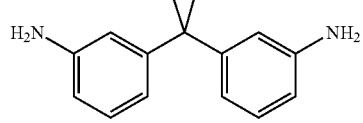

3,3'-Tricyclo[3.3.1.13,7]decane-2,2-diyldianiline was prepared in 94% yield using the reaction setup and workup described in Example 6 starting from 2,2-bis(4-bromo-3-nitrophenyl)tricyclo[3.3.1.13,7]decane followed by silica gel chromatography eluting with ethyl acetate. $^1$H NMR (300 MHz, CDCl$_3$): δ 7.00 (t, J=7.8 Hz, 2H), 6.83 (ddd, J$_1$=8.0 Hz, J$_2$=unresolved, J$_3$=unresolved, 2H), 6.73 (t, J=2.1 Hz, 2H), 6.36 (ddd, J$_1$=7.8 Hz, J$_2$=2.1 Hz, J$_3$=0.9 Hz, 2H), 3.49 (br s, 4H), 3.11 (br s, 2H), 2.08 (br s, 2H), 2.04 (br s, 2H), 1.79 (br s, 2H), 1.72 (br s, 2H), 1.68 (br s, 4H). 13C NMR (75 MHz, CDCl$_3$): δ 149.92, 146.48, 129.34, 116.86, 113.39, 112.24, 50.64, 38.25, 33.80, 32.34, 27.74.

Example 31. Synthesis of 7,7'-tricyclo[3.3.1.1$^{3,7}$]decane-2,2-diylbis(2,2,4-trimethyl-1,2-dihydroquinoline)

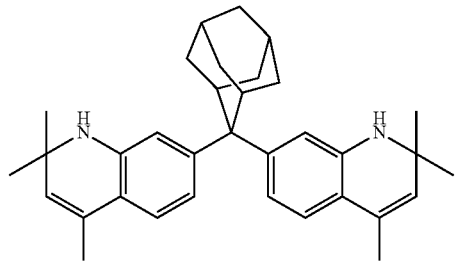

7,7'-Tricyclo[3.3.1.13,7]decane-2,2-diylbis(2,2,4-trimethyl-1,2-dihydroquinoline) was prepared in 61% yield using the reaction setup, workup and column purification described in Example 8 starting from 3,3'-tricyclo[3.3.1.13,7]decane-2,2-diyldianiline (Example 30). $^1$H NMR (300 MHz, CDCl$_3$): δ 6.89 (d, J=8.1 Hz, 2H), 6.68 (dd, J$_1$=8.1 Hz, J$_2$=1.8 Hz, 2H), 6.45 (d, J=1.8 Hz, 2H), 5.18 (d, J=1.2 Hz, 2H), 3.57 (br s, 2H), 3.02 (br s, 2H), 2.09 (br s, 2H), 2.05 (br s, 2H), 1.90 (d, J=1.2 Hz, 6H), 1.76 (br s, 2H), 1.68 (br s, 4H), 1.64 (br s, 2H), 1.24 (s, 12H). 13C NMR (75 MHz, CDCl$_3$): δ 149.07, 143.30128.59, 127.44, 123.72, 118.54, 115.28, 110.88, 52.18, 50.44, 38.31, 33.87, 32.33, 31.59, 27.74, 18.72.

Example 32. Synthesis of 7,7'-tricyclo[3.3.1.1$^{3,7}$]decane-2,2-diylbis(1,2,2,4-tetramethyl-1,2-dihydroquinoline)

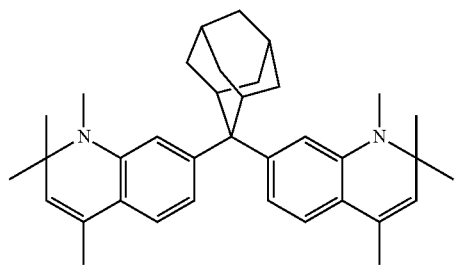

To a solution of 7,7'-tricyclo[3.3.1.13,7]decane-2,2-diylbis(2,2,4-trimethyl-1,2-dihydroquinoline) (0.4 g, 0.83 mmol) in THF (3 mL) was added solid KHCO$_3$ (0.46 g) followed by methyl iodide (0.15 mL, 12.8 mmol). The reaction was stirred for 48 hrs and then treated with another (0.05 mL) portion of methyl iodide. After being stirred for 2 more days the reaction was concentrated and partitioned between water and dichloromethane. The extract was washed with brine, dried over Na$_2$SO$_4$ and concentrated. The resultant material was chromatographed on silica eluting with 50% (v/v) dichloromethane in hexane to afford 0.305 g (72.5%) of 7,7'-tricyclo[3.3.1.13,7]decane-2,2-diylbis(1,2,2,4-tetramethyl-1,2-dihydroquinoline) as an off-white solid. $^1$H NMR (300 MHz, CDCl$_3$): δ 6.89 (d, J=8.1 Hz, 2H), 6.72 (dd, J$_1$=8.1 Hz, J$_2$=1.2 Hz, 2H), 6.61 (d, J=1.2 Hz, 2H), 5.16 (d, J=1.5 Hz, 2H), 3.16 (br s, 2H), 2.77 (s, 6H), 2.15 (br s, 2H), 2.11 (br s, 2H), 1.90 (d, J=1.2 Hz, 6H), 1.77 (br s, 2H), 1.69 (m, 6H), 1.25 (s, 12H). $^{13}$C NMR (75 MHz, CDCl$_3$): δ 148.99, 144.84, 128.84, 127.92, 122.98, 119.91, 114.06, 108.50, 56.25, 50.99, 38.12, 33.70, 32.29, 30.64, 27.45, 27.27, 18.47.

The following examples illustrate the preparation of carborhodamine dyes of general Structure I.

Example 33. Synthesis of 5-bromo-3-chlorophthalic Acid

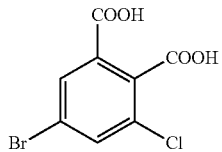 [SMILES: O=C(O)c1cc(Br)cc(Cl)c1C(=O)O]

To a pre-heated (110° C., bath temperature) solution of 4-bromo-1-chloro-6-methylbenzoic acid (9.0 g, 36 mmol) in a mixture of 1 N KOH (108 mL and water (72 mL) was added solid KMnO$_4$ (5.69 g, 37.3 mmol) and the reaction was stirred for 1 h before being treated with another 5.9 g portion of KMnO$_4$. After being stirred for 2 hrs another 5.9 g portion of KMnO$_4$ was added and stirring was continued for 2 more hrs at 110° C. (oil bath temperature) and then allowed to slowly cool to room temperature overnight. The precipitated MnO$_2$ was removed by filtration through a pad of Celite filtering agent. The solids were washed with water and the combined filtrate (approx. 400 mL) treated with conc. HCl (15 mL). The precipitated product was taken into diethyl ether, the extract washed with brine, dried over Na$_2$SO$_4$ and concentrated to afford 7.9 g (78%) of 5-bromo-3-chlorophthalic acid as a white solid. $^1$H NMR (300 MHz, DMSO-d6): δ 13.80 (br s, 2H), 8.12 (d, J=2.1 Hz, 1H), 8.01 (d, J=2.1 Hz, 1H).

Example 34. Synthesis of 5-bromo-3-chlorophthalic anhydride

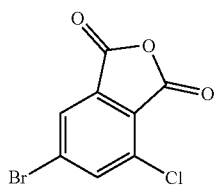

A mixture of 5-bromo-3-chlorophthalic acid (Example 33) (7.9 g, 28.2 mmol) and acetic anhydride (30 mL) was heated at 145° C. (bath temperature) under argon for 2.5 h. The obtained solution was cooled and concentrated to a white solid which was then re-crystallized from anhydrous pentane to yield 6.8 g (92%) of desired 5-bromo-3-chlorophthalic anhydride. $^1$H NMR (300 MHz, CDCl$_3$): δ 8.07 (d, J=1.2 Hz, 1H), 8.01 (d, J=1.2 Hz, 1H). $^{13}$C NMR (75 MHz, CDCl$_3$): δ 160.41, 159.35, 140.27, 134.72, 134.46, 131.91, 127.69, 126.58.

Example 35. General Procedure for the Preparation of Carborhodamine Compounds of General Structure I Method A A solution of a phthalic anhydride or a substituted phthalic anhydride of general Structure II (0.75 mmol) and anhydrous AlCl$_3$ (100 mg, 0.75 mmol) in anhydrous 1,2-dichloroethane (2 mL) is added dropwise to a stirred solution of a compound of general Structure III (0.5 mmol) and AlCl$_3$ (133 mg, 1 mmol) in anhydrous 1,2-dichloroethane (5 mL) under argon. The reaction is stirred at ambient temperature for 1-3 hrs then diluted with dichloromethane and extracted with 1 N HCl (approx. 50 mL). The dichloromethane phase is separated, washed with saturated NaHCO$_3$ and dried over Na$_2$SO$_4$. The crude dye, obtained after evaporation of the solvent, is purified on silica eluting with suitable eluent.

Method B

A solution of a phthalic anhydride or a substituted phthalic anhydride of general Structure II (0.5 mmol) and anhydrous AlCl$_3$ (133 mg, 1 mmol) in anhydrous 1,2-dichloroethane (1 mL) is added dropwise to a stirred solution of a compound of general Structure III (0.5 mmol) in anhydrous 1,2-dichloroethane (2 mL) under argon. The reaction is stirred at ambient temperature for 30 min then treated with triethylamine (0.14 mL, 1 mmol). The treatments with phthalic anhydride (0.5 mmol)/AlCl$_3$ (1 mmol) dichloroethane solution and triethylamine (1 mmol) repeated three more times with 30 min intervals. The final reaction is diluted with dichloromethane and extracted with 1 N HCl (approx. 50 mL). The dichloromethane phase is separated, washed with saturated NaHCO$_3$ and dried over Na$_2$SO$_4$. The crude dye, obtained after evaporation of the solvent, is purified on silica eluting with suitable eluent.

Examples of compounds synthesized according to those methods along with purification details and analytical data are summarized below.

Compound EL931-085

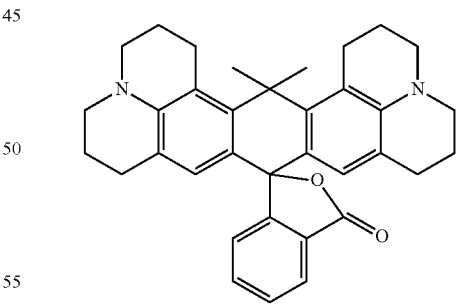

Compound EL931-085 was synthesized by condensing 8,8'-propane-2,2-diylbis(2,3,6,7-tetrahydro-1H,5H-pyrido[3,2,1-ij]quinoline) (Example 7) and phthalic anhydride according to method A. Silica gel column purification: 20-80% (v/v) methanol in dichloromethane. Yield: 81%, dark blue solid. $^1$H NMR (300 MHz, CDCl$_3$): δ 8.12 (dd, J$_1$=7 Hz, J$_2$=unresolved, 1H), 7.53 (m, 2H), 7.06 (dd, J$_1$=7 Hz, J$_2$=1.2, 1H), 6.26 (s, 2H), 3.33 (t, J=6.4 Hz, 4H), 3.27 (t, J=5.7 Hz, 4H), 2.94 (m, 4H), 2.46 (m, 4H), 2.04 (s, 3H), 1.98 (s+m, 7H), 1.85 (m, 4H).

Compound EL931-083

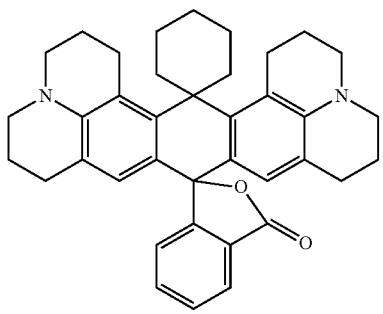 [SMILES: O=C1OC2(c3ccccc31)c1cc3c4c(c1C1(CCCCC1)c1c2cc2c5c1CCCN5CCC2)CCCN4CCC3]

Compound EL931-083 was synthesized by condensing 8,8'-cyclohexane-1,1-diylbis(2,3,6,7-tetrahydro-1H,5H-pyrido[3,2,1-ij]quinoline) (Example 14) and phthalic anhydride according to method A. Silica gel column purification: 20-80% (v/v) methanol in dichloromethane. Yield: 61%, blue-green solid. $^1$H NMR (300 MHz, CDCl$_3$): δ 8.05 (dd, J$_1$=7 Hz, J$_2$=1.4 Hz, 1H), 7.52 (m, 2H), 7.11 (dd, J$_1$=7 Hz, J$_2$=1.2, 1H), 6.25 (s, 2H), 3.27 (m, 8H), 3.06 (m, 4H), 2.50 (m, 4H), 2.43 (m, 4H), 2.0-1.4 (m, 14H). $^{13}$C NMR (75 MHz, CDCl$_3$): δ 169.73, 151.94, 146.78, 133.28, 132.25, 130.90, 130.30, 128.46, 127.20, 126.63, 122.103121.99, 120.21, 77.23, 51.40, 50.30, 46.38, 40.87, 40.60, 27.68, 27.39, 22.61, 22.36, 22.09, 21.51, 21.32.

Compound EL931-069

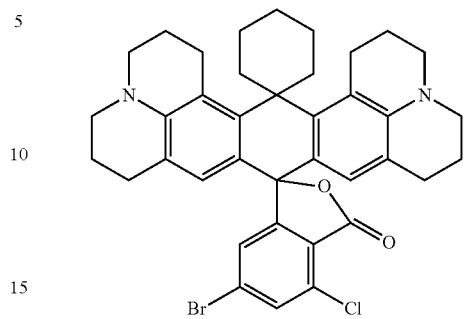

Compound EL931-069 was synthesized by condensing 8,8'-cyclohexane-1,1-diylbis(2,3,6,7-tetrahydro-1H,5H-pyrido[3,2,1-ij]quinoline) (Example 14) and 5-bromo-3-chlorophthalic anhydride (Example 34) according to method A as a 10:2 mixture of two isomers. Silica gel column purification: 20-40% (v/v) methanol in dichloromethane. Yield (10:2 mixture of two isomers): 55%, dark green solid. $^1$H NMR (300 MHz, CDCl$_3$)(main isomer's signals only): δ 7.60 (d, J=1.8 Hz, 1H), 7.07 (d, J=1.5 Hz, 1H), 6.16 (s, 2H), 3.21 (m, 8H), 3.02 (t, J=5.8 Hz, 4H), 2.60-2.35 (m, 8H), 2.05-1.58 (m, 14H).

Compound EL931-074

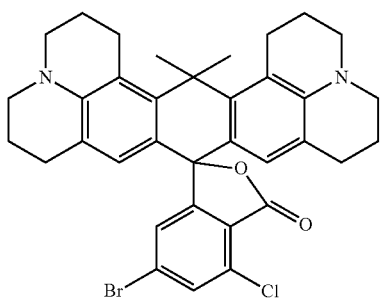 [SMILES: CC1(C)c2c(cc3c4c2CCCN4CCC3)C2(OC(=O)c3c(Cl)cc(Br)cc32)c2cc3c4c(c21)CCCN4CCC3]

Compound EL931-074 was synthesized by condensing 8,8'-propane-2,2-diylbis(2,3,6,7-tetrahydro-1H,5H-pyrido[3,2,1-ij]quinoline) (Example 7) and 5-bromo-3-chlorophthalic anhydride (Example 34) according to method A as a 10:2 mixture of two isomers. Silica gel column purification: 20-40% (v/v) methanol in dichloromethane. Yield (main isomer): 49%, dark blue solid. $^1$H NMR (300 MHz, CDCl$_3$): δ 7.57 (d, J=1.2 Hz, 1H), 6.99 (d, J=1.2 Hz, 1H), 6.15 (s, 2H), 3.22 (m, 8H), 2.94 (m, 4H), 2.54 (m, 4H), 2.05 (s, 3H), 1.98 (s+m, 7H), 1.85 (m, 4H).

Compound EL931-114

Compound EL931-114 was synthesized by condensing 7,7'-propane-2,2-diylbis(1,2,2,4-tetramethyl-1,2-dihydroquinoline) (Example 9) and phthalic anhydride according to method A. Silica gel column purification: 20% (v/v) acetone in dichloromethane. Yield: 49%, light green solid. $^1$H NMR (300 MHz, CDCl$_3$): δ 7.99 (dd, J$_1$=6.3 Hz, J$_2$=1.5 Hz, 1H), 7.54 (m, 2H), 7.06 (dd, J$_1$=7.5 Hz, J$_2$=1.2 Hz, 1H), 6.62 (s, 2H), 6.29 (s, 2H), 5.20 (d, J=0.9 Hz, 2H), 2.87 (s, 6H), 1.83 (s, 3H), 1.76 (s, 3H), 1.61 (d, J=1.2 Hz, 6H), 1.32 (s, 6H), 1.27 (s, 6H). $^{13}$C NMR (75 MHz, CDCl$_3$): δ 171.5, 155.74, 146.71, 145.60, 134.47, 130.27, 128.92, 127.36, 127.34, 124.92, 124.15, 122.59, 122.18, 119.8, 107.31, 56.83, 38.62, 35.39, 32.76, 31.05, 28.64, 27.57, 18.30.

Compound EL931-094

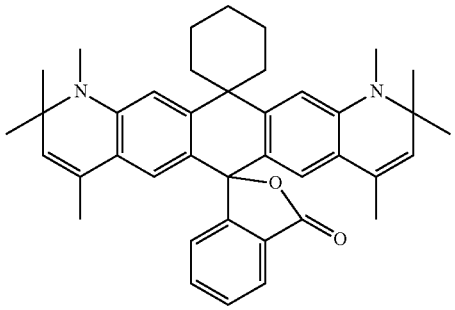

Compound EL931-094 was synthesized by condensing 7,7'-cyclohexane-1,1-diylbis(1,2,2,4-tetramethyl-1,2-dihydroquinoline) (Example 16) and phthalic anhydride according to method A. Silica gel column purification: 20% (v/v) acetone in dichloromethane. Yield: 53%, light green solid. $^1$H NMR (300 MHz, CDCl$_3$): δ 8.00 (dd, J$_1$=7 Hz, J$_2$=unresolved, 1H), 7.59 (m, 2H), 7.10 (dd, J$_1$=7 Hz, J$_2$=unresolved, 1H), 6.92 (s, 2H), 6.23 (s, 2H), 5.17 (s, 2H), 2.89 (s, 6H), 2.46 (t, J=6.3 Hz, 2H), 2.18 (m, 4H), 1.70 (m, 2H), 1.60 (m, 2H), 1.55 (s, 6H), 1.29 (s, 12H). $^{13}$C NMR (75 MHz, CDCl$_3$): δ 171.18, 154.86, 150.04, 145.20, 134.01, 129.88, 129.10, 128.24, 127.47, 125.03, 124.98, 123.46, 121.38, 121.02, 108.38, 56.83, 44.13, 42.66, 34.29, 31.07, 28.25, 27.64, 25.41, 25.08, 22.60, 18.13.

Compound EL939-053

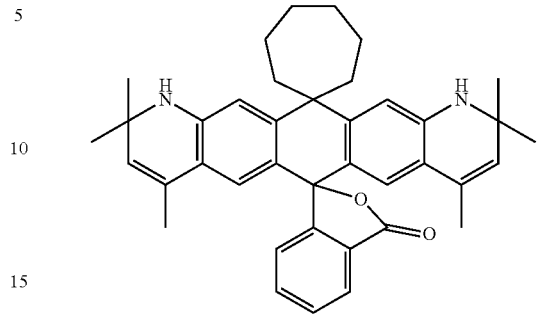

Compound EL939-053 was synthesized by condensing 7,7'-cycloheptane-1,1-diylbis(1,2,2,4-tetramethyl-1,2-dihydroquinoline) (Example 27) and phthalic anhydride according to method A. Purification: Silica gel column (20% (v/v) acetone in dichloromethane). Yield (main isomer): 51%, light green solid. $^1$H NMR (300 MHz, CDCl$_3$): δ 8.00 (d, J=6.6 Hz, 1H), 7.58 (m, 2H), 7.17 (d, J=6.9 Hz, 1H), 6.81 (s, 2H), 6.21 (s, 2H), 5.18 (d, J=0.9 Hz, 2H), 2.90 (s, 6H), 2.60 (m, 2H), 2.22 (m, 2H), 2.14 (m, 2H), 1.86 (m, 2H), 1.68 (m, 4H), 1.55 (d, J=0.9 Hz, 6H), 1.31 (s, 6H), 1.28 (s, 6H). $^{13}$C NMR (75 MHz, CDCl$_3$): δ 171.05, 154.62, 150.21, 145.34, 134.17, 129.99, 129.11, 128.48, 127.39, 124.96, 124.81, 122.97, 121.33, 120.35, 109.04, 56.86, 47.32, 47.07, 42.56, 33.31, 32.07, 31.22, 30.96, 28.56, 28.47, 27.61, 25.81, 18.16.

Compound EL939-176

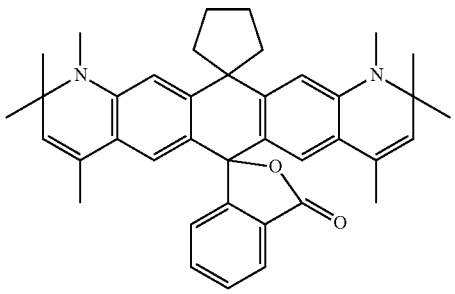

Compound EL939-176 was synthesized by condensing 7,7'-cyclopentane-1,1-diylbis(1,2,2,4-tetramethyl-1,2-dihydroquinoline) (Example 22) and phthalic anhydride according to method A. Purification: Silica gel column (20% (v/v) acetone in dichloromethane). Yield (main isomer): 57%, light green solid. $^1$H NMR (300 MHz, CDCl$_3$): δ 507.99 (d, J=6.6 Hz, 1H), 7.56 (m, 2H), 7.11 (d, J=6.9 Hz, 1H), 6.57 (s, 2H), 6.28 (s, 2H), 5.19 (s, 2H), 2.86 (s, 6H), 2.55 (t, J=7.8 Hz, 2H), 2.36 (t, J=7.0 Hz, 2H), 2.21 (m, 2H), 2.11 (m, 2H), 1.60 (s, 6H), 1.30 (s, 6H), 1.27 (s, 6H). $^{13}$C NMR (75 MHz, CDCl$_3$): 50171.02, 154.98, 148.71, 145.44, 134.03, 129.86, 128.70, 127.33, 127.20, 124.77, 124.07, 121.85, 121.45, 119.71, 107.17, 56.52, 50.19, 48.69, 44.37, 30.69, 28.70, 28.16, 27.27, 18.00.

Compound EL931-122

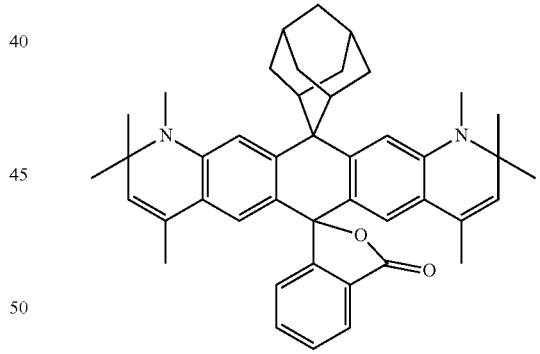

Compound EL931-122 was synthesized by condensing 7,7'-tricyclo[3.3.1.1³,⁷]decane-2,2-diylbis(1,2,2,4-tetramethyl-1,2-dihydroquinoline) (Example 32) and phthalic anhydride according to method A. Silica gel column purification: 20% (v/v) acetone in dichloromethane. Yield: 12.5%, off-white solid. $^1$H NMR (300 MHz, CDCl$_3$): δ 7.98 (dd, J$_1$=6.5 Hz, J$_2$=1.7 Hz, 1H), 7.50 (m, 2H), 6.91 (s, 2H), 6.65 (dd, J$_1$=6.3 Hz, J$_2$=1.5 Hz, 1H), 6.14 (s, 2H), 5.10 (d, J=1.2 Hz, 2H), 3.49 (br s, 1H), 3.25 (br s, 1H), 3.21 (br s, 1H), 2.92 (br s, 1H), 2.87 (s, 6H), 1.96 (br s, 1H), 1.92 (br s, 1H), 1.85 (br s, 2H), 1.70 (m, 2H), 1.58 (br s, 4H), 1.49 (d, J=0.9 Hz, 6H), 1.33 (s, 6H), 1.20 (s, 6H). $^{13}$C NMR (75 MHz, CDCl$_3$): δ 171.59, 155.86, 154.04, 143.25, 133.26, 128.78, 128.65, 127.58, 127.14, 125.80, 124.45, 124.32, 118.77, 109.86, 91.36, 56.50, 49.78, 43.31, 38.50, 36.49, 33.52, 31.79, 30.62, 27.79, 27.46, 27.31, 17.95.

Compound EL931-065

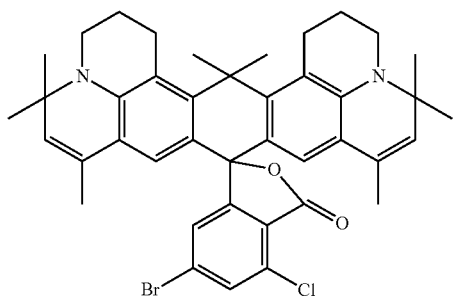

Compound EL931-065 was synthesized by condensing 10,10'-propane-2,2-diylbis(5,5,7-trimethyl-2,3-dihydro-1H,5H-pyrido[3,2,1-ij]quinoline) (Example 10) and 5-bromo-3-chlorophthalic anhydride (Example 34) according to method A as a 10:2 mixture of two isomers. Purification: Silica gel column (40% (v/v) acetone in dichloromethane) followed by trituration in acetone and filtration. Yield (main isomer): 56%, light green solid. $^1$H NMR (300 MHz, CDCl$_3$): δ 7.55 (d, J=1.2 Hz, 1H), 6.94 (d, J=1.2 Hz, 1H), 6.27 (s, 2H), 5.26 (d, J=0.9 Hz, 2H), 3.38 (t, J=5.9 Hz, 4H), 2.90 (m, 4H), 22.07 (s, 3H), 2.01 (s, 3H), 1.99 (m, 4H), 1.70 (s, 6H), 1.32 (s, 6H), 1.28 (s, 6H). $^{13}$C NMR (75 MHz, CDCl$_3$): δ 167.63, 161.03, 148.14, 143.77, 132.87, 132.81, 130.86, 129.47, 127.75, 125.77, 122.52, 121.66, 120.72, 119.44, 115.47, 88.39, 56.45, 43.18, 37.13, 34.92, 33.90, 29.0927.52, 26.46, 21.77, 18.61.

Compounds EL925-124-1 and EL925-124-2

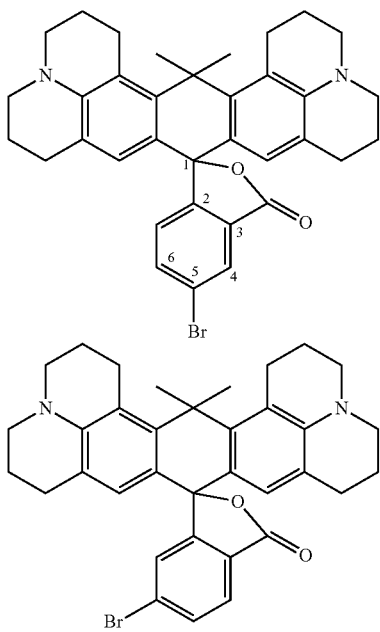

A mixture of compounds EL925-124-1 and EL925-124-2 (5-bromo- and 6-bromo-isomers, respectively) was synthesized by condensing 8,8'-propane-2,2-diylbis(2,3,6,7-tetrahydro-1H,5H-pyrido[3,2,1-ij]quinoline) (Example 7) and 4-bromophthalic anhydride according to method B. Silica gel column purification: 10% (v/v) methanol in dichloromethane. Yield (5-bromo isomer): 35%, dark blue solid. $^1$H NMR (300 MHz, CDCl$_3$): δ 8.09 (br s, 1H), 7.62 (dd, J$_1$=8.1 Hz, J$_2$=1.8 Hz, 1H), 6.91 (d, J=8.1 Hz, 1H), 6.11 (s, 2H), 3.20 (m, 8H), 2.91 (m, 4H), 2.49 (m, 4H), 2.05 (s, 3H), 2.00 (s, 3H), 1.95 (t, J=6.2 Hz, 4H), 1.85 (m, 4H). Yield (6-bromo isomer): 26%, dark blue solid. $^1$H NMR (300 MHz, CDCl$_3$): δ 7.81 (d, J=8.1 Hz, 1H), 7.60 (dd, J$_1$=8.1 Hz, J$_2$=1.5 Hz, 1H), 7.15 (d, J=1.5 Hz, 1H), 6.11 (s, 2H), 3.20 (m, 8H), 2.91 (m, 4H), 2.49 (m, 4H), 2.06 (s, 3H), 2.00 (s, 3H), 1.95 (t, J=6.2 Hz, 4H), 1.85 (m, 4H).

Compound EL931-130

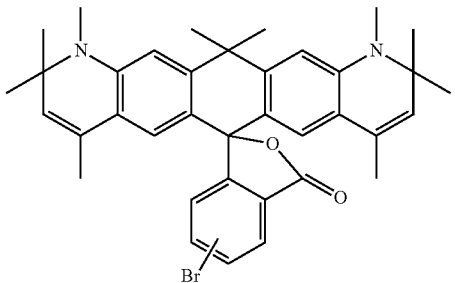

Compound EL931-130 was synthesized by condensing 7,7'-propane-2,2-diylbis(1,2,2,4-tetramethyl-1,2-dihydroquinoline) (Example 9) and 4-bromophthalic anhydride according to method B as a 2:3 mixture of 5- and 6-bromo isomers. Silica gel column purification: 5-10% (v/v) methanol in dichloromethane. Yield (mixture of isomers): 44%, blue-green solid. $^1$H NMR (300 MHz, CDCl$_3$) (5-bromo-isomer): δ 8.09 (d, J=1.8 Hz, 1H), 7.62 (dd, J$_1$=8.7 Hz, J$_2$=2.1 Hz, 1H), 6.88 (d, J=8.1 Hz, 1H), 6.24 (s, 2H), 5.24 (s, 2H), 3.38 (t, J=5.8 Hz, 4H), 2.91 (m, 4H), 2.05 (s, 3H), 2.02 (s, 3H), 1.99 (m, 4H), 1.30 (s, 6H), 1.28 (s, 6H). $^1$H NMR (300 MHz, CDCl$_3$) (6-bromo-isomer): δ 7.81 (d, J=8.1 Hz, 1H), 7.58 (dd, J$_1$=8.1 Hz, J$_2$=1.8 Hz, 1H), 7.10 (d, J=1.8 Hz, 1H), 6.25 (s, 2H), 5.24 (s, 2H), 3.38 (t, J=5.8 Hz, 4H), 2.91 (m, 4H), 2.07 (s, 3H), 2.02 (s, 3H), 1.99 (m, 4H), 1.32 (s, 6H), 1.28 (s, 6H).

Compounds EL931-024-1 and EL931-024-2

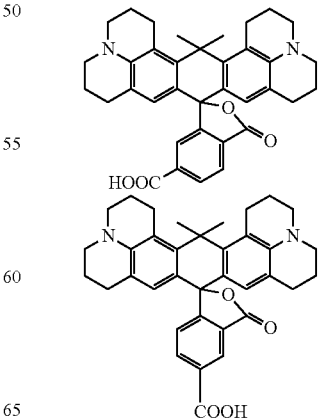

Compounds EL925-024-1 and EL925-024-2 were synthesized by condensing 8,8'-propane-2,2-diylbis(2,3,6,7-tetrahydro-1H,5H-pyrido[3,2,1-ij]quinoline) (Example 7) and trimellitic anhydride as a 1:2 mixture of (6- and 5-carboxyl isomers) according to a modified method A as detailed below.

A mixture of trimellitic anhydride (0.144 g, 0.75 mmol), anhydrous AlCl$_3$ (0.20 g, 1.5 mmol) and anhydrous 1,2-dichloroethane was stirred at 60° C. for approx. 1 h until most of the solids were dissolved. The obtained solution was added to a stirred solution of 8,8'-propane-2,2-diylbis(2,3,6,7-tetrahydro-1H,5H-pyrido[3,2,1-ij]quinolone) (Example 7) (0.193 g, 0.5 mmol) and AlCl$_3$ (0.133 g, 1 mmol) in 1,2-dichloroethane (2 mL). The resultant brown mixture was agitated for 1 h, then concentrated, re-dissolved in methanol (5 mL) and diluted with water (5 mL). After being stirred for 2 hrs the dark blue mixture was concentrated and treated with 1 M HCl (20 mL). The liquid phase was decanted to yield a semi-solid residue which was then re-suspended in water and filtered. Washing the collected solid with water and drying under vacuum afforded 0.15 g (53%) of the desired dye (mixture of isomers) as a dark blue solid. Analytical samples of pure isomers were prepared by silica gel column chromatography eluting with a gradient of methanol in dichloromethane. $^1$H NMR (300 MHz, CD$_3$OD) (minor, 6-bromo-isomer): δ 8.21 (skewed dd, J$_1$=8.1 Hz, J$_2$=1.5 Hz, 1H), 8.16 (skewed d, J=8.1 Hz, 1H), 7.72 (d, J=0.9 Hz, 1H), 6.53 (s, 2H), 3.55 (t, J=6 Hz, 4H), 3.49 (t, J=5.5 Hz, 4H), 3.09 (m, 4H), 2.52 (t, J=6 Hz, 4H), 2.07 (s, 3H), 2.04 (m, 4H), 2.02 (s, 3H), 1.89 (m, 4H). $^1$H NMR (300 MHz, CD$_3$OD) (major, 5-bromo-isomer): δ 8.75 (d, J=1.5 Hz, 1H), 8.20 (dd, J$_1$=7.9 Hz, J$_2$=1.7 Hz, 1H), 7.22 (d, J=8.1 Hz, 1H), 6.54 (s, 2H), 3.55 (t, J=6 Hz, 4H), 3.49 (t, J=5.5 Hz, 4H), 3.09 (m, 4H), 2.52 (t, J=6 Hz, 4H), 2.07 (s, 3H), 2.04 (m, 4H), 2.02 (s, 3H), 1.89 (m, 4H).

Compounds EL925-109-1 and EL925-109-2

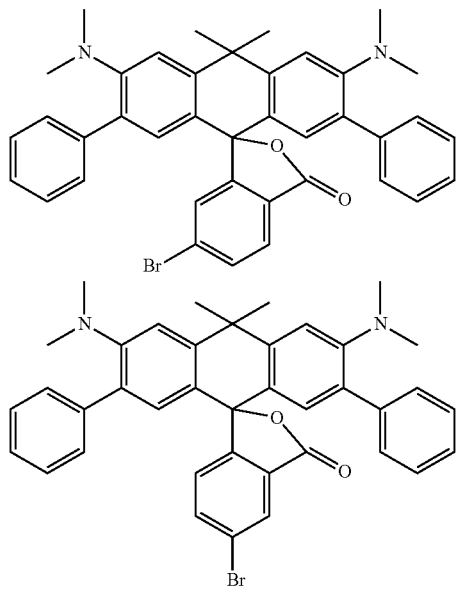

Compounds EL925-109-1 and EL925-109-2 was synthesized by condensing 4,4'-propane-2,2-diylbis(2-(N,N-dimethyl)aminobiphenyl) (Example 5) and 4-bromophthalic anhydride according to method B as a 1:1 mixture of 5- and 6-bromo isomers. Yield (mixture of isomers): 85%, tan solid. Analytical samples of pure isomers were prepared by silica gel column chromatography eluting with dichloromethane. $^1$H NMR (300 MHz, CDCl$_3$) (6-bromo-isomer): δ 7.77 (d, J=8.1 Hz, 1H), 7.59 (dd, J$_1$=8.2 Hz, J$_2$=1.6 Hz, 1H), 7.45-7.20 (aromatic protons, 10H), 7.18 (s, 2H), 6.52 (s, 2H), 2.59 (s, 12H), 1.92 (s, 3H), 1.86 (s, 3H). $^1$H NMR (300 MHz, CDCl$_3$) (5-bromo-isomer): δ 8.03 (d, J=1.5 Hz, 1H), 7.63 (dd, J$_1$=8.1 Hz, J$_2$=1.8 Hz, 1H), 7.45-7.20 (aromatic protons, 10H), 7.19 (s, 2H), 6.97 (d, J=8.1 Hz, 1H), 6.50 (s, 2H), 2.59 (s, 12H), 1.92 (s, 3H), 1.86 (s, 3H).

Example 36. Preparation of Amide-Substituted Carborhodamine Dyes

Compound EL925-133

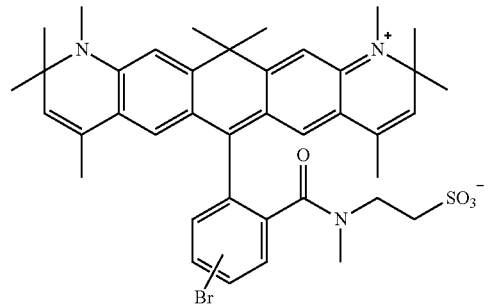

To a solution of EL925-130 (0.34 g, 0.54 mmol) an anhydrous DMF (7 mL) was added triethylamine (0.7 mL) followed by pentafluorophenyl trifluoroacetate (0.25 mL) in three portions over the course of 3 hrs. The resultant solution of the dye PFP ester was cooled to approx. 5° C. and treated with a solution of N-methyltaurine, sodium salt (0.44 g, 2.73 mmol) in water (1.4 mL). The reaction was stirred for 3 hrs and then concentrated to dryness. The obtained solid was extracted with 10% (v/v) methanol in dichloromethane and the washings concentrated to a dark green-blue solid. The crude product was chromatographed on silica eluting with a gradient of methanol (5-20%, v/v) in dichloromethane to afford 0.29 g (72%) of compound EL925-133 (mixture of isomers and rotamers) as a dark green amorphous solid. Absorption maximum: 685 nm (50 mmol Tris-HCl, pH 8.5). $^1$H NMR (300 MHz, CDCl$_3$) (mixture of 5-, 6-bromo and —C(═O)N(CH$_3$)— rotational isomers): consistent with the assigned structure.

Example 37. Preparation of Phosphonylated Carborhodamine Dyes

Compound EL931-049

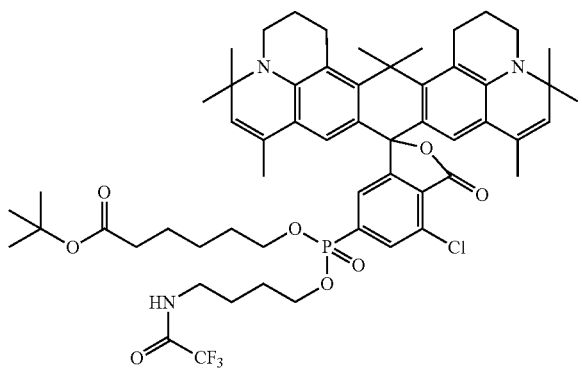 [SMILES: CC1=CC(C)(C)N2CCCc3c2c1cc1c3C(C)(C)c2c(cc3c4c2CCCN4C(C)(C)C=C3C)C12OC(=O)c1c(Cl)cc(P(=O)(OCCCCCC(=O)OC(C)(C)C)OCCCCNC(=O)C(F)(F)F)cc12]

A mixture of palladium (II) acetate (89.6 mg, 0.4 mmol), 1,1'-bis(diphenylphosphino)ferrocene (dppf) (0.444 g, 0.8 mmol), THF (40 mL), triethylamine (0.83 mL, 6 mmol) and potassium acetate (40 mg, 0.4 mmol) was degassed by sonication (using an ultrasonic bath) under argon and then heated at 60° C. for 20 min. To the resultant solution was added compound EL931-065 (2.84 g, 3.4 mmol) followed by tert-butyl 6-{[oxido(3'-{(tert-butoxycarbonyl)amino}butyl)phosphino]oxy}hexanoate (Example 1 in U.S. Pat. No. 8,163,910) (2.5 g, 6 mmol). The reaction was stirred under argon at 70° C. for 5 hrs then cooled and concentrated. The obtained material was chromatographed on silica eluting with a gradient of acetone 50-70% (v/v) in dichloromethane to afford 3.5 g (98%) of compound EL931-049 as an amorphous green solid. $^1$H NMR (300 MHz, CDCl$_3$): δ 7.77 (dd, J$_1$=12.9 Hz, J$_2$=0.9 Hz, 1H), 7.29 (dd, J$_1$=12.9 Hz, J$_2$=0.9 Hz, 1H), 6.97 (br s, 1H), 6.18 (s, 2H), 5.25 (d, J=1.2 Hz, 2H), 4.10-3.85 (m, 4H), 3.38 (t, J=6 Hz, 4H), 3.32 (m, 2H), 2.92 (m, 4H), 2.18 (t, J=7.3H, 2H), 2.06 (s, 3H), 2.02 (s, 3H), 2.00 (m, 4H), 1.63 (d, J=1.2 Hz, 6H), 1.7-1.5 (m, 8H), 1.43 (s, 9H), 1.38-1.22 (m, 2H), 1.31 (s, 6H), 1.26 (s, 6H). $^{31}$P NMR (121.5 MHz, CDCl$_3$): δ 16.20.

Compound EL931-052

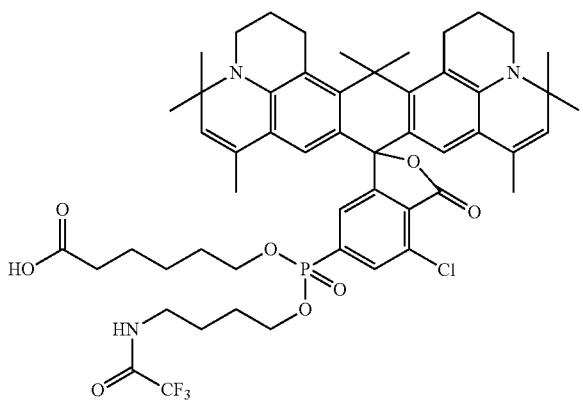 [SMILES: CC1=CC(C)(C)N2CCCc3c2c1cc1c3C(C)(C)c2c(cc3c4c2CCCN4C(C)(C)C=C3C)C12OC(=O)c1c(Cl)cc(P(=O)(OCCCCCC(=O)O)OCCCCNC(=O)C(F)(F)F)cc12]

To a solution of compound EL931-049 (3.5 g, 3.4 mmol) in dichloromethane (25 mL) was added a mixture of trifluoroacetic acid (TFA) (25 mL) and water (1 mL). After being stirred at room temperature for 1 h the reaction was concentrated to a dark oil. Most of the residual TFA was removed by co-evaporation with dichloromethane followed by precipitation (from ethyl acetate) into hexane. Drying under reduced pressure afforded compound EL931-052 (TFA salt) as a dark green amorphous solid (100% yield). $^1$H NMR (300 MHz, DMSO-d6): δ 9.41 (t, J=5.4 Hz, 1H), 8.01 (dd, J$_1$=13.4 Hz, J$_2$=1.0 Hz, 1H), 7.60 (d, J=12.3 Hz, 1H), 6.38 (d, J=0.9 Hz, 2H), 5.60 (s, 2H), 4.00 (m, 4H), 3.67 (unresolved t, 4H), 3.14 (m, 2H), 3.01 (unresolved t, 4H), 2.09 (t, J=7.5H, 2H), 1.98 (s, 3H), 1.94 (s, 3H), 1.95 (m, 4H), 1.55 (s, 6H), 1.6-1.35 (m, 8H), 1.46 (s, 6H), 1.43 (s, 6H), 1.25 (m, 2H).

Compound EL931-054

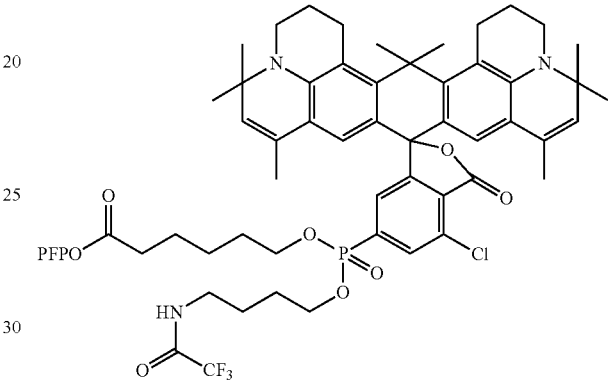

Pentafluorophenyl trifluoroacetate (1 mL, 5.6 mmol) was added to a solution of compound EL931-052 (3.4 mmol) and triethylamine (5 mL, 36.3 mmol) in anhydrous dichloromethane (100 mL). After being stirred for 30 min the reaction was washed with 10% citric acid solution, dried over Na$_2$SO$_4$ and concentrated. The resultant material was chromatographed on silica eluting with acetone to afford 3.65 g (93%) of compound EL931-054 as a dark green amorphous solid. $^1$H NMR (300 MHz, CDCl$_3$): δ 7.81 (d, J=13.2 Hz, 1H), 7.36 (d, J=13.2 Hz, 1H), 7.07 (br s, 1H), 6.30 (d, J=3.9 Hz, 2H), 5.27 (d, J=0.9 Hz, 2H), 4.03 (m, 4H), 3.44 (t, J=5.7 Hz, 4H), 3.31 (m, 2H), 2.93 (m, 4H), 2.64 (t, J=7.3 Hz, 2H), 2.04 (s, 3H), 2.01 (s, 3H), 1.99 (m, 4H), 1.8-1.6 (m, 8H), 1.63 (s, 6H), 1.45 (m, 2H), 1.35 (s, 6H), 1.32 (s, 6H).

Compound EL931-076

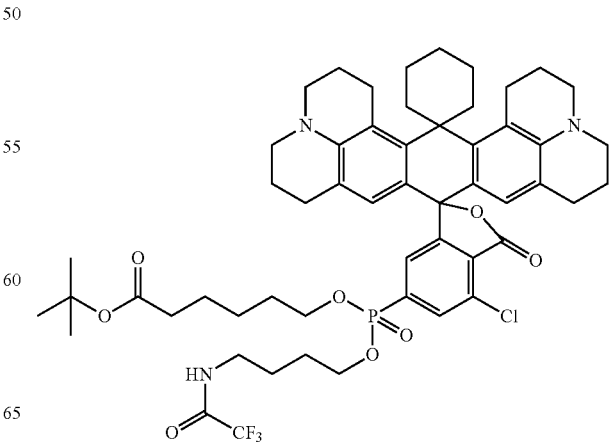

Compound EL931-076 was synthesized by analogy with compound EL931-049 staring from compound EL931-069 and purified on silica eluting with 10-20% (v/v) methanol in dichloromethane in 61% yield as a dark green amorphous solid. $^1$H NMR (300 MHz, CDCl$_3$): δ 8.37 (br s, 1H), 7.76 (d, J=13.2 Hz, 1H), 7.25 (d, J=13.2 Hz, 1H), 6.47 (s, 3H), 6.45 (s, 3H), 4.03 (m, 4H), 3.45 (m, 8H), 3.34 (m, 2H), 3.09 (m, 4H), 2.7-2.3 (m, 8H), 2.20 (t, J=7.3 Hz, 2H), 2.15-1.175 (m, 8H), 1.75-1.55 (m, 10H), 1.43 (s, 9H), 1.55-1.35 (m, 4H). $^{31}$P NMR (121.5 MHz, CDCl$_3$): δ 17.05.

Compound EL931-056

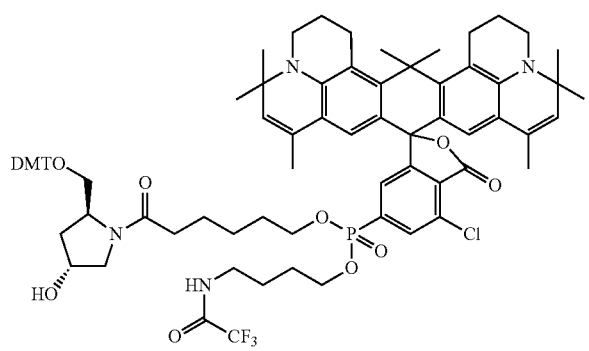

g (1.38 mmol) of compound EL931-054. The reaction was agitated for 30 min and then concentrated. The resultant material was dissolved in ethyl acetate, washed with dilute NaHCO$_3$ solution, brine and dried over Na$_2$SO$_4$. The extract was concentrated and the obtained material chromatographed on silica eluting with 10-30% (v/v) methanol in dichloromethane to afford 1.70 g (88%) of compound EL931-065 as a dark green amorphous solid. $^1$H NMR (300 MHz, DMSO-d6) (mixture of —N(C=O)— rotomers): δ 9.38 (t, J=5.3 Hz, 1H), 7.87 (d, J=12.6 Hz, 1H), 7.31 (m, 4H), 7.20 (m, 6H), 6.86 (m, 4H), 6.04 (s, 2H), 5.31 (s, 2H), 5.00 (d, J=4.2 Hz, 0.7H), 4.92 (d, J=4.2 Hz, 0.3H), 4.42-4.25 (m, 1H), 4.20-4.02 (m, 1H), 3.92 (m, 4H), 3.72-3.69 (three s, 6H), 3.58-3.40 (m, 1H), 3.31 (m, 6H), 3.09 (m, 2H), 3.00 (m, 1H), 2.87 (m, 4H), 2.12 (m, 2H), 2.05 (m, 2H), 1.98 (s, 3H), 1.94 (s, 3H), 1.88 (m, 4H), 1.52 (s, 6H), 1.51-1.30 (m, 8H), 1.23 (s, 12H), 1.20 (m, 2H). $^{31}$P NMR (121.5 MHz, DMSO-d6): δ 14.59.

Example 38. Preparation of Carborhodamine-Modified Oligonucleotide Synthesis Supports Compound EL931-059

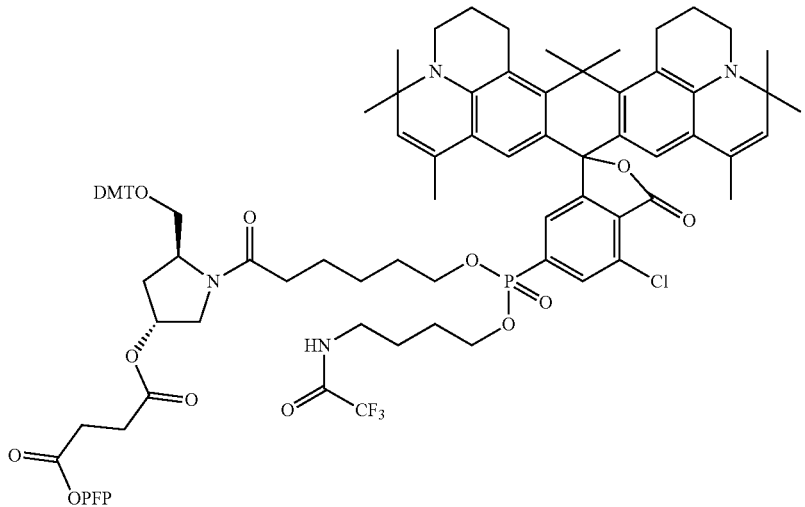

(Step 1) Preparation of 5-dimethoxytrityloxymethyl-3-hydroxypyrrolidine

A solution of N-Fmoc-5-dimethoxytrityloxymethyl-3-hydroxypyrrolidine (U.S. Pat. No. 6,828,427) (1.1 g, 1.71 mmol) in a mixture of DMF (10 ml) and triethylamine (10 ml) was heated at 80° C. for 1 h then concentrated to an oil and re-dissolved in DMF (12 ml) and TEA (0.5 ml). The solution of crude 5-dimethoxytrityloxymethyl-3-hydroxypyrrolidine was promptly used in the next step without additional purification.

(Step 2) Coupling of compound EL931-054 with 5-dimethoxytrityloxymethyl-3-hydroxypyrrolidine The solution of 5-dimethoxytrityloxymethyl-3-hydroxypyrrolidine from step 1 was added into a flask containing 1.6

(1) Succinylation of Compound EL931-056

Succinic anhydride (100 mg, 1 mmol) was added to a solution of compound EL931-056 (0.84 g, 0.6 mmol), triethylamine (0.3 mL, 2.2 mmol) and N-methylimidazole (0.05 mL) in anhydrous dichloromethane (10 mL). The reaction was allowed to proceed for 30 hrs until almost no starting material was found by TLC analysis.

(Step 2) Pentafluorophenyl Ester Preparation

To the step 1 solution was added triethylamine (0.1 mL) followed by pentafluorophenyl trifluoroacetate (0.25 mL, 1.44 mmol). The reaction was stirred for 1.5 h and then concentrated. The obtained material was chromatographed on silica eluting with acetone to afford 0.83 g (83%) of compound EL931-059 as a green amorphous solid. $^1$H NMR (300 MHz, DMSO-d6) (mixture of —N(C=O)— rotomers): δ 9.37 (t, J=5.3 Hz, 1H), 7.85 (d, J=12.9 Hz, 1H), 7.31 (m, 4H), 7.20 (m, 6H), 6.86 (m, 4H), 6.04 (s, 2H), 5.40 (m, 1H), 5.30 (d, J=1.8 Hz, 2H), 4.20 (m, 1H), 3.92 (m, 4H), 3.80-3.60 (m, 1H), 3.72-3.69 (three s, 6H), 3.50 (m, 1H), 3.32 (m, 6H), 3.15 (m, 1H), 3.09 (m, 4H), 2.87 (m, 4H), 2.73 (t, J=6.1 Hz, 2H), 2.20 (m, 2H), 2.12 (m, 2H), 1.97 (s, 3H), 1.94 (s, 3H), 1.88 (m, 4H), 1.52 (s, 6H), 1.51-1.30 (m, 8H), 1.23 (s, 12H), 1.20 (m, 2H). $^{31}$P NMR (121.5 MHz, DMSO-d6): δ 14.59.

Polystyrene Support EL931-063

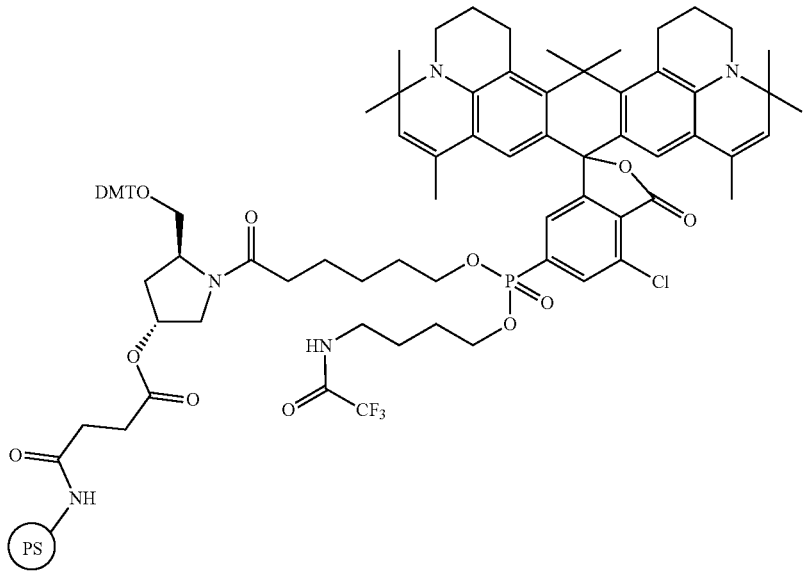

Aminomethyl-polystyrene support (33 μmol/g amine capacity, Applied Biosystems, PN 360865C) (6.0 g) was added to a solution of compound EL931-059 (0.22 g, 0.132 mmol, 22 μmol/g offering) and triethylamine (0.5 mL) in DMF (30 ml). The suspension was swirled on an orbital shaker for 18 hrs then filtered and washed with DMF. To block unreacted amino groups the support was suspended in pyridine (20 mL), treated with acetic anhydride (2 mL) and swirled for 30 min. The blocking reagents were removed by filtration and the support was washed with several 50 mL portions of acetonitrile followed by drying under reduced pressure to afford polystyrene support polystyrene support EL931-063. DMT loading was 20.3 μmol/g according to a colorimetric acid cleavage test.

Controlled Pore Glass Support EL931-064

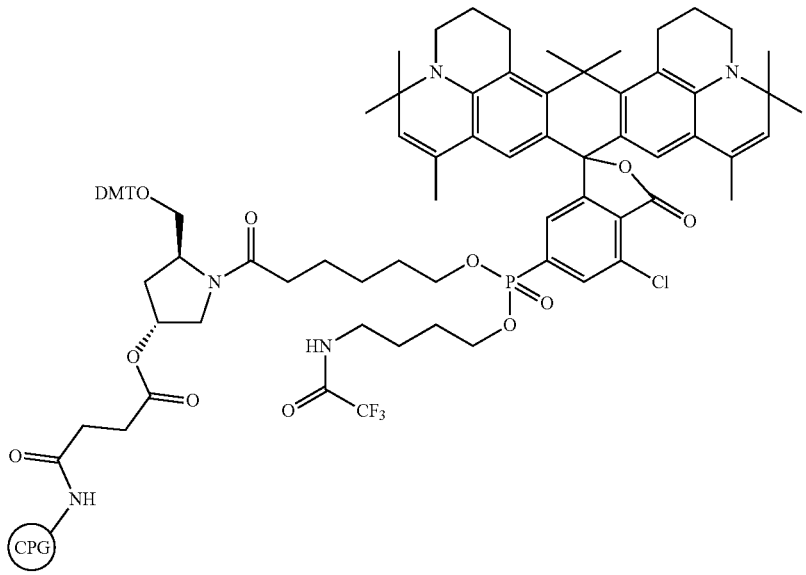

Long Chain Alkylamine Controlled Pore Glass support (1000 Angstrom pore size, 90 μmol/g amine capacity) (6.0 g) was added to a solution of compound EL931-059 (0.329 g, 0.198 mmol, 33 μmol/g offering) and triethylamine (0.5 mL) in DMF (30 ml). The suspension was swirled on an orbital shaker for 18 hrs then filtered and washed with DMF. To block unreacted amino groups the support was suspended in pyridine (20 mL), treated with acetic anhydride (2 mL) and swirled for 30 min. The blocking reagents were removed by filtration and the support was washed with several 50 mL portions of acetonitrile followed by drying under reduced pressure to afford Controlled Pore Glass support EL931-064. DMT loading was 25.5 μmol/g according to a colorimetric acid cleavage test.

Polystyrene Support EL925-190

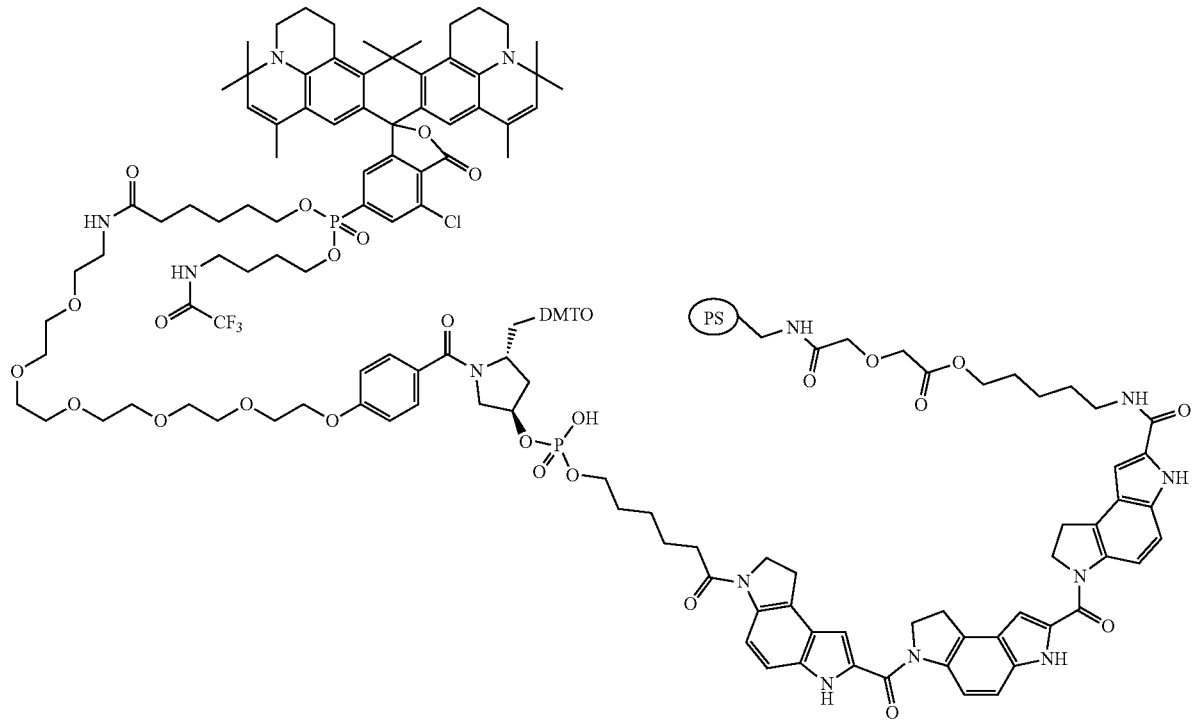

A solution of compound EL931-054 (0.10 g, 0.086 mmol) and triethylamine (0.1 mL) in dichloromethane (16 mL) was added to a flask containing amine-modified Minor Groove Binder polystyrene support (FIG. 6, prepared using the compounds described in U.S. Pat. No. 7,759,126). The suspension was swirled for 18 hrs, then filtered, washed with dichloromethane, re-suspended in pyridine (18 mL) and treated with acetic anhydride (2 mL). After being swirled for 30 min the polystyrene support was filtered, washed with acetonitrile and dried under high vacuum.

Example 39. Preparation of Carborhodamine Phosphoramidites

Compound EL931-061

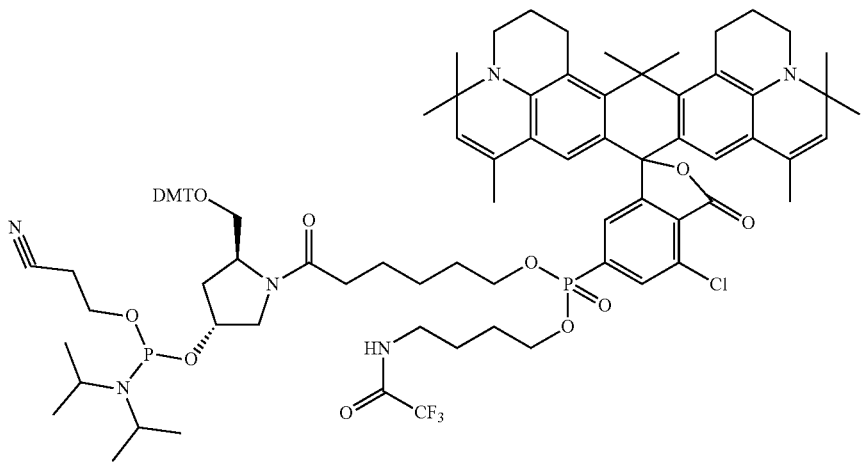

To a solution of compound EL931-056 (0.84 g, 0.6 mmol) in anhydrous dichloroethane (10 mL) was added N,N-diisopropylammonium tetrazolide (0.1 g, 0.6 mmol) followed by 2-cyanoethyl N,N,N',N'-tetraisopropylphosphorodiamidite (0.27 mL, 0.85 mmol). The retraction was stirred for 18 hrs, then concentrated and partioned between saturated NaHCO$_3$ solution and ethyl acetate. The organic phase was washed with brine, dried over Na$_2$SO$_4$ and concentrated. The crude product was precipitated from ethyl acetate to pentane and dried under reduced pressure to afford 0.9 g (94%) of compound EL931-061 as a light green solid. $^{31}$P NMR (121.5 MHz, DMSO-d6) (mixture of diastereomers and rotomers): δ 146.61, 146.44, 146.25, 145.92, 16.18.

Compound EL931-126

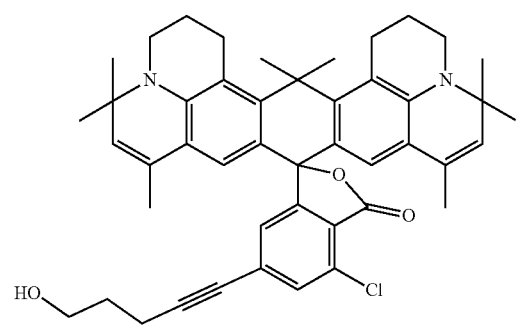 [SMILES: CC1=CC(C)(C)N2CCCc3c2c1cc1c3C(C)(C)c2c(cc3c4c2CCCN4C(C)(C)C=C3C)C12OC(=O)c1c(Cl)cc(C#CCCCO)cc12]

To a flask charged with compound EL931-065 (1.0 g, 1.4 mmol), bis(triphenylphosphine)palladium chloride (49 mg, 0.07 mmol) and copper (I) iodide (29 mg, 0.155 mmol) under argon was added a degasses mixture of THF (10 mL) and diisopropylethylamine (1.44 mL) followed by 4-pentyn-1-ol (0.168 g, 2 mmol). The reaction was stirred at 50° C. for 24 hrs then cooled and concentrated. The obtained residue was partitioned between dichloromethane and water. The dichloromethane phase was dried (Na$_2$SO$_4$) and concentrated to an oil, which was then chromatographed on silica eluting with 40% (v/v) acetone in dichloromethane. Yield: 0.84 g (84%), green amorphous solid. $^1$H NMR (300 MHz, DMSO-d6): δ 7.64 (d, J=0.9 Hz, 1H), 6.85 (d, J=0.9 Hz, 1H), 6.06 (s, 2H), 5.34 (d, J=1.2 Hz, 2H), 4.49 (t, J=5.3 Hz, 1H), 3.42 (m, 2H), 3.33 (m, 4H), 2.87 (m, 4H), 2.42 (t, J=7.2 Hz, 2H), 1.98 (s, 3H), 1.92 (s, 3H), 1.89 (m, 4H), 1.60 (m, 2H), 1.55 (d, J=1.2 Hz, 6H), 1.25 (s, 12H).

Compound EL931-128

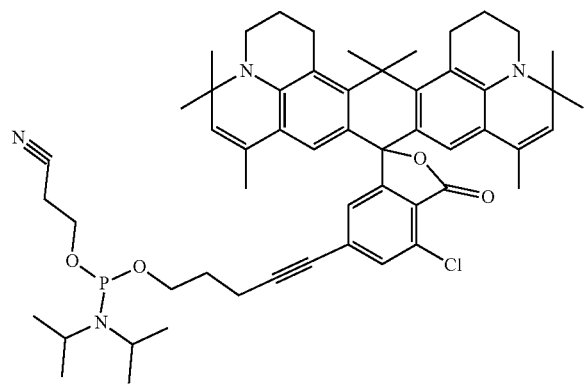 [SMILES: CC1=CC(C)(C)N2CCCc3c2c1cc1c3C(C)(C)c2c(cc3c4c2CCCN4C(C)(C)C=C3C)C12OC(=O)c1c(Cl)cc(C#CCCCOP(OCCC#N)N(C(C)C)C(C)C)cc12]

To a solution of compound EL931-126 (0.81 g, 1.1 mmol) in anhydrous dichloroethane (20 mL) was added N,N-diisopropylammonium tetrazolide (0.2 g, 1.2 mmol) followed by 2-cyanoethyl N,N,N',N'-tetraisopropylphosphorodiamidite (0.73 mL, 2.3 mmol). The retraction was stirred for 5 hrs, then concentrated and portioned between saturated NaHCO$_3$ solution and ethyl acetate. The organic phase was washed with brine, dried over Na$_2$SO$_4$ and concentrated. The crude product was chromatographed on silica eluting with 40-100% ethyl acetate in hexane. Yield: 0.42 g (42%), green amorphous solid. $^1$H NMR (300 MHz, DMSO-d6): δ 7.63 (d, J=0.9 Hz, 1H), 6.80 (d, J=0.9 Hz, 1H), 6.05 (s, 2H), 5.33 (d, J=1.2 Hz, 2H), 3.66 (m, 4H), 3.43 (m, 2H), 3.33 (m, 4H), 2.86 (m, 4H), 2.69 (t, J=5.9 Hz, 2H), 2.47 (t, J=6.6 Hz, 2H), 1.98 (s, 3H), 1.93 (s, 3H), 1.89 (m, 4H), 1.74 (m, 2H), 1.55 (d, J=1.2 Hz, 6H), 1.24 (s, 12H), 1.06 (d, J=6.9 Hz, 6H), 0.96 (d, J=6.9 Hz, 6H). $^{31}$P NMR (121.5 MHz, DMSO-d6): δ 145.70.

Example 40: Absorption and Fluorescence Spectra of Exemplary Carborhodamine Compounds Absorption and fluorescence spectra of exemplary compounds and conjugates in accordance with preferred embodiments of the present disclosure, as shown in FIGS. 11A-11E, were obtained using the instrumentations and measurement conditions described in Table 2 below.

TABLE 2

| Instrumentation and measurement conditions | |
|---|---|
| Instruments | UV-VIS: PE Lambda 2S UV-VIS spectrophotometer |
| | Fluorescence: Varian Cary Eclipse Fluorimeter |
| Conc. (mM) | UV-VIS: 10-30 |
| | Fluorescence: 0.1-0.3 |
| Solvent | Methanol |

Example 41. Oligonucleotide Synthesis

Oligonucleotides and oligonucleotide conjugates were synthesized using the instrumentation and synthesis conditions described in Table 3 below.

TABLE 3

| Instrumentation and synthesis conditions | |
|---|---|
| Instrument | ABI 3900 DNA synthesizer |
| Scale | 200 nmol |
| Deblocking | 3% TCA |
| Amidite conc./ coupling time | 50 mM (double amidite addition with total of 3 min coupling time for all dye amidites) |
| Activator | 5-Ethylthiotetrazole |
| Oxidation | I$_2$/Pyridine/Water |
| Capping | Ac$_2$O/Pyridine/MeIm |
| Deprotection | tert-Butylamine:MeOH:water, 1:2:1 (v/v/v), 55° C., 16 hrs or 70° C., 3 hrs. |
| Purification | 4.6 × 250 mm Luna C18 RP HPLC (2 mL/min, gradient of CH$_3$CN, triethylammonium bicarbonate buffer, pH ~9) |
| Mass spectroscopy | Thermo Scientific, LCQ Fleet, ESI (TEA-HFIPA buffer) |

The mass spectrometry for the synthesized oligonucleotide probes is listed in Table 4 below.

TABLE 4

| Summary of Mass Spectrometry data for synthesized oligonucleotide probes | | | | |
|---|---|---|---|---|
| ID | Sequence (5'-3') | Calc MW | Found MW | % Purity |
| IC1 | (EL931-190)-G*CAA AGTCCCATCGTT-Q575 (SEQ ID NO: 1) | 7655.0 | 7654.0 | 96.5 |

TABLE 4-continued

Summary of Mass Spectrometry data for synthesized oligonucleotide probes

| ID | Sequence (5'-3') | Calc MW | Found MW | % Purity |
|---|---|---|---|---|
| OXA | (EL931-054)-G*GTG GCATCGATTATC-Q575-MGB (SEQ ID NO: 2) | 7342.7 | 7341.8 | 100 |

G* is Super G®: 4-hydroxy-6-amino pyrazolopyrimidine; Q575 is a universal non-fluorescent quencher with an absorbance maximum of 575 nm (Quencher-575, ELITechGroup, Bothell, WA).

Example 42. Real-time PCR Evaluation with a Cleavable Taqman Probe

This example compares the real-time PCR performance an OXA-specific enzymatically cleaved TaqMan probe labeled with EL631-054 and the same probe but now labeled with Cy5.5. The results are shown in FIG. 12, showing similar performance. Monoreagent formulation and PCR conditions are shown in Table 5.

TABLE 5

PCR formulation and PCR conditions

| Instrument | ELITe InGenius |
|---|---|
| OXA primers | AATAAATCAATGCGTGT ATTAGCCTTATCGGC (SEQ ID NO: 3) AATAAATCATTCTTGCC ATTCCTTTGCTACCG (SEQ ID NO: 4) |
| OXA probe | (EL931-054 or Cy5.5)-G*GTGGCATCGATTATC-Q575-MGB (SEQ ID NO:2) |
| Primer concentration (nM) | 500 nM |
| Probe concentration (nM) | 200 nM |
| Master mix | MGB Alert Platinum Master Mix (Elitech M800599) |
| Target concentration | 500 copies/reaction |
| Thermocycling | Precycle: 95° C., 240 sec 45 cycles of PCR: Denature: 95° C., 10 sec Anneal: 56° C., 30 sec Extend: 73° C., 15 sec |

Example 43. Real-Time PCR Evaluation with a MGB Pleades Probe

This method illustrates the performance of an MGB Pleades probe that is not enzymatically cleaved, labeled with either EL631-190 or MGB-AP680. As shown in FIG. 13, the EL631-190 dye showed significantly stronger fluorescent signal than the MGB-AP680. To evaluate preferred embodiments of the new fluorescent dye, monoreagent formulation and PCR conditions are shown in Table 6.

TABLE 6

PCR formulation and PCR conditions

| instrument | ELite inGenius |
|---|---|
| IC1 primers | GCAATCGTATTACCTiCTTATCGCAG (limiting) (SEQ ID NO: 5) CAACCATCGTCATCGTCAGGAAAC (excess) (SEQ ID NO: 6) |
| IC1 Probe | (EL931-190 or MGB-AP680)-G*CAAAGTCCCATCGTT-Q575 (SEQ ID NO: 1) |
| Primer concentration (nM) | 100 nM (limiting) 300 nM (excess) |
| Probe concentration (nM) | 200 nM |
| Master Mix | MGB Alert Platinum Master Mix (Elitech M800599) |
| Target concentration | 10,000 copies/reaction |
| Thermocycling | Precycle: 95° C., 240 sec 45 cycles of PCR: Denature: 95° C., 10 sec Anneal: 56° C., 30 sec |

*AP680 is a fluorescent dye with excitation and emission properties similar to those of Cy5.5 (AquaPhluor 680, ELITechGroup, Bothell, WA)

REFERENCES CITED

The following documents and publications are hereby incorporated by reference.

U.S. and Foreign Patent Documents

PCT Publications

WO 01/38584 and WO 01/64958
US Patent Appl. Nos.
2012/0244535
US Patent No.
RE 38,416
U.S. Pat. No. 3,996,345
U.S. Pat. No. 5,037,994
U.S. Pat. No. 5,419,966
U.S. Pat. No. 5,512,667
U.S. Pat. No. 5,539,082
U.S. Pat. No. 5,585,481
U.S. Pat. No. 5,696,251
U.S. Pat. No. 5,736,626
U.S. Pat. No. 5,801,155
U.S. Pat. No. 5,824,796
U.S. Pat. No. 5,912,340
U.S. Pat. No. 5,942,610
U.S. Pat. No. 6,127,121
U.S. Pat. No. 6,312,894
U.S. Pat. No. 6,727,356
U.S. Pat. No. 6,790,945
U.S. Pat. No. 6,828,159
U.S. Pat. No. 7,045,610
U.S. Pat. No. 7,718,374
U.S. Pat. No. 7,759,126

U.S. Pat. No. 7,767,834
U.S. Pat. No. 7,935,822
U.S. Pat. No. 8,163,910
U.S. Pat. No. 8,293,684
U.S. Pat. No. 9,169,256
U.S. Pat. No. 9,328,384
U.S. Pat. No. 9,464,316
U.S. Pat. No. 9,745,336
Japanese Patent No. 5,665,089

Non-Patent References

Berge, S. M., et al., Journal of Pharmaceutical Science, 66: 1-19 (1977).
Carlson, R. et al. Acta Chemica Scandinavica B 40, 522-533 (1986).
Didenko, Biotechniques, 31(5): 1106-1121 (2001).
Doose S, et al. Chemphyschem. 10(9-10): 1389-98 (2009).
Greene, T. W. and Wuts, P. G., Greene's Protective Groups in Organic Chemistry, Wiley, 4nd ed. (2007).
Grimm et al., ACS Chem. Biology, 8, 1303-1310 (2013).
Harrison and Harrison et al., Compendium of Synthetic Organic Methods, Vols. 1-8, John Wiley and Sons. (1971-1996).
Hymas W C, Hillyard D R J Virol Methods. 156:124-8 (2009).
Hermanson, Bioconjugate Techniques, Elsevier, pp. 664 to 667, 139-140 and 274-275 (1996).
Kim, Y. et al., Int. J. Clin. Exp. Pathol. 1, 105-116 (2008).
Kobayashi, S. et al. Chem. Eur. J., 6 (19), 3491-3494 (2000).
Kolmakov et al., Eur. J. Org. Chem., 3593-3610 (2010).
Kutyavin et al., Current Protocols in Nucleic Acid Chemistry, 8.4.1-8.4-21 (2003).
Lukhtanov et al. Bioconjugate Chemistry, 6: 418-426 (1995).
Lukhtanov et al., Nucl. Acids Res., 35: e30 (2007).
March J. in Advanced Organic Chemistry, Chapter 4", 4th edition John Wiley and Sons, New York, pages 71-124 (1992).
Matayoshi et al., Science, 247:954-958 (1990).
Mathre et al., Encyclopedia of Reagents for Organic Synthesis, 1-18; (2013).
Molander, G. A. et al., Cross Coupling and Heck-Type Reactions. Volumes 1, 2 and 3. (2013) Georg Thieme Verlag K G.
Reddy, et al., Pharmacol. Therap., 84:1-111 (1999).
Riccardo, S. et al. J. Org. Chem., 78(14), 7259-7263 (2013).
Salvio, R. et al. J. Org. Chem., 78(14), 7259-7263 (2013).
Smith, March. Advanced Organic Chemistry 6th ed. by John Wiley & Sons, Inc. pp. 501-502 (2007).
Walker, et al., Biopolymers, 44: 323-334 (1997).
Wemmer, D. E., and Dervan P. B., Current Opinion in Structural Biology, 7:355-361 (1997).
Zimmer, C & Wahnert, U., Prog. Biophys. Molec. Bio. 47: 31-112 (1986).

What is claimed is:

1. An oligonucleotide conjugate comprising:
a carborhodamine compound having a structure of

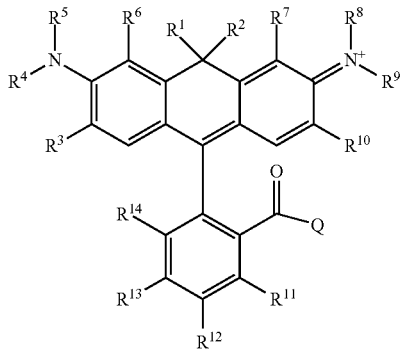

wherein $R^1$ and $R^2$ are independently $(C_1-C_{100})$alkyl or $(C_1-C_{100})$heteroalkyl, or $R^1$ and $R^2$ form a ring structure comprising one or more rings, $R^3$, $R^6$, $R^7$, and $R^{10}$ are independently selected from H, $(C_1-C_{100})$alkyl, $(C_1-C_{100})$heteroalkyl, $(C_1-C_{100})$alkoxy, $(C_1-C_{100})$alkenyl, $(C_1-C_{100})$alkynyl, aryl, heteroaryl, halo, —OR', —OC(O)R', —NR'R", —SR', —OC(O)NR'R", —NR"C(O)R', —NR"C(O)OR', —NR'C(O)NR"R'", and —SO$_2$H, wherein R', R" and R'" are independently selected from H, $(C_1-C_8)$alkyl, $(C_1-C_8)$heteroalkyl, aryl, and heteroaryl, $R^4$, $R^5$, $R^8$, and $R^9$ are independently selected from H, $(C_1-C_{100})$alkyl, $(C_1-C_{100})$heteroalkyl, $(C_1-C_{100})$alkoxy, $(C_1-C_{100})$alkenyl, $(C_1-C_{100})$alkynyl, aryl and heteroaryl, $R^{11}$, $R^{12}$, $R^{13}$ and $R^{14}$ are independently selected from H, $(C_1-C_{100})$alkyl, $(C_1-C_{100})$heteroalkyl, $(C_1-C_{100})$alkoxy, $(C_1-C_{100})$alkenyl, $(C_1-C_{100})$alkynyl, aryl, heteroaryl, halo, —OR$^{iv}$, —OSO$_2$R$^{iv}$, —OC(O) R$^{iv}$, —NR$^{iv}$R$^v$— SR$^{iv}$, —R$^{iv}$, —CN, —NO$_2$, —CO$_2$R$^{iv}$, —CONR$^{iv}$R$^v$, —C(O) R$^{iv}$,—SO$_2$R$^{iv}$, —SO$_2$NR$^{iv}$R$^v$, —N$_3$, —CH(Ph)$_2$, perfluoro$(C_1-C_4)$alkoxy, perfluoro$(C_1-C_4)$alkyl, —P(O)(OR$^{15}$)(OR$^{16}$) and —R$^{21}$-R$^{22}$, wherein Ph is phenyl, wherein R$^{iv}$ and R$^v$ are independently selected from H, $(C_1-C_{20})$alkyl perfluoro$(C_1-C_4)$alkyl, perfluoro $(C_1-C_4)$heteroalkyl, aryl and heteroaryl, and wherein aryl and heteroaryl groups are unsubstituted or substituted, or $R^3$, $R^4$, $R^5$, $R^6$, $R^7$, $R^8$, $R^9$, $R^{10}$, $R^{11}$, $R^{12}$, $R^{13}$ and $R^{14}$ form one or more 4- to 7-member ring systems by bridging between one or more of $R^3$, $R^4$, $R^5$, $R^6$, $R^7$, $R^8$, $R^9$, $R^{10}$, $R^{11}$, $R^{12}$, $R^{13}$ and $R^{14}$, $R^{15}$ is selected from H—, NH$_2$(CH)$_4$-, NH$_2$(CH$_2$)$_5$-, CF$_3$C(O)NR'(CH$_2$)$_4$-, CF$_3$C(O)NR'(CH$_2$)$_5$, (CH$_3$)$_3$COC(O)NR'(CH$_2$)$_4$-, (CH$_3$)$_3$COC(O)NR'(CH$_2$)$_5$-, tert-butyl, methyl, and aryl, wherein R' is selected from H- and $(C_1-C_8)$alkyl, $R^{16}$ is identical to $R^{15}$ or $R^{22}$, $R^{21}$ is a divalent group selected from alkylene, alkenylene, alkynylene, arylene, heteroalkylene, heteroalkenylene, heteroalkynylene, and heteroarylene, where one free valence connects to an aromatic carbon of $R^{11}$, $R^{12}$, $R^{13}$ or $R^{14}$ and one free valence connects to $R^{22}$, Q is -N(R$^{23}$)(R$^{24}$) or OR$^{25}$, $R^{22}$, $R^{23}$, $R^{24}$ are independently selected from $(C_1-C_{100})$alkyl, aryl, $(C_1-C_{100})$heteroalkyl, HOSO$_2$(C$_1$-C$_{100}$)alkyl, heteroaryl or a combination thereof, or $R^{23}$ and $R^{24}$ together form a saturated ring with 0 to 3 heteroatoms, $R^{25}$ is H or is identical to $R^{23}$, and wherein one of $R^{11}$, $R^{12}$, $R^{13}$ and $R^{14}$ is —P(O)(OR$^{15}$)(OR$^{16}$) and one or more hydrocarbon hydrogens in $R^{16}$ is replaced with —C(O)R$^{17}$ or —OR$^{18}$, wherein R$^{17}$ is a nitrogen atom of an alkylamino group in an alkylamine-modified oligonucleotide and R$^{18}$ is a phosphorus atom of a phosphate group in an oligonucleotide;

an oligonucleotide; and a quencher.

2. The oligonucleotide conjugate of claim 1, further comprising a minor groove binder.

3. The oligonucleotide conjugate of claim 1, wherein the carborhodamine compound has a structure of:

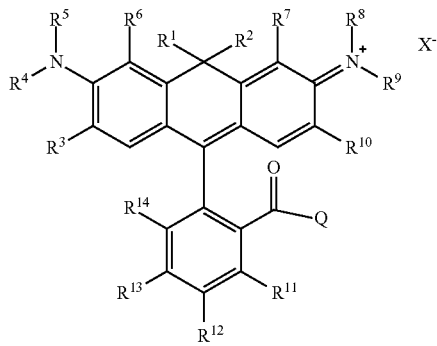

wherein X⁻ is an anionic counter ion.

4. The oligonucleotide conjugate of claim 1 wherein $R^3$, $R^4$, $R^5$, $R^6$, $R^7$, $R^8$, $R^9$, $R^{10}$, $R^{11}$, $R^{12}$, $R^{13}$ and $R^{14}$ form one or more 4- to 7-member ring systems by bridging between one or more of $R^3$ with $R^4$, $R^4$ with $R^5$, $R^5$ with $R^6$, $R^7$ with $R^8$, $R^8$ with $R^9$, $R^9$ with $R^{10}$, $R^{11}$ with $R^{12}$, $R^{12}$ with $R^{13}$, and $R^{13}$ with $R^{14}$.

5. The oligonucleotide conjugate of claim 1 wherein $R^3$, $R^4$, $R^5$, $R^6$, $R^7$, $R^8$, $R^9$, $R^{10}$, $R^{11}$, $R^{12}$, $R^{13}$ and $R^{14}$ form one or more 4- to 7-member ring systems linked to one or more further 4- to 7-member ring systems, and wherein the one or more further 4- to 7-member ring systems comprise up to 3 double bonds.

6. The oligonucleotide conjugate of claim 5, wherein the one or more further 4- to 7-member ring systems comprise heteroatoms.

7. A method for detecting a target nucleic acid sequence in a sample, comprising:
  contacting the sample with the oligonucleotide conjugate of claim 1, wherein the oligonucleotide comprises a nucleic acid sequence at least partially complementary to the target nucleic acid sequence; and
  detecting a fluorescence signal resulting from hybridization of the oligonucleotide conjugate to the target nucleic acid sequence.

8. The method of claim 7, further comprising contacting the sample and the oligonucleotide conjugate with a polymerase enzyme comprising 5'-nuclease activity, wherein the fluorescence signal is generated by the polymerase enzyme.

9. The method of claim 7, wherein the oligonucleotide conjugate is a primer or a probe.

10. The method of claim 7, further comprising amplifying the target nucleic acid sequence.

\* \* \* \* \*

UNITED STATES PATENT AND TRADEMARK OFFICE
CERTIFICATE OF CORRECTION

Figure 11A:
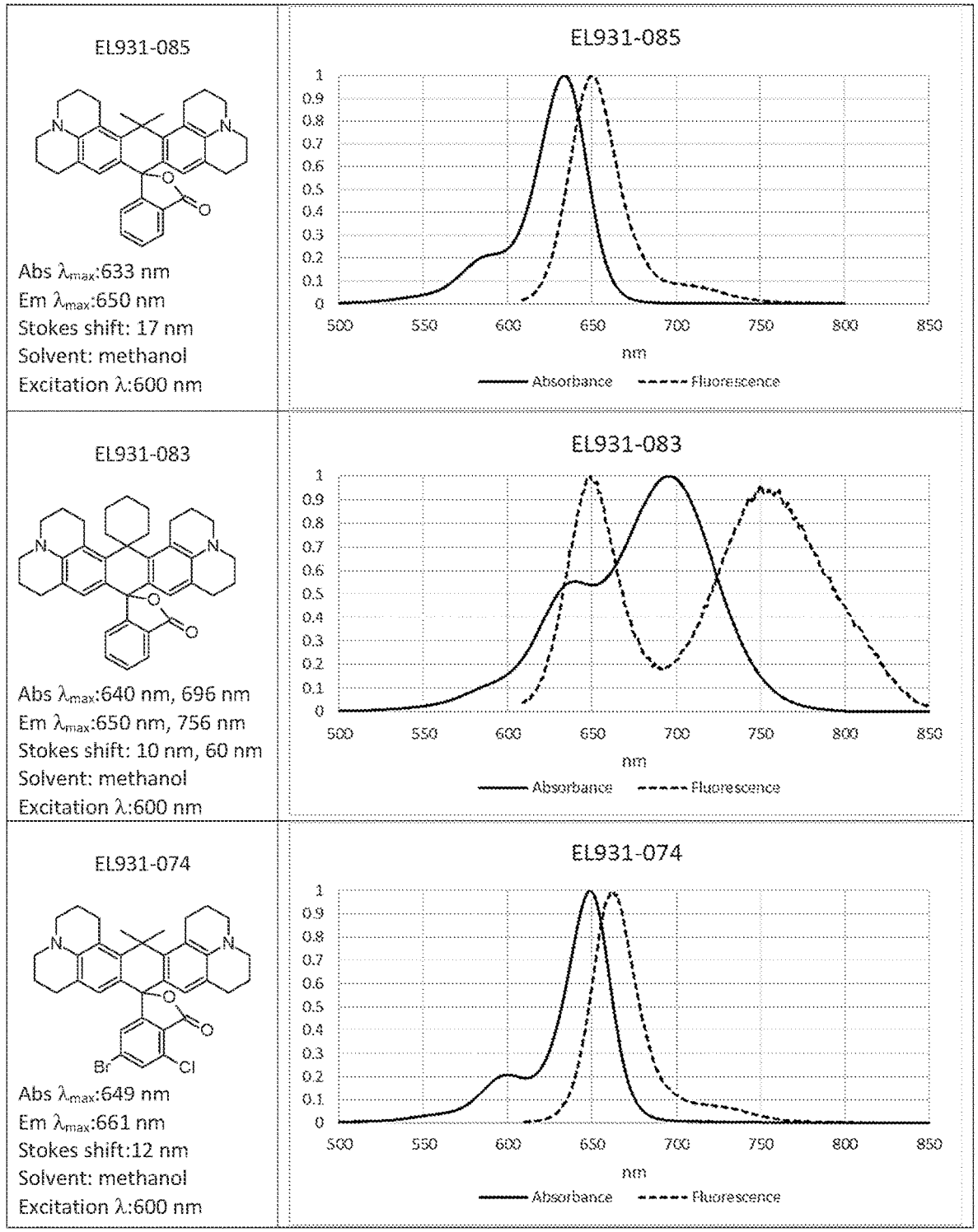
FIG. 11A shows UV-VIS and fluorescence data for exemplary carborhodamine compounds and conjugates synthesized according to methods of the disclosure.
Figure 11B:
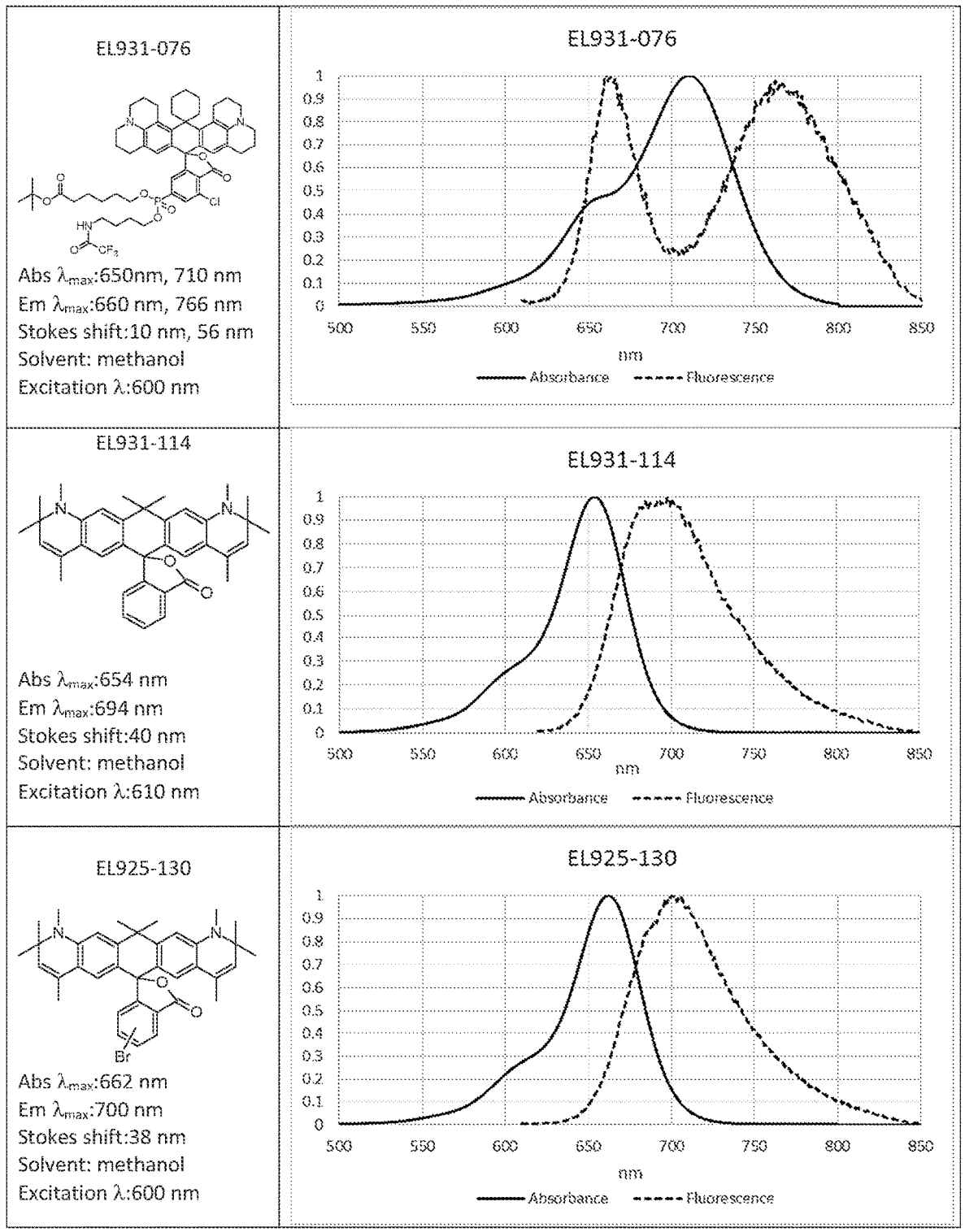
FIG. 11B shows UV-VIS and fluorescence data for exemplary carborhodamine compounds and conjugates synthesized according to methods of the disclosure.
Figure 11C:
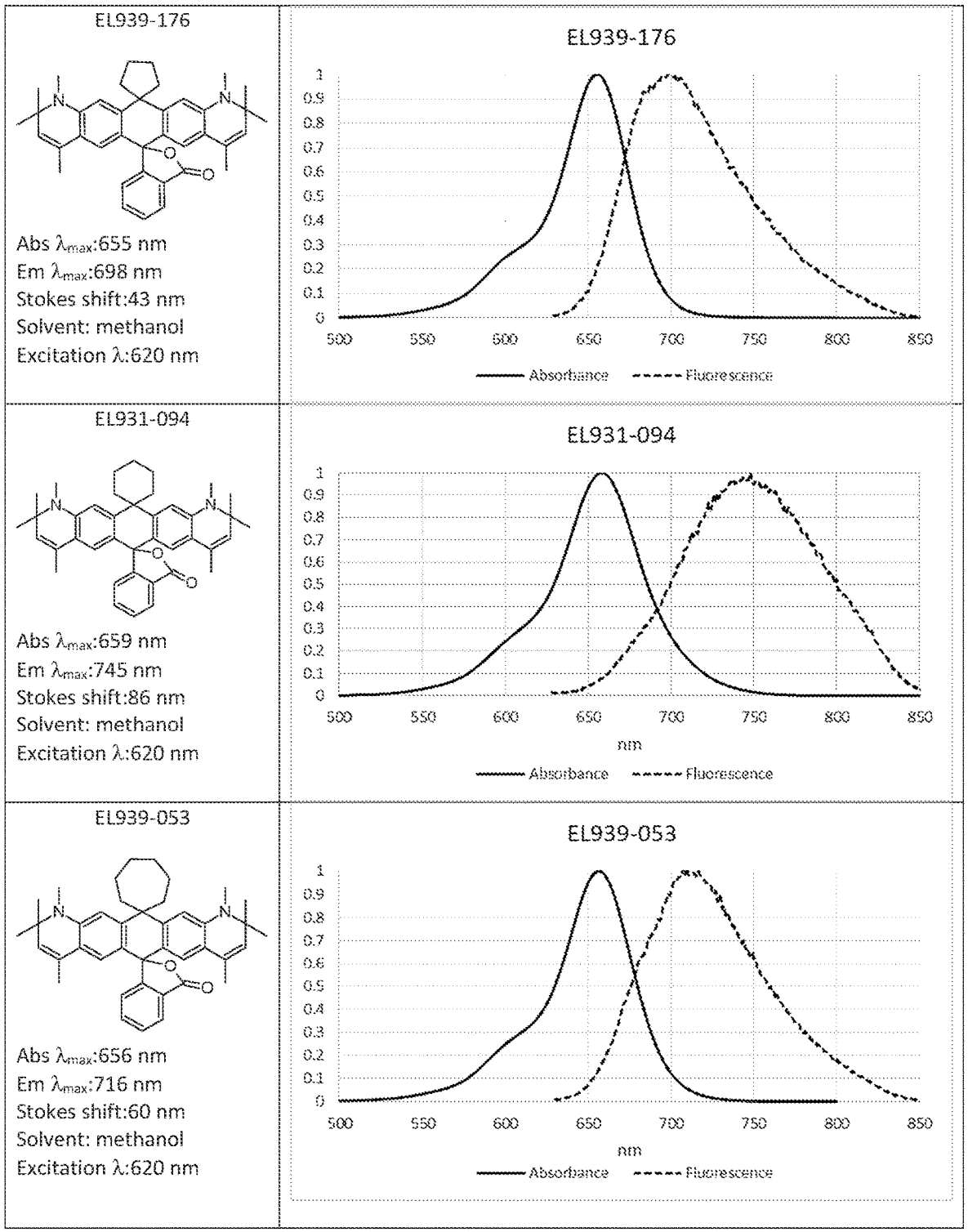
FIG. 11C shows UV-VIS and fluorescence data for exemplary carborhodamine compounds and conjugates synthesized according to methods of the disclosure.
Figure 11D:
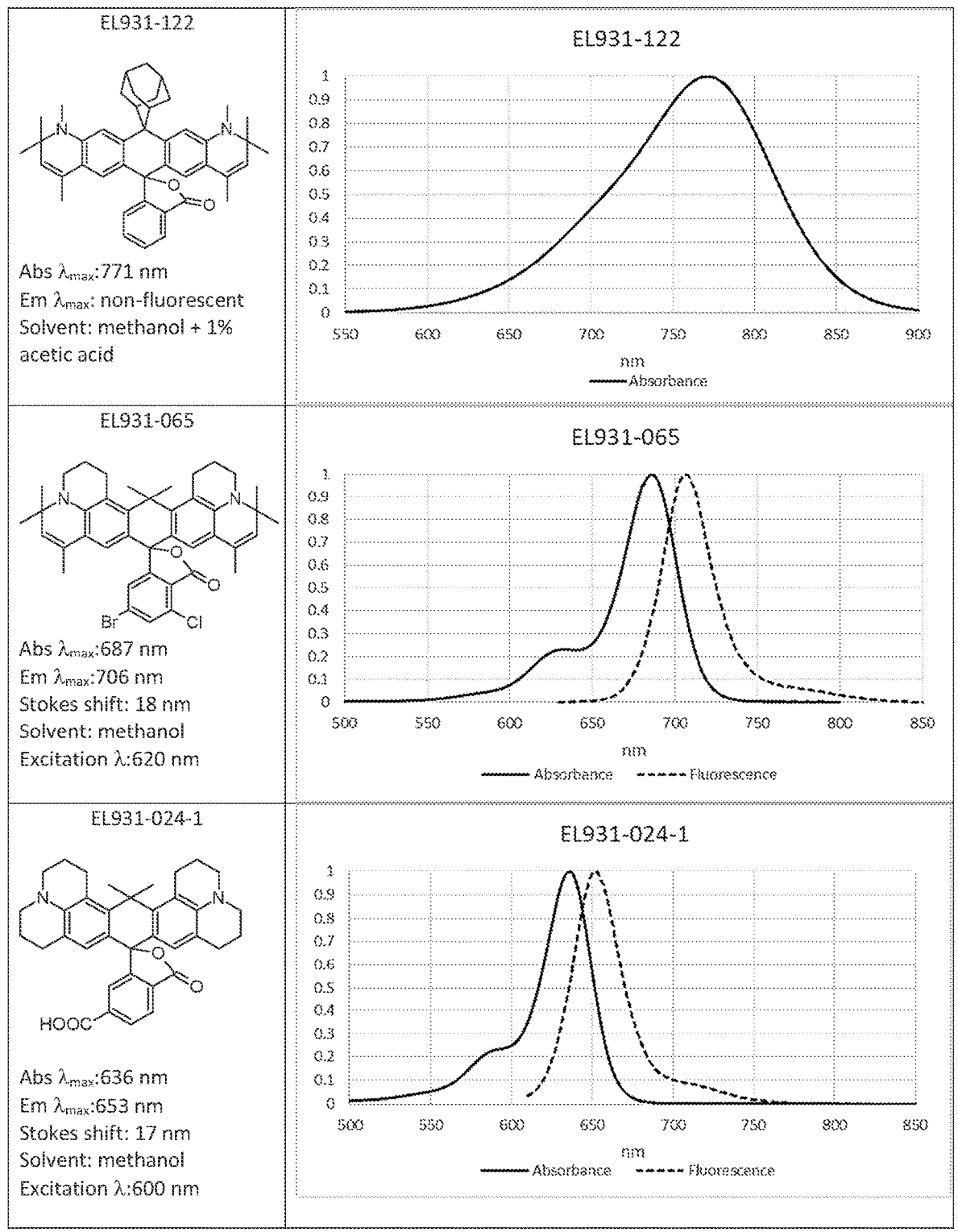
FIG. 11D shows UV-VIS and fluorescence data for exemplary carborhodamine compounds and conjugates synthesized according to methods of the disclosure.
Figure 11E:
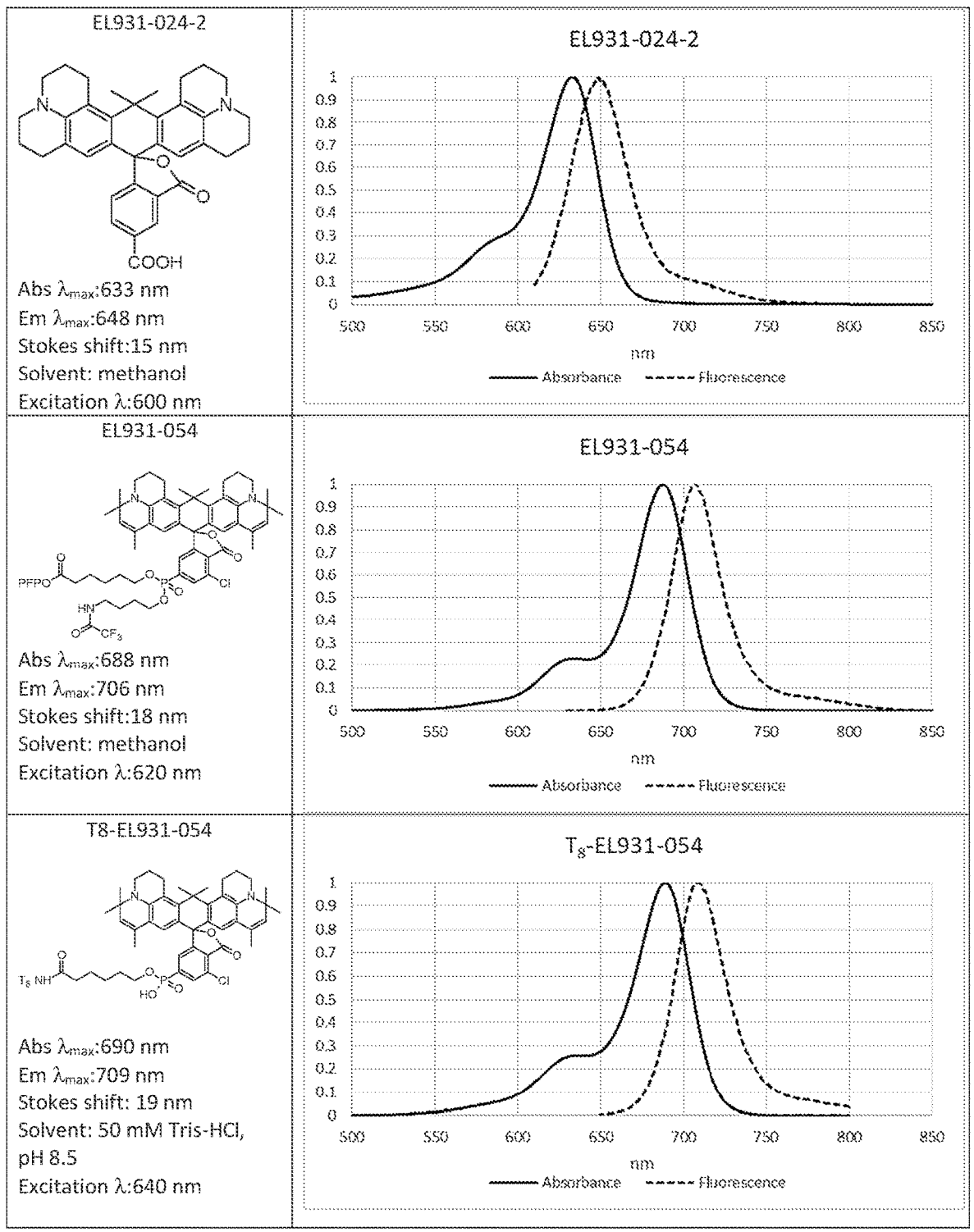
FIG. 11E shows UV-VIS and fluorescence data for exemplary carborhodamine compounds and conjugates synthesized according to methods of the disclosure.

PATENT NO. : 11,920,040 B2
APPLICATION NO. : 18/073929
DATED : March 5, 2024
INVENTOR(S) : Eugeny A. Lukhtanov It is certified that error appears in the above-identified patent and that said Letters Patent is hereby corrected as shown below:

In the Drawings
In Fig. 11E, Sheet 19 of 21, delete "T8-EL931-054" and insert -- $T_8$-EL931-054 --, therefor.

In the Specification
In Column 1, Line 7, delete "2021," and insert -- 2021, now U.S. Pat. No. 11,618,826, --, therefor.
In Column 1, Line 10, delete "2019," and insert -- 2019, now U.S. Pat. No. 11,155,713, --, therefor.
In Column 1, Line 54, delete "dye-phosphoramite" and insert -- dye-phosphoramidite --, therefor.
In Column 2, Line 11, delete "Spiro-" and insert -- spiro- --, therefor.
In Column 2, Line 41, delete "T8-carborhodamine" and insert -- $T_8$-carborhodamine --, therefor.
In Column 2, Line 43, delete "T8-carborhodamine" and insert -- $T_8$-carborhodamine --, therefor.
In Column 2, Line 46, delete "T8-carborhodamine" and insert -- $T_8$-carborhodamine --, therefor.
In Column 2, Line 48, delete "T8-carborhodamine" and insert -- $T_8$-carborhodamine --, therefor.
In Column 3, Line 39, delete "etc.)," and insert -- etc., --, therefor.
In Column 3, Line 61, delete "at al." and insert -- et al. --, therefor.
In Column 3, Line 62, delete "et al" and insert -- et al. --, therefor.
In Column 5, Line 11, delete "—OC(O) NR′R″," and insert -- —OC(O)NR′R″, --, therefor.
In Column 5, Line 23, delete "OR′ ," and insert -- —OR′ , --, therefor.
In Column 5, Line 51, delete "galactunoric" and insert -- galacturonic --, therefor.
In Column 6, Line 3, delete "for the" and insert -- to the --, therefor.
In Column 6, Line 12, delete "(1992)." and insert -- (1992)). --, therefor.
In Column 6, Line 19, delete "(e.g," and insert -- (e.g., --, therefor.
In Column 6, Line 51, delete "re-imission" and insert -- re-emission --, therefor.
In Column 7, Line 16, delete ""Super A°:"" and insert -- "Super A®: --, therefor.
In Column 7, Line 17, delete "1H" and insert -- $^1H$ --, therefor.
In Column 7, Line 38, delete "Spiro-" and insert -- spiro- --, therefor.
In Column 7, Line 39, delete "Spiro-" and insert -- spiro- --, therefor.
In Column 7, Line 65, delete "Spiro-" and insert -- spiro- --, therefor.
In Column 8, Line 25, delete "hereroalkyl," and insert -- heteroalkyl, --, therefor.
In Column 10, Line 27, delete "—OC(O) NR′R″," and insert -- —OC(O)NR′R″, --, therefor.

Signed and Sealed this
Fourth Day of June, 2024

*Katherine Kelly Vidal*
Katherine Kelly Vidal
*Director of the United States Patent and Trademark Office*

CERTIFICATE OF CORRECTION (continued)
U.S. Pat. No. 11,920,040 B2

In Column 10, Line 28, delete "— NR′C(O)NR″R‴," and insert -- —NR′C(O)NR″R‴, --, therefor.
In Column 10, Line 40, delete "Spiro-" and insert -- spiro- --, therefor.
In Column 10, Lines 45-46, delete "R11, R12, R13 and R14" and insert -- $R^{11}$, $R^{12}$, $R^{13}$ and $R^{14}$ --, therefor.
In Column 10, Line 54, delete "($C_1$-$C_{20}$)alkyl perfluoro($C_1$-$C_4$)alkyl" and insert -- ($C_1$-$C_{20}$)alkyl, perfluoro($C_1$-$C_4$)alkyl --, therefor.
In Column 10, Line 57, delete "Strucutres" and insert -- Structures --, therefor.
In Column 10, Line 60, delete "Spiro-" and insert -- spiro- --, therefor.
In Column 12, Line 37, delete "Spiro-" and insert -- spiro- --, therefor.
In Column 12, Line 66, delete "$R^8$)" and insert -- $R^{10}$ --, therefor.
In Column 13, Lines 2-3, delete "—OC(O) NR′R″," and insert -- —OC(O)NR′R″, --, therefor.
In Column 13, Line 32, delete "Spiro-" and insert -- spiro- --, therefor.
In Column 13, Line 39, delete "($C_1$-$C_5$)alkyl." and insert -- ($C_1$-$C_8$)alkyl. --, therefor.
In Column 13, Line 67, delete "(C1-$C_{20}$)" and insert -- ($C_1$-$C_{20}$) --, therefor.
In Column 15, Line 9, delete "—OC(O) NR′R″," and insert -- —OC(O)NR′R″, --, therefor.
In Column 15, Line 30, delete "(C1-C2O)alkoxy," and insert -- ($C_1$-$C_{20}$)alkoxy, --, therefor.
In Column 15, Line 35, delete "(C1-$C_4$)" and insert -- ($C_1$-$C_4$) --, therefor.
In Column 15, Line 37, delete "($C_1$-$C_{20}$)alkyl perfluoro($C_1$-$C_4$)alkyl," and insert -- ($C_1$-$C_{20}$)alkyl, perfluoro($C_1$-$C_4$)alkyl, --, therefor.
In Column 16, Line 31, delete "$T_8$ carborhodamine" and insert -- $T_8$-carborhodamine --, therefor.
In Column 16, Line 32, delete "$T_8$ carborhodamine" and insert -- $T_8$-carborhodamine --, therefor.
In Column 16, Line 66, delete "tetraisopropylphosphordiamidite" and insert -- tetraisopropylphosphorodiamidite --, therefor.
In Column 17, Line 3, delete "T8 oligonucleotide" and insert -- $T_8$ oligonucleotide --, therefor.
In Column 17, Lines 15-16, delete "The structure the structure" and insert -- The structure --, therefor.
In Column 17, Line 56, delete "5′-FI-ODN-3′-Q-MGB" and insert -- 5′-Fl-ODN-3′-Q-MGB --, therefor.
In Column 17, Line 57, "FI" and insert -- Fl --, therefor.
In Column 18, Line 9, delete "5′-MGB-Q-ODN-3′-FI" and insert -- 5′-MGB-Q-ODN-3′-Fl --, therefor.
In Column 18, Line 10, delete "FI" and insert -- Fl --, therefor.
In Column 18, Line 16, delete "oligonucleoptide" and insert -- oligonucleotide --, therefor.
In Column 18, Line 21, delete "5′-MGB—FI-ODN-3′-Q Structure XV" and insert -- 5′-MGB—Fl-ODN-3′-Q Structure XV --, therefor.
In Column 18, Line 22, delete "FI" and insert -- Fl --, therefor.
In Column 18, Line 32, delete "XIII-XXV," and insert -- XIII-XV, --, therefor.
In Column 23, Line 31, delete "(1)" and insert -- (I) --, therefor.
In Column 25, Line 37, delete "2-dihydroquinoline))" and insert -- 2-dihydroquinoline) --, therefor.
In Column 26, Line 1, delete "(Na2SO4)" and insert -- ($Na_2SO_4$) --, therefor.
In Column 26, Lines 3-4, delete "0-(2,2-diphenylcyclopentyl)S-methyl" and insert -- O-(2,2-diphenylcyclopentyl) S-methyl --, therefor.
In Column 26, Line 9, delete "(Na2SO4)" and insert -- ($Na_2SO_4$) --, therefor.
In Column 26, Line 13, delete "1H" and insert -- $^1H$ --, therefor.
In Column 26, Line 13, delete "CDCl3):" and insert -- $CDCl_3$): --, therefor.
In Column 26, Line 15, delete "13C" and insert -- $^{13}C$ --, therefor.
In Column 26, Line 15, delete "CDCl3):" and insert -- $CDCl_3$): --, therefor.

CERTIFICATE OF CORRECTION (continued)
U.S. Pat. No. 11,920,040 B2

In Column 28, Line 26, delete "JP566089)" and insert -- (JP 566089) --, therefor.
In Column 29, Line 1, delete "yiled" and insert -- yield --, therefor.
In Column 30, Line 53, delete "(1)" and insert -- (I) --, therefor.
In Column 30, Line 56, delete "(1)" and insert -- (I) --, therefor.
In Column 31, Line 65, delete "13C" and insert -- $^{13}$C --, therefor.
In Column 32, Line 28, delete "13C" and insert -- $^{13}$C --, therefor.
In Column 32, Line 29, delete "143.30128.59," and insert -- 143.30, 128.59, --, therefor.
In Column 33, Line 22, delete "mL" and insert -- mL) --, therefor.
In Column 34, Line 31, delete "repeated" and insert -- were repeated --, therefor.
In Column 37, Line 59, delete "δ 507.99" and insert -- δ 7.99 --, therefor.
In Column 37, Line 64, delete "50171.02," and insert -- δ 171.02, --, therefor.
In Column 39, Line 35, delete "29.0927.52," and insert -- 29.09, 27.52, --, therefor.
In Column 41, Line 1, delete "Compounds EL925-024-1 and EL925-024-2" and insert -- Compounds EL931-024-1 and EL931-024-2 --, therefor.
In Column 42, Line 62, delete "rotomers)" and insert -- rotamers) --, therefor.
In Column 44, Line 13, delete "J=7.5H," and insert -- J=7.5 Hz, --, therefor.
In Column 45, Line 2, delete "staring" and insert -- starting --, therefor.
In Column 46, Line 10, delete "rotomers):" and insert -- rotamers): --, therefor.
In Column 47, Line 1, delete "rotomers):" and insert -- rotamers): --, therefor.
In Column 51, Line 59, delete "partioned" and insert -- partitioned --, therefor.
In Column 51, Line 67, delete "rotomers):" and insert -- rotamers): --, therefor.
In Column 54, Line 58, delete "iABLE 4" and insert -- TABLE 4 --, therefor.
In Column 55, Line 1, delete "iABLE 4 - continued" and insert -- TABLE 4 - continued --, therefor.
In Column 55, Line 22, delete "an" and insert -- of an --, therefor.
In Column 55, Line 27, delete "iABLE 5" and insert -- TABLE 5 --, therefor.
In Column 55, Line 58, delete "Pleades" and insert -- Pleiades --, therefor.
In Column 55, Line 62, delete "Pleades" and insert -- Pleiades --, therefor.
In Column 56, Line 1, delete "iABLE 6" and insert -- TABLE 6 --, therefor.
In Column 56, Line 5, delete "instrument ELiie inGenius" and insert -- Instrument ELITe InGenius --, therefor.
In Column 56, Line 6, delete "GCAATCGTATTACCTiCTTATCGCAG" and insert -- GCAATCGTATTACCTCTTATCGCAG --, therefor.
In Column 56, Line 26, delete "concentration" and insert the same at Line 24 after "Target" as a continuation word.
In Column 57, Line 20, delete "4nd" and insert -- 4th --, therefor.

In the Claims
In Column 59, Lines 39-40, in Claim 1, delete "—OC(O) NR'R''," and insert -- —OC(O)NR'R'', --, therefor.
In Column 59, Line 51, in Claim 1, delete "—NR$^{iv}$R$^{v}$" and insert -- —NR$^{iv}$R$^{v}$, --, therefor.
In Column 59, Line 52, in Claim 1, delete "- —R$^{iv}$," and insert -- —R$^{iv}$, --, therefor.
In Column 59, Line 57, in Claim 1, delete "(C$_1$-C$_{20}$)alkyl perfluoro(C$_1$-C$_4$)alkyl," and insert -- (C$_1$-C$_{20}$)alkyl, perfluoro(C$_1$-C$_4$)alkyl, --, therefor.
In Column 59, Lines 66-67, in Claim 1, delete "NH$_2$(CH)$_4$-, NH$_2$(CH$_2$)$_5$-, CF$_3$C(O)NR'(CH$_2$)$_4$-," and insert -- NH$_2$(CH)$_4$—, NH$_2$(CH$_2$)$_5$—, CF$_3$C(O)NR'(CH$_2$)$_4$—, --, therefor.

CERTIFICATE OF CORRECTION (continued)
U.S. Pat. No. 11,920,040 B2

In Column 60, Line 14, in Claim 1, delete "NR'(CH$_2$)$_4$-, (CH$_3$)$_3$COC(O)NR'(CH$_2$)$_5$-," and insert -- NR'(CH$_2$)$_4$—, (CH$_3$)$_3$COC(O)NR'(CH$_2$)$_5$—, --, therefor.

SEQUENCE LISTING

```
Sequence total quantity: 6
SEQ ID NO: 1              moltype = DNA  length = 16
FEATURE                   Location/Qualifiers
source                    1..16
                          mol_type = other DNA
                          organism = synthetic construct
misc_feature              1
                          note = g is 4-hydroxy-6-amino pyrazolopyrimidine
SEQUENCE: 1
gcaaagtccc atcgtt                                                         16

SEQ ID NO: 2              moltype = DNA  length = 16
FEATURE                   Location/Qualifiers
source                    1..16
                          mol_type = other DNA
                          organism = synthetic construct
misc_feature              1
                          note = g is 4-hydroxy-6-amino pyrazolopyrimidine
SEQUENCE: 2
ggtggcatcg attatc                                                         16

SEQ ID NO: 3              moltype = DNA  length = 32
FEATURE                   Location/Qualifiers
source                    1..32
                          mol_type = other DNA
                          organism = synthetic construct
SEQUENCE: 3
aataaatcaa tgcgtgtatt agccttatcg gc                                       32

SEQ ID NO: 4              moltype = DNA  length = 31
FEATURE                   Location/Qualifiers
source                    1..31
                          mol_type = other DNA
                          organism = synthetic construct
SEQUENCE: 4
aataaatcat tcttgccatt cctttgtacc g                                        31

SEQ ID NO: 5              moltype = DNA  length = 25
FEATURE                   Location/Qualifiers
source                    1..25
                          mol_type = other DNA
                          organism = synthetic construct
```

```
SEQUENCE: 5
gcaatcgtat tacctcttat cgcag                                                    25

SEQ ID NO: 6          moltype = DNA  length = 24
FEATURE               Location/Qualifiers
source                1..24
                      mol_type = other DNA
                      organism = synthetic construct
SEQUENCE: 6
caaccatcgt catcgtcagg aaac                                                     24
```